United States Patent [19]
Harris et al.

[11] Patent Number: 6,083,690
[45] Date of Patent: Jul. 4, 2000

[54] METHODS AND COMPOSITIONS FOR IDENTIFYING OSTEOGENIC AGENTS

[75] Inventors: Stephen E. Harris; Gregory R. Mundy; Nandini Ghosh-Choudhury; Jian Q. Feng, all of San Antonio, Tex.

[73] Assignee: Osteoscreen, Inc., San Antonio, Tex.

[21] Appl. No.: 08/458,434

[22] Filed: Jun. 2, 1995

[51] Int. Cl.$^7$ .............................. C12Q 1/68; C12Q 1/02; C07H 21/04; C12N 15/85
[52] U.S. Cl. ................................... 435/6; 435/4; 435/29; 435/320.1; 435/325; 435/375; 435/455; 536/23.1; 536/24.1
[58] Field of Search ...................... 435/4, 6, 29, 172.3, 435/320.1, 325, 375, 440, 455; 536/23.1, 24.1

[56] References Cited

U.S. PATENT DOCUMENTS

| | | | |
|---|---|---|---|
| 5,166,058 | 11/1992 | Wang et al. | 435/69.1 |
| 5,266,683 | 11/1993 | Oppermann et al. | 530/326 |
| 5,491,084 | 2/1996 | Chalfie et al. | 435/189 |

FOREIGN PATENT DOCUMENTS

| | | |
|---|---|---|
| 0 629 697 | 12/1994 | European Pat. Off. . |
| WO 92/13091 | 8/1992 | WIPO . |

OTHER PUBLICATIONS

Alam et al., "Reporter genes: Application to the study of mammalian gene transcription", Anal. Biochm. 188(2): 245–254, Aug. 1990.

Ghosh–Choudhury, N. et al., "Expression of the BMP 2 Gene during Bone Cell Differentiation," *Critical Reviews in Eukaryotic Gene Expression* (1994) 4(2&3):345–355.

Harris, S.E. et al., "Retinoid Regulation of Bone Morphogenetic Protein 4 (BMP 4 or DVR 4): Analysis of the Mouse BMP 4 Gene Promoter by Transfection Into Primary Cultures of Fetal Rat Calvariae (FC) osteoblasts," *J Cell Biochem Suppl C* (17 Part A) (1993) 159.

Harris, S.E. et al., "Development of Osteoblast Cell Lines from Transgenic Mice Containing Bone Morphogenic Protein 2 (BMP2) Promoter–T–Antigen Constructs: Analysis of BMP 2 Retinoic Acid and 1,25(OH)$_2$ Vitamin D Response Regions in the BMP 2, Promoter in the Context of Chromatin Structure," *J Cell Biochem Suppl. C* (18B) (1994).

Anderson, H.C. et al., "Bone–Inducing Capability of Cultured Human Cells (FL and HELA) Compared to that of Various Types of Injury," Fed. Proceed. (1968) 27:475.

Bellows, C.G. et al., "Mineralized Bone Nodules Formed In Vitro from Enzymatically Released Rat Calvaria Cell Populations," *Calcif Tissue Int* (1986) 38:143–154.

Chen, D. et al., "Cloning and sequence of bone morphogenetic protein 4 cDNA from fetal rat calvarial cell," *Biochimica et Biophysica Acta* (1993) 1174:289–292.

Feng, J.Q. et al., "Structure and sequence of mouse bone morphogenetic protein–2 gene (BMP–2): comparison of the structures and promoter regions of BMP–2 and BMP–4 genes," *Biochimica et Biophysica Acta* (1994) 221–224.

Frost, E. et al., "Mapping Temperature–Sensitive and Host–Range Mutations of Adenovirus Type 5 by marker Rescue," *Virology* (1978) 91:39–50.

Gorman, C. "DNA Cloning, A Practical Approach" (Gover, D.M., ed) (1988) vol. II, pp. 157–158, IRL Press, Oxford, England.

Graham, F.L. et al., "A New Technique for the Assay of Infectivity of Human Adenovirus 5 DNA," *Virology* (1973) 52:456–467.

Hall, J.A. et al., "Acidic Fibroblast Growth Factor Gene 5' Non–Coding Exon and Flanking Region From Hamster DDT1 Cells: Identification of the Promoter Region and Transcriptional Regulation by Testosterone and aFGF Protein," *Journal of Cellular Biochemistry* (1993) 51:116–127.

Harris, S.E. et al., "Expression of Bone Morphogenetic Protein Messenger RNAs by Normal Rat and Human Prostate and Prostate Cancer Cells," *The Prostate* (1994) 24:204–211.

Harris, S.E. et al., "Effects of Transforming Growth Factor β on Bone Nodule Formation and Expression of Bone Morphogenetic Protein 2, Osteocalcin, Osteopontin, Alkaline Phosphatase, and Type I Collagen mRNA in Long–Term Cultures of Fetal Rat Calvarial Osteoblasts," *Journal of Bone and Mineral Research* (1994) 9(6):855–863.

Harris, S.E. et al., "Expression of Bone Morphogenetic Protein Messenger RNA in Prolonged Cultures of Fetal Rat Calvarial Cells," *Journal of Bone and Mineral Research* (1994) 9(3):389–394.

Kurihara, T. et al., "Murine Bone Morphogenetic Protein–4 Gene: Existence of Multiple Promoters and Exons for the 5'–Untranslated Region," *Biochemical and Biophysical Research Communications* (1993) 192(3):1049–1056.

Luckow, B., "CAT constructions with multiple unique restriction sites for the functional analysis of eukaryotic promoters and regulatory elements," *Nucleic Acids Res* (1987) 15:5490.

Majeska, R.J. et al., "Maintenance of parathyroid hormone response in clonal rat osteosarcoma lines," *Exp Cell Res* (1978) 111:465–467.

Majeska, R.J. et al., "Parathyroid Hormone–Responsive Clonal Cell Lines from Rat Osteosarcoma," *Endocrinology* (1980) 107(5):1494–1502.

Potter, H., "Electroporation in Biology: Methods, Applications, and Instrumentation," *Analytical Biochemistry* (1988) 174:361–373.

Sanger, F. et al., "DNA sequencing with chain–terminating inhibitors," *Proc Natl Acad Sci USA* (1977) 74(12) 5463–5467.

Stein, G.S. et al., "Relationship of cell growth to the regulation of tissue–specific gene expression during osteoblast differentiation," *Cell Growth and Gene Expression* (1990) 4:3111–3123.

(List continued on next page.)

*Primary Examiner*—Scott D. Priebe
*Attorney, Agent, or Firm*—Morrison & Foerster LLP

[57] ABSTRACT

Methods and compositions for identifying osteogenic agents are disclosed, wherein a bone morphogenetic protein promoter is utilized in an assay system to modulate the production of an assayable product of a reporter gene.

18 Claims, 26 Drawing Sheets

OTHER PUBLICATIONS

Urist, M.R., "Bone: Formation by Autoinduction," *Science* (1965) 150:893–899.

van den Hoff, M.J.B. et al., "Electroporation in 'intracellular' buffer increases cell survival," *Nucleic Acids Research* (1992) 20(11):2902.

Wozney, J.M. et al., "Novel Regulators of Bone Formation: Molecular Clones and Activities," *Science* (1988) 242:1528–1534.

Wozney, J.M., "The Bone Morphogenetic Protein Family and Osteogenesis," *Molecular Reproduction and Development* (1992) 32:160–167.

Wozney, J.M. et al., "Bone Morphogenetic Proteins," In: Physiology and Pharmacology of Bone (edited by Mundy, G.R., Martin, T.J.). Springer–Verlag, Chapter 20, (1993) pp. 725–743.

Feng, J.Q. et al., "The Mouse Bone Morphogenetic Protein–4 Gene,"*Journal of Biological chemistry,*vol. 270, No. 47, Nov. 24, 1995, pp. 28364–28373.

FIG. 1B-1

```
                                        INTRON IV              EXON IV
CACTGTGAGGAGTTTCCATCACGAAGgtcagtttctg... 985 bp...tgtgcctagAACATCTGGAGAACATCCCAGGGACCAGTGAGAGCTCTGCT    5801
 T  V  R  S  F  H  H  E  E                          H  L  E  N  I  P  G  T  S  E  S  S  A           138

TTTCGTTTCCTCTTCAACCTCAGCAGCATCCCAGAAATGAGGTGATCTCCTCGGCAGAGCTCCGGCTCTTTCGGGAGCAGGTGGACCAGGGCCCTGACT    5901
 F  R  F  L  F  N  L  S  S  I  P  E  N  E  V  I  S  S  A  E  L  R  L  F  R  E  Q  V  D  Q  G  P  D  W  172

GGGAACAGGGCTTCCACCGTATAAACATTTATGAAGCCCCCAGCAGAAATGTTCCTGGACACCTCATCACACGACTACTGGACACCAGACT            6001
 E  Q  G  F  H  R  I  N  I  Y  E  V  M  K  P  P  A  E  M  V  P  G  H  L  I  T  R  L  L  D  T  R  L   205

AGTCCATCACAATGTGACACGGTGGAAACTTTCGATGTGAGCCCTGCAGTCCTTCGCTGACCCGGAAAAGCAACCCATTATGGCTGCCATTGAG       6101
 V  H  H  N  V  T  R  W  E  T  F  D  V  S  P  A  V  L  R  W  T  R  E  K  Q  P  N  Y  G  L  A  I  E   238

GTGACTCACCTCACCAGACACGGACCATGTCAGAATCAGCCAGCATCGTTACCTCAAGGGAGTGGAGATTGGGCCCAACTCCGCCCC              6201
 V  T  H  L  H  Q  T  R  T  H  Q  G  Q  H  V  R  I  S  R  S  L  P  Q  G  S  G  D  W  A  Q  L  R  P  L  272

TCCTGGTCACTTTGGCCATGATGGCCGGGGCCCATACCTTGACCCCGCAGGAGGGCCAAACGTAGTCAGCCCAGAGAAGAAGAA                  6301
 L  V  T  F  G  H  D  G  R  G  H  T  L  T  R  R  R  A  K  R  S  P  K  H  H  P  Q  R  S  R  K  K  N   305

TAAGAACTGCCGTGCCATTCTACTGTGACTTCAGTGACGTGGGCTGAATGATTGGCCCCACCGGCTACCAGCCTTCTACTGCCAT                 6401
 K  N  C  R  R  H  S  L  Y  V  D  F  S  D  V  G  W  N  D  W  I  V  A  P  P  G  Y  Q  A  F  Y  C  H   338

GGGGACTGTCCCTTTCCACTGGCTGATCACCTCAACTCAACCATGTCAGACCCTAGTCAACTCTGTTAATTCTAGTATCCCTAAGGCCT             6501
 G  D  C  P  F  P  L  A  D  H  L  N  S  T  N  H  A  I  V  Q  T  L  V  N  S  S  I  P  K  A  C         372

GTTGTGTCCCCACTGAACTGAGTGCCATTCCATGTTGTACCTGATGAGTATGACAAGGTGGTGTTGAAAAATTATCAGGAGATGGTGTGTAGAGGGGTG    6601
 C  V  P  T  E  L  S  A  I  S  M  L  Y  L  D  E  Y  D  K  V  V  L  K  N  Y  Q  E  M  V  V  E  G  C    405

TGGATGCCGCTGAGATCAGACAGTCCGGAGGGGCGGACACACACACACACACACACACGTTCCCATTCAACCACCTA                         6701
 G  C  R  END                                                                                         408

CACATACCACACAAACTGCTTCCCTATAGCTGGACTTTTATCTTAAAAAAAAAAAAAAAAAAAGAAAGAAAAAAAATGAAAGACAGAAA             6801
AGAAAAAAAAAAAACCCTAAACAACTCACCTTGACCTTATTTATGACTTTACGTGCAAATGTTTTGACCATATTGATCATATTTGACAAATATATTTATAA 6901
       3'-FLANKING REGION

AACTACATATTAAAagaaataaatgag                                                                           6928
```

FIG. 1B-2

```
                                           DR-5
-2372  GAATTCGCTAGGTAGACCAGGCTGGCCC AGAACA CCTAG AGATCA TCTGGCTGCCCTCTGTCTCTTGAGTTCTGGGGCTAAAGCATG
-2286  CACCACTCTACCTGGCTAGTTTGTATCCATCTAAATTGGGGAAGAAAGAAGTACAGCTGTCCCCAGAGATAACAGCTGGTTTTCCATC
-2186  AAACACCTAGAAATCCATTTAGATTCTAAATAGGGTTTGTCAGGTAGCTTAATTAGAACTTTCAGACTGGGTTCACAGACTGGTT GG
       DR-1A Distal                                                                             DR-6
-2097  GCCA A AGGTCA CTTTATTGTCTGGGTTTCAGCAAAATGAGACAATAGCTGTTATTCAAACAACATTTGGGTAAGGAAGAAAAATGAA
                  Zif268
-2010  CAAACACCACTCTCCCT CCCCCCGC TCCGTGCCTCCAAATCCATTAAAGGCAAAGCTGCACCCCTAAGGACAACGAATCGCTGCTGTT
-1922  TGTGAGTTAAATATTAAGGAACACATTGTGTTAATGATTGGAGCAGCAGTGATTGATGTAGTGCATTGGTGAGCAC TGAATC CGTC
-1834  CT TCAACC TGCTATGGGAGCACAGAGCCTGATGCCCCAGGAGTAATGTGTGGGAGTAATGTAATGAGTAATGAGTTTAATTTGTGTT
-1746  GTTGTTTAAATAATAATTAATTGGCTGTGTTTGAATTTGAAAGAGAAGGTATCGAGTTTCGGTCTCGTGTTATTGCCAT
-1656  ACCTTGATTAATCGCAGGAATCAATCGTCTTCTAATAGAAAGAGAAGGTACTTAGAAACGATTTCAAATGTATGTTTCCAATGTGACTTCACTAAAG
-1566  TGACAGTGACGCAGGAGAATCAATCGTCTTCTAATAGAAAGAGAAGGTACTTAGAAACGATTTCAAATGAAGTATGTTTCAATCTTTCTGTTCTGGATGAGAGAGGTGG
-1476  TACCCATTGAATGAAAGAGACTTAGTCAGGGCAATACAGTGTGCTCCAAGGCTGGGATGGTCAGGATGTGTGTCCAGCCTCTAACAC
-1386  TCCTTCCAACCTGACATTCCTTCTCACCCTTGTCTTCTGGCCAGTAGAATACAGGAACTCGTTCCTGTTTTTTTTTAAATTCTGAA
                                                  Zif268
-1306  GGTGTGTAAGTACAA AGGTCA GATGAGCGGCCCT AGGTCA AGACTGCTTTGTGGTGACAAGGGAGTATAA CACCCACCC CAGAA
-1222  ACCAAGAACCGGAAATTGCTATCTTCCAGCTCCTGAAGCTCTGAAGCTGGCCTGCGCTGCCTTCCCTGCAGCTTTCCC
       DR-13
-1132  TTTAGCAGAGGCTGTGATTTCTTCAGCGCCTGGCAATATACTTCTTAGCCTGCCTCACCTTCCCATCCTCGTTGTTGTAAAAACAAAGATG
-1042  AAGCTGATAGTTCCTTCCCAGCTCCATCAGAGAGCCAGGTGAATTAGCTCCCTGTTTGGGAAGTTTAAAGCCGGCCACATTCCACCT
                                           AP-1
-952   CCCAGCTAGCATGATTACCAACTCTTGTTCTTACTGTTGTTATGAA AGACTCA ATTCCTACCATCTCCCTTCCCTTCTTTAAAAAG
       DR-1A Proximal
-865   GGGCCA A AGGGCA CTTTGTTTTTTTCTCTACATGCCTAAAAGGCACTGTGTTACCTTCCTGAAGGTCCAAACAAACAAACAAA
-779   CAAACAAAATAACCATCTGGCAGTTAAGAAGGCTTCAGAGATATAAATAGGATTTCTAATTGTCTTACAAGGCTAGGCTGTTTGCCTG
```

FIG. 1C-1

```
                                                              AP-2
-689  CCAAGTGCCTGCAAACTACCCTCTGTGCACTTGAGACCTGGGGGATCGATGA  GGGCACCC  AGTTTAAGGGGGGTTGGTGCA
-601  ATTCTCAAATGTCCACAAGAAACATCTCACAAAACTTTTTGGGGGAAAGTCACCTCCTAATAGTTGAAGAGGTATCTCCTTCGGGCA
                                            RB
-511  CACAGCCCTGCTCACAGCCTGTTTCAACGTTTGGGAATCCTTTAAACAGTTTACGGAAG  GCCACC  CTTTAAACCAATCCAACAGCTCCC
                                                                              AP-1
-423  TTCTCCATAAACCTGATTTTAGAGGTGTTTCATTATCTCTAATTACTCGGGTAAATGGTGA  TTACTCA  GTGTTTTAATCATCAGTTTG
                                                                              P53
-335  GGCAGCAGTTATTCTAAACTCAGGGAAGCCCATGGGGTATTTTTGAAGGTACAG  AGACTAGTTGGTGCATGCTT  TCTAGT
                                                                                    RB
                                                                                         SP-1
-247  ACCTCTTGCATGTGGTCCCCAGTGAGCCCCGGCTGCTTCCCGAGCTGAGGCATCGGTCCCAGCCAA  GGTGGC  AACTGAGGGCTGGG
-159  GAGCTGTGCAATCTTCCGGACCCGGCCTTGCCAGGCGAGGCCGTGCTGAGATGGGAGGATGT  GGGCGGGG  CTCCCCATCCC
                                                                              +1
                                                                         -1 ↑    ↓
 -71  AGAAGGGAGGGATTAAGGAGGAAGGGAGGGGAGGGGAGGGAAAGACTGGGGAGGAAGGAAGAAAGAGAGGAGGAA
                                                                                         +96
                              Zif268                                                    3'  ----
 +20  AAGAGAAGGAGGAAGGAGTAGATGT  GAGAGGGTG  GTGCTGAGGGTGGGAAGGCAAGAGCGCGAGGCCTGGCCCGGAAGCTAGGTGAGTTCG
                                                             EXON 1A
          +114
          -------- 5' Primer A
+108  GCATCCGAGCTGAGAGACCCAGCCTAAGACGCCTGCGCTGCAACCCAGCCTGAGTATCTGGTCTCCGTCCCTGATGGATTCTGTCTA
+198  AACCGTCTTGGAGCCTGCAGCGATCCAGTTCTCTGCCCCTGACCAGTTCATTGCAGCTTTCTAGAGGTCCCCAGAAGCAGCTGCTCG
+288  AGCCCGCTTCTGCAGGAACCAATGgtgag...INTRON1/1B PROMOTER....
```

FIG. 1C-2

Candidate E-box and Homeobox Binding Sites
in the BMP2 Promoter

```
-2736
*
GAATTCATTAAGCTGGATTCACTTCTAGTCCCATGCGTTTACACTCATTTCCACCACAAGAGGGCAGCCATCTCTAAAAAAACAACAG    -2647
TCGAGTGCTCTTCAGAGAAATTGGGCCAAACTGAGGAAAGTTCCTGGAAAGGCTTTTTAGCAGCACCTCTGGGCTACAAAAAAGAAGC    -2555
                                                                  * -2484 Eco RV
CAGCAGGCACCACCAAGGTGGAGTAACTGTCCAGAGGCATCCATTTTACCTCAGAGACTTG ATTA CTAAGGATATCCTAAACGGCCAAACTC    -2463
                                                             2
TCTCTTCTGTGTTCCAGAGGCCCAAAGCTGCAAGGCATTGTGATGTCATCACCAAAGGTTTCATTTCATCTTTTCTTGGGGTTGG    -2375
TCCAA CAGCT GTCAGCTTTCTCTTCCT ATTA AAGGCAACTTTCTCATTTAAATCTCATATAGTTCGAGTTTCTTGCTTTGCTCTTCCG    -2283
E-box 1                      3
CCTCCGCGATGACAGAAGCAATGGTTAACTTCTCA ATTA AACTTGATAGGGAAGGAAATGGCTTCAGAGGCGATCAGCCCTTTGACTTACA    -2191
                                   4
CACTTACACGTCTGAGTGGAGTGTTTATTGCCGCTTGGTGTCTCATGATTCAGAGTGACAACTTCTGCAACACGTTTTAAAAAG    -2101
GAATACAGTAGCTGATCGCAAATGCTGGATCTATCCCTTTAAT TCCCTGTAGACAGCCTTCCTTCAAAAATACCT TAT    -2011
                                 Xba -1996            5
TTGACCTCTACAGCTCTAGAAACAGCCAGGGC TAAT TTCCCTCTGTGGGTTGC TAAT CCGATTTAGGTGAACGAACTAGAGTTATTTT    -1921
                                                  6
AGCTAAAAGACTGAAAAGCTAGCA CACGTG GGTAAAAAAAATC ATTA AAGCCCCCTGCTTCTCGGTCTTCTTTGCTTTGCAAACTG    -1831
E-box 2                 7
GAAAGATCTGGTTCACAACGTAATCACTCTGGTCTTCTACAGAATGCTCAGCCCATAGTTTTGGGGGTCCTGTGGGTAGCCAGTGG    -1739
TGGTACTATAAGGCTCCTGAATGTAGGGAGAAATGAAAGATTCAAAAAGAATCCTGGCTCAGCAGCTTGG GGACATTTC AGCT GAGG    -1649
                                                                          E-box 3
AAGAAAACTGGCTTGCCACAGCCAGAGCCTTTCTGCTGGAGACCCAGTGGAGAGAGAGACCAGGCAGAAAATTCAAAGGTCTCAAACCG    -1559
```

```
         E-box 8
GCCACAAAGACACTTTGGCCCGAGGGCTCGGAGCGCGAGGTCACCCGGTTTGGCAACCCGAGACGCGCGGCTGAGACTGTCTCGAGAATGA   -307

GCCCCAGGACGCCGGGGCGCCAGCCGTGCGGGCTCTGCTGGCGAGCGCTGATGGGGTGCGCCAGAGTCAGGCTGAGGGAGTGCAGAG       -247

TGCGGCCCGCCCGCCACCCAAGATCTTCGCTGCGCCCTTGCCCGGACACGGCATCGCCACGATGCTGCCCCGAGCCATGGGTCGC          -130

GGCCCACGTAACGCAGAACGTCCAGAAGCGTCCCGGAGTCCCCGGAGCCAGCCCCGCGCCCAGCGCTGTCCCTGAGGCCGACGA           -40
         P53      zif268 -1↓ ↑+1                            E-box 9
CAGCAGCAGCCTTGCCTCAGCCTTCCCTCCGT|CCCGGCG|ACTCCTCCCCCTGCTCGAGGCTGTGTGTCAG|CACTTG|GCTGG            47

AGACTTCTTGAACTTGCCGGGAGAGTGACTTGGGCTCCCCACTTGGCGCCGGATCCAGTCTTGCCGCCTCCAGCCC                   139

Candidate         Homeobox 10 and 12 are identical at 8/8 sites, in an inverted
Homeo Box         orientation.
Binding           Homeobox 3, 4, 5, 9 should bind MSX1 and/or MSX2 with
sites             relatively high affinity.
```

FIG. 5C

```
   1  GAATTCATTT  AAGCTGGATT  CACTTCTAGG  TCCCATGCGT  TTACACTCAT
  51  TTCCACCACA  AGAGGGCAGC  CATCTCTAAA  AAAACAACAG  TCGAGTGCTC
 101  TTCAGAGAAA  TTGGGCCAAA  CTTGAGGAAA  GTTCCTGGGA  AAGGCTTTTT
 151  AGCAGCACCT  CTCTGGGCTA  CAAAAAAGAA  GCCAGCAGGC  ACCACCAAGG
 201  TGGAGTAACT  GTCCAGAGGC  ATCCATTTTA  CCTCAGAGAC  TTGATTACTA
 251  AGGATATCCT  AAACGGCCAA  ACTCTCTCTT  CTGGTGTTCC  AGAGGCCCAA
 301  AGCTGCAAGG  CATTGTTGAT  GTCATCACCA  AAGGTTTCAT  TTTCATCTTT
 351  TCTTGGGGTT  GGTCCAACAG  CTGTCAGCTT  TCTCTTCCTC  ATTAAAGGCA
 401  ACTTTCTCAT  TTAAATCTCA  TATAGGTTCG  GAGTTTCTTG  CTTTGCTCCT
 451  TCCGCCTCCG  CGATGACAGA  AGCAATGGTT  AACTTCTCAA  TTAAACTTGA
 501  TAGGGAAGGA  AATGGCTTCA  GAGGCGATCA  GCCCTTTTGA  CTTACACACT
 551  TACACGTCTG  AGTGGAGTGT  TTTATTGCCG  CCTTGTTTGG  TGTCTCATGA
 601  TTCAGAGTGA  CAACTTCTGC  AACACGTTTT  AAAAAGGAAT  ACAGTAGCTG
 651  ATCGCAAATT  GCTGGATCTA  TCCCTTCCTC  TCCTTTAATT  TCCCTTGTAG
 701  ACAGCCTTCC  TTCAAAAATA  CCTTATTTGA  CCTCTACAGC  TCTAGAAACA
 751  GCCAGGGCCT  AATTTCCCTC  TGTGGGTTGC  TAATCCGATT  TAGGTGAACG
 801  AACCTAGAGT  TATTTTAGCT  AAAAGACTGA  AAAGCTAGCA  CACGTGGGTA
 851  AAAAAATCAT  TAAAGCCCCT  GCTTCTGGTC  TTTCTCGGTC  TTTGCTTTGC
 901  AAACTGGAAA  GATCTGGTTC  ACAACGTAAC  GTTATCACTC  TGGTCTTCTA
 951  CAGGAATGCT  CAGCCCATAG  TTTTGGGGGT  CCTGTGGGTA  GCCAGTGGTG
1001  GTACTATAAG  GCTCCTGAAT  GTAGGGAGAA  ATGGAAAGAT  TCAAAAAAGA
1051  ATCCTGGCTC  AGCAGCTTGG  GGACATTTCC  AGCTGAGGAA  GAAAACTGGC
1101  TTGGCCACAG  CCAGAGCCTT  CTGCTGGAGA  CCCAGTGGAG  AGAGAGGACC
1151  AGGCAGAAAA  TTCAAAGGTC  TCAAACCGGA  ATTGTCTTGT  TACCTGACTC
1201  TGGAGTAGGT  GGGTGTGGAA  GGGAAGATAA  ATATCACAAG  TATCGAAGTG
1251  ATCGCTTCTA  TAAAGAGAAT  TTCTATTAAC  TCTCATTGTC  CCTCACATGG
1301  ACACACACAC  ACACACACAC  ACACACACAC  ACACATCACT  AGAAGGGATG
1351  TCACTTTACA  AGTGTGTATC  TATGTTCAGA  AACCTGTACC  CGTATTTTTA
1401  TAATTTACAT  AAATAAATAC  ATATAAAATA  TATGCATCTT  TTTATTAGAT
1451  TCATTTATTT  GAATATAAAT  GTATGAATAT  TTATAAAATG  TAATAATGCA
1501  CTCAGATGTG  TATCGGCTAT  TTCTCGACAT  TTTCTTCTCA  CCATTCAAAA
1551  CAGAAGCGTT  TGCTCACATT  TTTGCCAAAA  TGTCTAATAA  CTTGTAAGTT
1601  CTGTTCTTCT  TTTTAATGTG  CTCTTACCTA  AAAACTTCAA  ACTCAAGTTG
1651  ATATTGGCCC  AATGAGGGAA  CTCAGAGGCC  AGTGGACTCT  GGATTTGCCC
1701  TAGTCTCCCG  CAGCTGTGGG  CGCGGATCCA  GGTCCCGGGG  GTCGGCTTCA
1751  CACTCATCCC  GGACGCGACC  CCTTAGCGGC  CGCGCGCTCG  CCCCGCCCCG
1801  CTCCACCGCG  GCCCCGTACG  CGCCGTCCAC  ACCCCTGCGC  GCCCGTCCCG
1851  CCCGCCCGGG  GGATCCCGGC  CGTGCTGCCT  CCGAGGGGGA  GGTGTTCGCC
1901  ACGGCCGGGA  GGGAGCCGGC  AGGCGGCGTC  TCCTTTAAAA  GCCGCGAGCG
1951  CGCGCCAGCG  CGGCGTCGTC  GCCGCCGGAG  TCCTCGCCCT  GCCGCGCAGA
2001  GCCCTGCTCG  CACTGCGCCC  GCCGCGTGCG  CTTCCCACAG  CCCGCCCGGG
2051  ATTGGCAGCC  CCGGACGTAG  CCTCCCCAGG  CGACACCAGG  CACCGGAGCC
2101  CCTCCCGGCG  AAAGACGCGA  GGGTCACCCG  CGGCTTCGAG  GGACTGGCAC
2151  GACACGGGTT  GGAACTCCAG  ACTGTGCGCG  CCTGGCGCTG  TGGCCTCGGC
2201  TGTCCGGGAG  AAGCTAGAGT  CGCGGACCGA  CGCTAAGAAC  CGGGAGTCCG
2251  GAGCACAGTC  TTACCCTCAA  TGCGGGGCCA  CTCTGACCCA  GGAGTGAGCG
2301  CCCAAGGCGA  TCGGCGGAA  GAGTGAGTGG  ACCCCAGGCT  GCCACAAAAG
2351  ACACTTGGCC  CGAGGGCTCG  GAGCGCGAGG  TCACCCGGTT  TGGCAACCCG
2401  AGACGCGCGG  CTGGACTGTC  TCGAGAATGA  GCCCCAGGAC  GCCGGGGCGC
2451  CGCAGCCGTG  CGGGCTCTGC  TGGCGAGCGC  TGATGGGGGT  GCGCCAGAGT
2501  CAGGCTGAGG  GAGTGCAGAG  TGCGGCCCGC  CCGCCACCCA  AGATCTTCGC
2551  TGCGCCCTTG  CCCGGACACG  GCATCGCCCA  CGATGGCTGC  CCCGAGCCAT
2601  GGGTCGCGGC  CCACGTAACG  CAGAACGTCC  GTCCTCCGCC  CGGCGAGTCC
2651  CGGAGCCAGC  CCCGCGCCCC  GCCAGCGCTG  GTCCTGAGGG  CCGACGACAG
2701  CAGCAGCCTT  GCCTCAGCCT  TCCCTTCCGT  CCCGGCCCCG  CACTCCTCCC
2751  CCTGCTCGAG  GCTGTGTGTC  AGCACTTGGC  TGGAGACTTC  TTGAACTTGC
```

FIG. 9A

```
2801  CGGGAGAGTG ACTTGGGCTC CCCACTTCGC GCCGGTGTCC TCGCCCGGCG
2851  GATCCAGTCT TGCCGCCTCC AGCCCGATCA CCTCTCTTCC TCAGCCCGCT
2901  GGCCCACCCC AAGACACAGT TCCCTACAGG GAGAACACCC GGAGAAGGAG
2951  GAGGAGGCGA AGAAAAGCAA CAGAAGCCCA GTTGCTGCTC CAGGTCCCTC
3001  GGACAGAGCT TTTTCCATGT GGAGACTCTC TCAATGGACG TGCCCCCTAG
3051  TGCTTCTTAG ACGGACTGCG GTCTCCTAAA GGTAGAGGAC ACGGGCCGGG
3101  GACCCGGGGT TGGCTGGCGG GTGACACCGC TTCCCGCCCA ACGCAGGGCG
3151  CCTGGGAGGA CTGGTGGAGT GGAGTGGACG TAAACATACC CTCACCCGGT
3201  GCACGTGCAG CGGATCCCTA GAGGGGTTAG GCATTCCAAA CCCCAGATCC
3251  CTCTGCCTTG CCCACTGGCC TCCTTCCTCC AGCCGGTTCC TCCTCCCCAA
3301  GTTTTCGATA CATTATAAGG GCTGTTTTGG GCTTTCAAAA AAAAAAATGC
3351  AGAAATCCAT TTAAGAGTAT GGCCAGTAGA TTTTACTAGT TCATTGCTGA
3401  CCAGTAAGTA CTCCAAGCCT TAGAGATCCT TGGCTATCCT TAAGAAGTAG
3451  GTCCATTTAG GAAGATACTA AAAGTTGGGG TTCTCCATGT GTGTTTACTG
3501  ACTATGCGAA TGTGTCATAG CTTACACGTG CATTCATAAA CACTATCTAT
3551  TTAGTTAATT GCAGGAAGGT GCATGGATTT CTTGACTGCA CAGGAGTCTT
3601  GGGGAAGGGG GAACAGGGTT GCCTGTGGGT CAACCTTAAA TAGTTAGGGC
3651  GAGGCCACAA CTTGCAAGTG GCGTCATTAG CAGTAATCTT GAGTTTAGCG
3701  CTTACTGAAT CTACAAGTTT GATATGCTCA ACTACCAGGA AATTGTATAC
3751  AGCGCCTCTA AGGAAGTCAC TTGTGCATTT GTGTCTGTTA ATATGCACAT
3801  GAGGCTGCAC TGTATAAGTT TGTCAGGGAT GCAGTGTCCG ACCAACCTAT
3851  GGCTTCCCAG CTTCCTGACA CCCGCATTCC CAGCTAGTGT CACAAGAAAA
3901  GGGTACAGAC GGTCAAGCTC TTTTTAATTG GGAGTTAAGA CCAAGCCCCA
3951  AGTAAGAAGT CCGGCTGGGA CTTGGGGGTC CTCCATCGGC CAGCGAGCTC
4001  TATGGGAGCC GAGGCGCGGG GGCGGCGGAG GACTGGGCGG GGAACGTGGG
4051  TGACTCACGT CGGCCCTGTC CGCAGGTCGA CCATGGTGGC CGGGACCCGC
4101  TGTCTTCTAG TGTTGCTGCT TCCCCAGGTC CTCCTGGGCG GCGCGGCCGG
4151  CCTCATTCCA GAGCTGGCC GCAAGAAGTT CGCCGCGGCA TCCAGCCGAC
4201  CCTTGTCCCG GCCTTCGGAA GACGTCCTCA GCGAATTTGA GTTGAGGCTG
4251  CTCAGCATGT TTGGCCTGAA GCAGAGACCC ACCCCAGCA AGGACGTCGT
4301  GGTGCCCCCC TATATGCTAG ATCTGTACCG CAGGCACTCA GGCCAGCCAG
4351  GAGCGCCCGC CCCAGACCAC CGGCTGGAGA GGGCAGCCAG CCGCGCCAAC
4401  ACCGTGCGCA CGTTCCATCA CGAAGGTGAG CGGGCGGCGG GTGGCGGGGC
4451  GGGGACGGCG GCGGGCGGA GACTAGGCGG GCAGCCCGGG CCTCCACTAG
4501  CACAGTAGAA GGCCTTTCGG CTTCTGTACG GTCCCCTCTG TGGCCCCAGC
4551  CAGGGATTCC CCGCTTGTGA GTCCTCACCC TTTCCTGGCA AGTAGCCAAA
4601  AGACAGGCTC CTCCCCCTAG AACTGGAGGG AAATCGAGTG ATGGGAAGA
4651  GGGTGAGAGA CTGACTAGCC CCTAGTCAGC ACAGCATGCG AGATTTCCAC
4701  AGAAGGTAGA GAGTTGGAGC TCCTTAAATC TGCTTGGAAG CTCAGATCTG
4751  TGACTTGTGT TCACGCTGTA GTTTTAAGCT AGGCAGAGCA AGGGCAGAAT
4801  GTTCGGAGAT AGTATTAGCA AATCAAATCC AGGGCCTCAA AGCATTCAAA
4851  TTTACTGTTC ATCTGGGCCT AGTTTGAAAG ATTTCTGAAT CCCTATCTAA
4901  TCCCCGTGGG AGATCAATTC CACAATTCGT CATATTGTTT CCACAATGAC
4951  CTTCGATTCT TTGCTTAAAT CTTAAATCTC CAAGTGGAGA CAGCGCAACG
5001  CTTCAGATAA AAGCCTTTCT CCCACTGCCT GCTACCTTCC TAGGCAAGGC
5051  AATGGGGTTT TTAAACAAAT ATATGAATAT GATTTCCCAA GATAGAATAA
5101  TGTTGTTTAT TTCAGCTGAA ATTTCCTGGA TTAGAAAGGC TGTAGAGGCC
5151  TATTGAAGTC TCTTGCACCG ATGTTCTGAA AGCAGTTAGT AAAAAATCAT
5201  GACCTAGCTC AATTCTGTGT GTGCCACTTT CAATGTGCTT TTGACTTAAT
5251  GTATTCTCCA TAGAACATCA GTTCCTTCAA GTTCTAGAAG AATTCAGATT
5301  TAAAGTTTTG CTTTGCCTTG CTGAGGGGAT AAATTTTAAG TAGAAATCTA
5351  GGCTCTGAAA TGATAGCCCA ACCCCATCTC CAGTAAGGGA TGACTGACTC
5401  AAACCTTGAG AAGTCTGGGT GATAATAGGA AAAGTCCACA AGCAGGTCAC
5451  AGAGCGCGAG ATGGATCTGT CTTGAGGCAG CCAATGGTTA TGAAGGGCAC
5501  TGGAAATCCA TCTCTTTCAA ACTGGTGTCT AGGGCTTTCT GGGAGCAAAG
5551  CTTAGACCAC ATTCTGCTCC TCAAGGTTTG CCTACTGAAA GCAGGGAGAT
```

FIG. 9B

```
5601  TCTGGGTGTT  CACCCCCATC  CTTCACCCCC  AGGTGATTCT  GGGCTTAGCT
5651  AATCTCTCCT  GGTTAATATT  CATTGGAAAG  TTTTTATAGA  TCAAAACAAA
5701  CAAACCTACT  ATCCAGCACA  GGTGTTTTTC  CCACTGCCTC  TGGAGATATA
5751  GCAAGAAAAC  CATATATTCA  TGTATTTCCT  TATTAGTCTT  TTCTAACGTG
5801  AAAATTATTC  CTGACCTATA  AAAATGAAG   GAGGTATTTT  ATCTTAACTA
5851  AGCTAAAAGA  ATCGCTTAAG  TCAATTGAAA  CTCAAAAATC  CAATTGAATG
5901  AAAGGTTCGT  CAATAAAAAT  CTACATTTTT  CTTACTCTTC  CTTGGAAAT
5951  AGCTTGATAA  AAACACAGAC  AAAACAAAGT  CTGTGTGCTT  ATTTGAAAAC
6001  TTAGTGAGCT  TCAGTTCATA  AGCAAAAAAT  GTAGTTTAAA  AGTGATTTTT
6051  CTGTTGTAAA  ACGTGATAGA  AGTTATTGAC  TTGTTTAAAA  TAAACTTGCA
6101  CTAACTTTAT  ACCTTGGTGC  AATTAGATGT  AATGTTTACT  GTAAATTTCA
6151  GGAAAACCAT  TTTTTTTTTT  TGGTCATGAT  CAGGTACACA  TGGCATTTGG
6201  GAAGACTTTT  CACATTGTTG  AGTAACCTAG  AGTTTGTTTG  TTTGTTTGTT
6251  TGTTTTTAAG  CATTCTTGTG  CCACTAGAAA  AACCTTAATA  AGCCATGTGT
6301  TACTTGGTAG  ACTTCTTCCT  AAGTTCTAGA  AAGTGGCTTA  ATGCCACGAT
6351  GAGACAAAAC  ATACCATAGT  AGTCTTTCAA  CCAGTGGCAG  AGTCTTCCAG
6401  ACAAAATCTC  CTGTTAACA   TTAAGACCAT  GGATTTTTAT  CCAGGAGAGC
6451  CCAGGCTTTG  CTGAATCACC  ACCCTCCAAC  CCCACTCCAA  GGTCACCGAA
6501  GGCCTCCCCA  ACTGGCTGCC  ATTGAGAAAC  TGTTTGAAAT  TGATTGACTC
6551  CATTGGCCCT  ACAGAGACTT  CTCCTTTAGT  GGCAGATCAT  ATACTGAAGG
6601  ATCCAAGCTT  GCTCTTCTGA  CTATGAAGAG  CACAGTCTTT  CTTTTTCTTT
6651  ATGGAATAAA  CAAACTATGT  GGCCCTGTGA  CTAAAGTTTT  CAAAGAGGGA
6701  GAGATCCTGT  TAGCAGAAGT  GCAACTGCCC  AGAAACTAGC  CACAGGCTAG
6751  GATATTCCAA  AGTACAACTC  TAAAGTATGG  TCCATCCTAA  ATTCTAGCAT
6801  GGGGTTGAAT  ACCGGCATCC  AGGAATACTT  CTCTCTACCT  CTGGCTATTG
6851  CAGTGAGATT  ACGAAGACCC  TGGGGGGAAA  AACAGTTGCT  TAGTTTACAG
6901  ATGTTCCTTG  CCACAGATGT  TCTCAGTATC  TCTTGTTTGT  CAGAGGATCC
6951  TTTCAATCCC  TCTTGACATT  TCCAATCTGC  TTTTGTCCTC  TCTACATGTG
7001  CCTTGTGGCA  TTTCGCTTGG  TCTTTAGAGA  ATCCCTTTCT  GGAGCTGCAG
7051  GTTCCCTTGT  AGGATCTGTG  TTCAGGAGAA  CAGGGACCTT  GGCAGGTTAG
7101  TGACAACTAC  CAAACCCTGC  TTTCCTTCCC  TGCCACTTCC  TTTGTTGCCT
7151  TAAAAATTAA  ACCTTAACTC  TCTGTGTCTA  AACCTTTTCT  TCTTCCTCTT
7201  TGTCATTTAC  TTTATTTATT  TGTCATGTAC  TTTATCCTGT  AGAAAATCAC
7251  AGTGTGGCCC  AAAGCCCTT   GAATCTTGTT  GCAGCGGTGA  GATGCAGCTG
7301  CTGATCTGGA  ATAGCCTTAG  GCTGTGTGTT  TGATCACAAT  GCTTTCTGTC
7351  CAAAAGTGTG  CAAATCCTCC  AAGCTTAATG  ATAACTTTTG  AAATGAAACT
7401  CACCCTACTT  TAGGGCAAAC  AAGTAGCCAC  AGAGAGCAGG  ATCTAAACAA
7451  GGTCTGGTGT  CCCATTTGGC  TGTGTCCCTT  CAATTTTCTG  TTCATTTAGC
7501  TCTGTCTGCA  TCTAAAGGGT  GCTGGGCAAT  AAGTTTTGAT  CTTCAGGGCA
7551  AAACTCAATC  TTCAGTTACC  ATGGTATCAG  GTACCAATTC  CTAGTGATTT
7601  GTGCTATGGC  TTAGGATTTG  ATTTCTCTCC  TACATTAGGT  AATATCTTTC
7651  AATGGCTAGA  ACTTGGGCAT  TGCAGTACAC  TCAAGTTAAC  AGTTCTGTGA
7701  CCTAAGGAAG  TCACATAACC  TCTCTGAATT  CTCTACTGTT  TCATTCACAA
7751  AATGGAGAAA  ATCATGGCTC  TTTCTTAATG  TGCGAATTCA  TAGAAAGGTG
7801  ATGACACCAG  ATTTGGCAGA  AGGAAGGAAA  GGAAGGAAGG  AAGAAAGAAA
7851  GAAAGAAAGA  AAGAAAGAAA  GAAAGAAAGA  AAGAAAGAAA  GGAAGGAAGG
7901  GAGAGAGAGA  GAAGGGAAGG  GAAAGGGAAA  GGGAAAGGAA  AGAAAAGAAA
7951  GGAAGGAAGA  AAAGGAAGGA  AGGAAGGAAA  GAAGGAAGGA  AGGAAAAGAA
8001  AGAAGAAAA   GCATTCAGCA  TATGAACTAA  TGTTTCCTGG  TGACTTTTA
8051  TATCATATCC  TTGTTCTAGG  AAGTGGCCCT  AGCCATATCT  TTTGGGTTAT
8101  TTTGAGGTAG  AGGATAATCA  ACATAGTGTA  GAACATTAAA  TCTGGGTTTT
8151  GTTTCTAGAA  GAGGCTAGAA  TGGCATGGCT  GTCCCACTTG  CTCCTCTTTC
8201  AGGCAGTATG  GCAGCCACCA  TTCTCTCTGT  AAGATCTAGG  AGGCTGACAC
8251  TCAGGTTGGA  GACAGGTCAG  AATCCTGAAA  TCACTTAGCA  AGTTCAGCTG
8301  ATTCAACAAG  GGATATTTAC  AGAGAATTAA  CAGCTATTCC  AGCTTCCAAA
8351  AAGTGTACAT  TACCTACTCT  GTATTTTCAG  AACCCCAGGT  TTGCTGTGAT
```

FIG. 9C

```
8401  AATTTGGTAG AAGCCTTTTC CTGTAATTTT CTTTATTTAA AAGATATTTT
8451  CATTTTCCAC CCTCAAGAAG AGGTTGAAAC TTGTCCCTTG AAGTAGAAGA
8501  GGTGTTGTGT GTCCTGACCC TGAGGAAGTT GGCCTTGTTG AGGTCTTCTG
8551  TAAATTCTTG AATTCTCTGT ATAATTTCAA TGAATAGTCA TGTTTGATAC
8601  CTTGGTATAA AGGATGGGAT AAGATCTTTC AAGGCTTAGG CTGATGGAAA
8651  CGCTGCTGAA AGACTAGAGA TTGCTCTTTC CTTTGGCATC TGTCTTGGGT
8701  AGTAATATTG TTCTCTGTGA AGGCCCACTT ATTCTGTCTT GAAAATTCTT
8751  CTTACCTCCA GAGTGATAGG CCACAGGGAG TACTGTTTCT ATGTTTGCAG
8801  TTGAAAGATG ACAATTTCAT ATGGTCCAAA CTTGGCTTTA TTTCTTGGTG
8851  AGATATTATT CTGTTACTTC AATGACCTGT CTCCATTATT TATCTTGAGG
8901  CTCACCTCTT CCCTTTTGTT GACTGTTGTG CAATTTGTGG AAGGCCCTGG
8951  GTAGTCAGCC TTTATACTCT GTCTGTACAG GAAATAAAGT GCATGTCACC
9001  ATGCCAAAGT CAGGAGATGC CGGTGTGATT AGGGTCCACG GGATTTTGCT
9051  ACTGTTTTTA TTTCTATCGA TGAATTGCCT TAGGCAGAAA CATTAAGGGA
9101  CACCAGAATG GTGATGAAAG GCTTTTTATA ACAGAAGCTA AATGCAGTCC
9151  TTCATACTTC ATGGAATGCC CCTGTCCTAA AGTACCATTA ACCGATAGTG
9201  GAGTCAGAAC ATAAATGGCT CCCCAAAGGT ATCACCAAGA ACTTTTGGCA
9251  AACAGATGCA AGAGGATTAT GAAGAATCGC AGCTTGGTCT GGTAATCTTC
9301  CTGTTGCAAA GAGAAGAGCT TTAGAAGACC CCCCTTGAGT CCCTGGCTGG
9351  CTTAACATAG CATGAACCCT CATGTGTTGG CCAACATTAA GGCTTTTCT
9401  ATAAAAGTCT CCTCCTTCAT CAGTATACGC TCGAGTATGA AAAGCATCCT
9451  TTTAAACCTT GACTCTGTGT GGTCCAGAAA CAGCAGCATC CCTTGCTTAA
9501  GAGCTTAATG GAGATGCAGG AGTGCAGGCC TCTTCCCAGA CCGGCTGATG
9551  TGCAGGTCAA AGTCTAAGCA CTGCTGGATC AACACAGAAG TTATTCCGAA
9601  TGAGGATGAG ATGGATACGA GAGAACAGGA AGTAGGAAGG GATTTCTTTA
9651  TCGTGAATTG CTACAGCAGC CTAATGTCAC CCCATACCCT TCTGAAGAAC
9701  TATGTCCCTG TGGATGCCTT TGTCTCTAGA GTTCTGAGCA AATGGTAGG
9751  GTGTGCTTTG CAAAATGTCA TCATTGATGT TGAATTTCAA AGTCTTTAAT
9801  TAAGGGGCTG AAATCTGTAT ATTGAGATTT GTAAATCATC TAAATTGTAG
9851  AGTAATGTTT GCACAGGCTG CTTAAGGGAT TGACATTAAA GCTCGTTTTC
9901  TTAGTTAAGA AATACAGTCA TTTCCTCAAC TCCTCAGTCA TTAGCTCTCT
9951  ACTAAGTACA GTGCTGACTT TTTTAAAATT AAAGTCTGTG AATTCCAAAG
10001 AAGTGTTTCA CTATTTCCTC CATTATTATA GCTACCTAGA AGCTATGTTC
10051 ATATATTGGA TTAAAAACGT AGCAATTACA AAGTTAATGT GGCCATATAG
10101 AAAAGGGAAA AGAAACTCCG CTTTCACTTT AATATATATA TGTGTGTGTG
10151 TATATCATAT ATATACATGT TGTGTGTGTA TATATATATA TATATATATA
10201 TATATATATA TATATATATA TATATATATA TGTTGTGTTA AGCAGTAAAC
10251 TCAGGCCATG GACAGAGGGG CAGACATTGT ATCTCTAGGC CTGACATTTT
10301 TAATTTCTGG TTGCAGGTTT TTATGTAGTT TAACTTAAAC CATGCACTGA
10351 AGTTTTAAAT GCTCGTAAGG AATTAAGTTA CCATTGGCTC TCTTACCAAA
10401 TGCGTTTCTT TTTTCTCTCC ACCCTGATCA AACTAGAAGC CGTGGAGGAA
10451 CTTCCAGAGA TGAGTGGGAA AACGGCCCGG CGCTTCTTCT TCAATTTAAG
10501 TTCTGTCCCC AGTGACGAGT TTCTCACATC TGCAGAACTC CAGATCTTCC
10551 GGGAACAGAT ACAGGAAGCT TTGGGAAACA GTAGTTTCCA GCACCGAATT
10601 AATATTTATG AAATTATAAA GCCTGCAGCA GCCAACTTGA AATTTCCTGT
10651 GACCAGACTA TTGGACACCA GGTTAGTGAA TCAGAACACA AGTCAGTGGG
10701 AGAGCTTCGA CGTCACCCCA GCTGTGATGC GGTGGACCAC ACAGGGACAC
10751 ACCAACCATG GGTTTGTGGT GGAAGTGGCC CATTTAGAGG AGAACCCAGG
10801 TGTCTCCAAG AGACATGTGA GGATTAGCAG GTCTTTGCAC CAAGATGAAC
10851 ACAGCTGGTC ACAGATAAGG CCATTGCTAG TGACTTTTGG ACATGATGGA
10901 AAAGGACATC CGCTCCACAA ACGAGAAAAG CGTCAAGCCA AACACAAACA
10951 GCGGAAGCGC CTCAAGTCCA GCTGCAAGAG ACACCCTTTG TATGTGGACT
11001 TCAGTGATGT GGGGTGGAAT GACTGGATCG TGGCACCTCC GGGCTATCAT
11051 GCCTTTTACT GCCATGGGGA GTGTCCTTTT CCCCTTGCTG ACCACCTGAA
11101 CTCCACTAAC CATGCCATAG TGCAGACTCT GGTGAACTCT GTGAATTCCA
11151 AAATCCCTAA GGCATGCTGT GTCCCACAG AGCTCAGCGC AATCTCCATG
```

FIG. 9D

```
11201  TTGTACCTAG ATGAAAATGA AAAGGTTGTG CTAAAAAATT ATCAGGACAT
11251  GGTTGTGGAG GGCTGCGGGT GTCGTTAGCA CAGCAAGAAT AAATAAATAA
11301  ATATATATAT TTTAGAAACA GAAAAAACCC TACTCCCCCT GCCTCCCCCC
11351  CAAAAAAACC AGCTGACACT TTAATATTTC CAATGAAGAC TTTATTTATG
11401  GAATGGAATG AAAAAAACAC AGCTATTTTG AAAATATATT TATATCGTAC
11451  GAAAAGAAGT TGGGAAAACA AATATTTTAA TCAGAGAATT ATTCCTTAAA
11501  GATTTAAAAT GTATTTAGTT GTACATTTTA TATGGGTTCA ACTCCAGCAC
11551  ATGAAGTATA AGGTCAGAGT TATTTTGTAT TTATTTACTA TAATAACCAC
11601  TTTTTAGGGA AAAAAGATAG TTAATTGTAT TTATATGTAA TCAGAAGAAA
11651  TATCGGGTTT GTATATAAAT TTTCCAAAAA AGGAAATTTG TAGTTTGTTT
11701  TTCAGTTGTG TGTATTTAAG ATGCAAAGTC TACATGGAAG GTGCTGAGCA
11751  AAGTGCTTGC ACCACTTGCT GTCTGTTTCT TGCAGCACTA CTGTTAAAGT
11801  TCACAAGTTC AAGTCCAAAA AAAAAAAAAA AGGATAATCT ACTTTGCTGA
11851  CTTTCAAGAT TATATTCTTC AATTCTCAGG AATGTTGCAG AGTGGTTGTC
11901  CAATCCGTGA GAACTTTCAT TCTTATTAGG GGGATATTTG GATAAGAACC
11951  AGACATTACT GATCTGATAG AAAACGTCTC GCCACCCTCC CTGCAGCAAG
12001  AACAAAGCAG GACCAGTGGG AATAATTACC AAAACTGTGA CTATGTCAGG
12051  AAAGTGAGTG AATGGCTCTT GTTCTTTCTT AAGCCTATAA TCCTTCCAGG
12101  GGGCTGATCT GGCCAAAGTA CTAAATAAAA TATAATATTT CTTCTTTATT
12151  AACATTGTAG TCATATATGT GTACAATTGA TTATCTTGTG GGCCCTCATA
12201  AAGAAGCAGA AATTGGCTTG TATTTTGTGT TTACCCTATC AGCAATCTCT
12251  CTATTCTCCA AAGCACCCAA TTTTCTACAT TTGCCTGACA CGCAGCAAAA
12301  TTGAGCATAT GTTTCCTGCC TGCACCCTGT CTCTGACCTG TCAGCTTGCT
12351  TTTCTTTCCA GGATATGTGT TTGAACATAT TTCTCCAAAT GTTAAACCCA
12401  TTTCAGATAA TAAATATCAA AATTCTGGCA TTTTCATCCC TATAAAAACC
12451  CTAAACCCCG TGAGAGCAAA TGGTTTGTTT GTGTTTGCAG TGTCTACCTG
12501  TGTTTGCATT TTCATTTCTT GGGTGAATGA TGACAAGGTT GGGGTGGGGA
12551  CATGACTTAA ATGGTTGGAG AATTCTAAGC AAACCCCAGT TGGACCAAAG
12601  GACTTACCAA TGAGTTAGTA GTTTTCATAA GGGGCGGGG GGAGTGAGAG
12651  AAAGCCAATG CCTAAATCAA AGCAAAGTTT GCAGAACCCA AGGTAAAGTT
12701  CCAGAGATGA TATATCATAC AACAGAGGCC ATAGTGTAAA AAAATTAAAG
12751  AATGTCTGAT CAGCGTCTCA GCACATCTAC CAATTGGCCA GATGCTCAAA
12801  CAGAGTGAAG TCAGATGAGG TTCTGGAAAG TGAGTCCTCT ATGATGGCAG
12851  AGCTTTGGTG CTCAGGTTGG AAGCAAAACC TAGGGAGGGA GGGCTTTGTG
12901  GCTGTTTGCA GATTGGGGAA TCCAGTGCTA GTTCCTGGCA GGGTTTCAGG
12951  TCAGTTTCCG GAGTGTGTGT CCTGTAGCCC TCCGTCATGG TTGAAGCCCA
13001  GGTCTCACCT CCTCTCCTGA CCCGTGCCTT AGAACTGACT TGGAAAGCGG
13051  TGTGCTTACA GCAAGACAGA CTGTTATAAT TAAATTCTTC CCAAGGACCT
13101  CCGTGCAATG ACCCCAAGCA CACTTACCTT CGGAAACCTT AAGGTTCTGA
13151  AGATCTTGTT TTAAATGACT ACCCTGGTTA GCTTTGATG TGTTCCTTAT
13201  CCCTTTAGTT GTTGCACAGG TAGAAACGAT TAGACCCAAC TATGGGTAGC
13251  CTTGTCCTCC TGGTCCTTCA GTCATTCTCT AATGTCTCTT GCTTGCCATG
13301  GGCACTGTAA CAAACTGCAA TCTTAACATC TTATAAAATG AATGAACCAC
13351  ATATTTACAT CTCCAAGTCC TCCAGATGGG AGTGCGATCA TTCCATAAGG
13401  ATCCCACCTT CTGGCAGGTC TATCCAGTAC ATATTTTATG CTTCATTGGT
13451  CTTGATTTTC TTGGCTAAAA TTACTTGTAG CACAGCAGGC CCCATGTGAC
13501  ATATAGGTAT ATACATACAT GTATGTGCAT ATAGTGTGTA CATGTTCTAA
13551  TTTATACATA GCTATGTGAA GATTATGTTA CATATGTAGA TGGTCGCACT
13601  TCTGATTTCC ATTTAGGTTC AGAGAGAGAC GTCACAGTAA ATGGAGCTAT
13651  GTCATTGGTA TATCCCCGAG TGGTTCAGGT GTTCTCTCTA TTTTTTTAAG
13701  ATGGAGAACA CTCATCTGTA CTATCGAAAA CTGAGCCAAA TCACTTAGCA
13751  AATTTCTAGT CACTGCCTTG CTGTTAAGAT ACTGATTCAC TGGGTGCTGA
13801  CATGCTGAGC CCTGCCTACT TTTGCATGAA GGACAAGGAA GAGAGCTTGC
13851  AGTTAAGAAT GGTATATGTG GGGCTAGGGG GCGGCGTATA GACTGGCATA
13901  TATGTGAAGG AAGGTCACAA ACAGCCTGCA CTAATTTCCC TTTTCTGGTT
13951  TTATGTCTTG GCAGGGGAAA GGACAGGTAG GGTGGGGTTG AGGGGGAGGG
```

FIG. 9E

```
14001  CACACACATC  TACTTGGATA  AATTGCATCT  CCTCTTTCCT  TCACCCCGCC
14051  ACCATATCTT  AAAGCCTTAT  GACATCCTCT  AGGGCAGAAT  TTTCTCACCA
14101  GCTCCCCGCC  CTACCAACTT  CAAAGTGAAC  TTCTAACTAA  CTTGAGGGGC
14151  CAAAGTTCTA  AATAAAACTT  GTTAGAGTTT  AGCGGGCACC  TCAGTCATCA
14201  GGAATGCCTC  CAGGAAAGCA  AAAAGCTTGA  TGTGTGTACA  GCCACGTGGT
14251  GGAGTCCTGC  CACCCTATGA  TTCCTGTCCC  AGTGGTCGTG  TGGGGCCTGA
14301  GATCCTGAAT  TTCTAATGAG  CTCCCAGTAC  GCCCTGACTC  ACTGTGCCAG
14351  AGGACTGCAG  TTTGAGTAGC  AAGGTTGTGT  GACTGTCTTC  GATCATGGCT
14401  ACAGAAGCTG  GCTCAAGTAC  AGCCCTTCGT  GTGTAAAAGC  CATGTGTAAA
14451  TGAGAAGAAA  CAGAAGGCAA  AGCTGCGTTG  CATGGCATCT  GAATCAGTGC
14501  CCTGCAGTTT  TGTTTTTTGT  TTTTTTTTTT  TCAAAGACAT  TCTTTTTCCC
14551  AACAAGATGA  GTGGCAATCT  TATGTTCTAG  CCACTCTTAG  ACATGAAAAC
14601  ACTGGGTTGC  TTATCTTGTA  AAATCTGCTC  TGCTTGCTTG  CTTGGGCACG
14651  CTGCAGTCAG  TTTAGTCAAA  TGCGTGTCAG  TACATCTATA  TGTATGAGGG
14701  AGCAGGTGCA  AGTCCTTAGA  AATGTACTTT  AAAAAACTTG  AACACTTAAG
14751  TCAGTGTGCT  GAGCTGCTCC  TGTGTGATGT  TAGGCCAAGC  ACCTGAGTTA
14801  AAGGGATCTC  TTTGAAGGCA  GAGGGTAGAT  GTCGTATGGT  TGAAGCATTT
14851  GTTTATACTA  AAATGATGCT  TGACTTTTTT  TCTAAGTTAT  AAGACAGTAC
14901  ACTGTATAAG  TTCATTGAAC  CTAGAGGGTG  GCATAGGACT  CCAAATCTGG
14951  TATGGGAGGT  TTGTTCTAAT  GGAAGTTCGA  ATCTTTTTG  CAGTTGGCTT
15001  GGAATAAAGT  GCTTATGTGA  ATGGGCTTAA  GCTAGGGAAA  AAAATGGGTT
15051  TCCCTCTGCA  AAGAGGGTCA  GCACAGAAAT  AACTTCCTGG  CTTTGCTTGC
15101  ATGAATGCCA  CTTGTTAGCA  GATGCCCTGT  GGGGATCCGA  ATTC
```

FIG. 9F

```
   1 GAATTCGCTA GGTAGACCAG GCTGGCCCAG AACACCTAGA GATCATCTGG
  51 CTGCCTCTGT CTCTTGAGTT CTGGGGCTAA AGCATGCACC ACTCTACCTG
 101 GCTAGTTTGT ATCCATCTAA ATTGGGGAAG AAAGAAGTAC AGCTGTCCCC
 151 AGAGATAACA GCTGGGTTTT CCCATCAAAC ACCTAGAAAT CCATTTTAGA
 201 TTCTAAATAG GGTTTGTCAG GTAGCTTAAT TAGAACTTTC AGACTGGGTT
 251 TCACAGACTG GTTGGGCCAA AGGTCACTTT ATTGTCTGGG TTTCAGCAAA
 301 ATGAGACAAT AGCTGTTATT CAAACAACAT TTGGGTAAGG AAGAAAAATG
 351 AACAAACACC ACTCTCCCTC CCCCGCTCC GTGCCTCCAA ATCCATTAAA
 401 GGCAAAGCTG CACCCCTAAG GACAACGAAT CGCTGCTGTT TGTGAGTTTA
 451 AATATTAAGG AACACATTGT GTTAATGATT GGAGCAGCAG TGATTGATGT
 501 AGTGGCATTG GTGAGCACTG AATCCGTCCT TCAACCTGCT ATGGGAGCAC
 551 AGAGCCTGAT GCCCCAGGAG TAATGTAATA GAGTAATGTA ATGTAATGGA
 601 GTTTAATTT TGTGTTGTTG TTTTAAATAA TTAATTGTAA TTTTGGCTGT
 651 GTTAGAAGCT GTGGGTACGT TTCTCAGTCA TCTTTTCGGT CTGGTGTTAT
 701 TGCCATACCT TGATTAATCG GAGATTAAAA GAGAAGGTGT ACTTAGAAAC
 751 GATTTCAAAT GAAAGAAGGT ATGTTTCCAA TGTGACTTCA CTAAAGTGAC
 801 AGTGACGCAG GGAATCAATC GTCTTCTAAT AGAAAGGGCT CATGGAGACC
 851 TGAGCTGAAT CTTTCTGTTC TGGATGAGAG AGGTGGTACC CATTGGAATG
 901 AAAGGACTTA GTCAGGGCA ATACAGTGTG CTCCAAGGCT GGGGATGGTC
 951 AGGATGTTGT GCTCAGCCTC TAACACTCCT TCCAACCTGA CATTCCTTCT
1001 CACCCTTTGT CTCTGGCCAG TAGAATACAG GAACTCGTTC CTGTTTTTTT
1051 TTTTTTAAAT TCTGAAGGTG TGTAAGTACA AAGGTCAGAT GAGCGGCCCT
1101 AGGTCAAGAC TGCTTTGTGG TGACAAGGGA GTATAACACC CACCCCAGAA
1151 ACCAAGAACC GGAAATTGCT ATCTTCCAGC CCTTTGAGAG CTACCTGAAG
1201 CTCTGGGCTG CTGGCCTCAC CCCTTCCCTG CAGCTTTCCC TTTAGCAGAG
1251 GCTGTGATTT CCTTCAGCGC TTGGGCAAAT ACTCTTAGCC TGGCTCACCT
1301 TCCCCATCCT CGTTTGTAAA AACAAAGATG AAGCTGATAG TTCCTTCCCA
1351 GCTCCATCAG AGGCAGGGTG TGAAATTAGC TCCTGTTTGG GAAGGTTTAA
1401 AAGCCGGCCA CATTCCACCT CCCAGCTAGC ATGATTACCA ACTCTTGTTT
1451 CTTACTGTTG TTATGAAAGA CTCAATTCCT CATCTCCCTT TCCCTTCTTT
1501 TAAAAGGGG CCAAAGGGCA CTTTGTTTTT TTCTCTACAT GGCCTAAAAG
1551 GCACTGTGTT ACCTTCCTGG AAGGTCCCAA ACAAACAAAC AAACAAACAA
1601 AATAACCATC TGGCAGTTAA GAAGGCTTCA GAGATATAAA TAGGATTTTC
1651 TAATTGTCTT ACAAGGCCTA GGCTGTTTGC CTGCCAAGTG CCTGCAAACT
1701 ACCTCTGTGC ACTTGAAATG TTAGACCTGG GGGATCGATG GAGGGCACCC
1751 AGTTTAAGGG GGGTTGGTGC AATTCTCAAA TGTCCACAAG AAACATCTCA
1801 CAAAAACTTT TTTGGGGGGA AAGTCACCTC CTAATAGTTG AAGAGGTATC
1851 TCCTTCGGGC ACACAGCCCT GCTCACAGCC TGTTTCAACG TTTGGGAATC
1901 CTTTAACAGT TTACGGAAGG CCACCCTTTA AACCAATCCA ACAGCTCCCT
1951 TCTCCATAAC CTGATTTTAG AGGTGTTTCA TTATCTCTAA TTACTCGGGG
2001 TAAATGGTGA TTACTCAGTG TTTTAATCAT CAGTTTGGGC AGCAGTTATT
2051 CTAAACTCAG GGAAGCCCAG ACTCCATGG GTATTTTGG AAGGTACAGA
2101 GACTAGTTGG TGCATGCTTT CTAGTACCTC TTGCATGTGG TCCCCAGGTG
2151 AGCCCCGGCT GCTTCCCGAG CTGGAGGCAT CGGTCCCAGC CAAGGTGGCA
2201 ACTGAGGGCT GGGGAGCTGT GCAATCTTCC GGACCCGGCC TTGCCAGGCG
2251 AGGCGAGGCC CCGTGGCTGG ATGGGAGGAT GTGGGCGGGG CTCCCCATCC
2301 CAGAAGGGGA GGCGATTAAG GGAGGAGGGA AGAAGGGAGG GGCCGCTGGG
2351 GGGAAAGACT GGGGAGGAAG GAAGAAAGA GAGGGAGGGA AAAGAGAAGG
2401 AAGGAGTAGA TGTGAGAGGG TGGTGCTGAG GGTGGGAAGG CAAGAGCGCG
2451 AGGCCTGGCC CGGAAGCTAG GTGAGTTCGG CATCCGAGCT GAGAGACCCC
2501 AGCCTAAGAC GCCTGCGCTG CAACCCAGCC TGAGTATCTG GTCTCCGTCC
2551 CTGATGGGAT TCTCGTCTAA ACCGTCTTGG AGCCTGCAGC GATCCAGTCT
2601 CTGGCCCTCG ACCAGGTTCA TTGCAGCTTT CTAGAGGTCC CCAGAAGCAG
2651 CTGCTGGCGA GCCCGCTTCT GCAGGAACCA ATGGTGAGCA GGGCAACCTG
2701 GAGAGGGGCG CTATTCTGAG GATTCGAGGT GCACCCGTAG TAGAAGCTGG
2751 GGATGGGGCT CAGGCTGTAA CCGAGGCAAA AGTTGGCCTA TTCCTCCTTC
```

FIG. 10A

```
2801  CTTCTCCAAC  AGTGTTGGAG  GTGGGATGAT  GGAGGCTAAA  AGGCACCTCC
2851  ATATATGTTA  CTGCGTCTAT  CAACCTACTT  TAGGGAGGTG  CGGGCCAGGA
2901  GAGGCGGGAA  GGAGAGAAGG  CCTTGAAGA   GAGGTCATTG  GGAAGAACTG
2951  TGGGGTTTGG  TGGGTTTGCT  TCCACTTAGA  CTATAAGAGT  GGGAGAGGAG
3001  GGAGTCAACT  CTAAGTTTCA  ACACCAGTGG  GGGACTGAGG  ACTGCTTCAT
3051  TAGGAGAGAG  AACCTAGCCA  GAGCTAGCTT  TGCAAAGAG   GCTGTAGTCC
3101  TGCTTTGCTC  TAAAGCGCGA  CCCGGGATAG  AGAGGCTTCC  TTGAGCGGGG
3151  TGTCACCTAA  TCTTGTCCCC  AACGCACCCC  CTCCCAGCCC  CTGAGAGCTA
3201  GCGAACTGTA  GGTACACAAC  TCGCTCCCAT  CTCCAGGAGC  TATTTTCTTA
3251  GACATGGGCA  CCCATGATTC  TGCCTTCTGG  TACTCTCCCC  TCCCTGGGAA
3301  AGGGGTGTAA  GGTTCCGACG  GAACCGTGGC  CAGGATGCCG  AAAGGCTACC
3351  TGTGCGGGTC  TTCTGCCATG  CTGTGTCTGT  GCGGACATGC  CAGCAGGGCT
3401  AATGAGGAGC  TTGCGATACT  CCAAAGGGTT  CGGGAATTGC  GGGGTCCTTA
3451  CACGCAGTGG  AGTTGGGCCC  CTTTTACTCA  GAAGGTTTCC  GCCACGGCTT
3501  TGGTTGATAG  TTTTTTTAGT  ATCCTGGTTT  ATGAACTGAA  GGTTTTGTGA
3551  GATGTTGAAT  CACTAGCAGG  GTCATATTTG  GCAAACCGAG  GCTACTATTA
3601  AATTTTGGTT  TTAGAAGAAG  ATTCTGGGGA  GAAAGTGAAG  GGTAACTGCC
3651  TCCAGGAGCT  GTATCAACCC  CATTAAGAAA  AAAAAAATA   CCAGGAGATG
3701  AAAATTTACT  TTGATCTGTA  TTTTTTAATT  AAAAAAAATC  AGGGAAGAAA
3751  GGAGTGATTA  GAAAGGGATC  CTGAGCGTCG  GCGGTTCCAC  GGTGCCCTCG
3801  CTCCGCGTGC  GCCAGTCGCT  AGCATATCGC  CATCTCTTTC  CCCCTTAAAA
3851  GCAAATAAAC  AAATCAACAA  TAAGCCCTTT  GCCCTTTCCA  GCGCTTTCCC
3901  AGTTATTCCC  AGCGGCGACG  CGTGTCGGGG  AATAGAGAAA  TCGTCTCAGA
3951  AAGCTGCGCT  GATGGTGGTG  AGAGCGGACT  GTCGCTCAGG  GGCGCCCGCG
4001  GTCTCTGCAC  CCAGGGCAGC  AGTGTGGGAT  GGCGCTGGGC  AGCCACCGCC
4051  GCCAGGAAGG  ACGTGACTCT  CCATCCTTTA  CACTTCTTTC  TCAAAGGTTT
4101  CCCGAAAGTG  CCCCCCGCCT  CGAAAACTGG  GGCCGGTGCG  GGGGGGGGGA
4151  GAGGTTAGGT  TGAAAACCAG  CTGGACACGT  CGAGTTCCTA  AGTGAGGCAA
4201  AGAGGCGGGG  TGGAGCGGGC  TCTGGAGCGG  GGGAGTCCTG  GGACTCGGTC
4251  CTCGGATGGA  CCCCGTGCAA  AGACCTGTTG  AACAAGAGT   TGCGCTTCCG
4301  AGGTTAGAAC  AGGCCAGGCA  TCTTAGGATA  GTCAGGTCAC  CCCCCCCCC
4351  AACCCCACCC  GAGTTGTGTT  GGTGAATTTC  TTGGAGGAAT  CTTAGCCGCG
4401  ATTCTGTAGC  TGGTGCAAAA  GGAGGAAAGG  GGTGGGGGAA  GGAAGTGGCT
4451  GTGCGGGGGT  GGCGGTGGGG  GTGGAGGTGG  TTTAAAAAGT  AAGCCAAGCC
4501  AGAGGGAGAG  GTCGAGTGCA  GGCCGAAAGC  TGTTCTCGGG  TTTGTAGACG
4551  CTTGGGATCG  CGCTTGGGGT  CTCCTTTCGT  GCCGGGTAGG  AGTTGTAAAG
4601  CCTTTGCAAC  TCTGAGATCG  TAAAAAAAAT  GTGATGCGCT  CTTTCTTTGG
4651  CGACGCCTGT  TTTGGAATCT  GTCCGGAGTT  AGAAGCTCAG  ACGTCCACCC
4701  CCCACCCCCC  GCCCACCCCC  TCTGCCTTGA  ATGGCACCGC  CGACCGGTTT
4751  CTGAAGGATC  TGCTTGGCTG  GAGCGGACGC  TGAGGTTGGC  AGACACGGTG
4801  TGGGGACTCT  GGCGGGGCTA  CTAGACAGTA  CTTCAGAAGC  CGCTCCTTCT
4851  AACTTTCCCA  CACCGCTCAA  ACCCCGACAC  CCCCGCGGCG  GACTGAGTTG
4901  GCGACGGGGT  CAGAGTCTTC  TGGCTGAAAG  TTAGATCCGC  TAGGGGTCGG
4951  CTGCCTGTCG  CTAGAAGCAT  TATTTGGCCT  CTCGGAGACC  CGTGTGGAGG
5001  AAGTGCTGGA  GTGTGCGAGT  GTGTTTGCGT  GTGTGTGT    GTGTGTGT
5051  GTGTGTGT    GTGTGTGT    GTGCGCGCGC  CCTTGGAGGG  TCCCTATGCG
5101  CTTTCCTTTT  CATGGAACGC  TGTCGTGAGG  CTTTGGTAAA  CTGTCTTTTC
5151  GGTTCCTCTC  TCGGCTGCAC  TTAAGCTTTG  TCGGCGCTGT  AAAGAGACGC
5201  GTCTTCAAGT  GCACCCTGAT  CCTCAGGCTT  CAGATAACCC  GTCCCGAAC
5251  CTGGCCAGAT  GCATTGCACT  GCGCGCCGCA  GGTAGAGACG  TGCCCACGT
5301  CCCTGCGTG   CAGCGACTAC  GACCGAGAGC  CGCGCCAGTG  TGGTGTCCCG
5351  CCGAGAGTTC  CTCAGAGCAG  GCGGGACAA   CTCCCAGACG  GCTGGGGCTC
5401  CAGCTGCGGG  CGCGGAGGTT  GGCCTCGCTC  GCAGGGGCTG  GACCCAGCCG
5451  GGGTGGGAGG  ATGGAGGAGG  GGCGGGCGGG  CTCTTCGGTG  AGTGGGGCGG
5501  GGCCTCTGGG  TCCACGTGAC  TCCTAGGGGC  TGGAAGAAAA  ACAGAGCCTG
5551  TCTGCTCCAG  AGTCTCATTA  TATCAAATAT  CATTTTAGGA  GCCATTCCGT
```

FIG. 10B

```
5601  AGTGCCATTC  GGAGCGACGC  ACTGCCGCAG  CTTCTCTGAG  CCTTTCCAGC
5651  AAGTTTGTTC  AAGATTGGCT  CCCAAGAATC  ATGGACTGTT  ATTATGCCTT
5701  GTTTTCTGTC  AGTGAGTAGA  CACCTCTTCT  TTCCCTTCTT  GGGATTTCAC
5751  TCTGTCCTCC  CATCCCTGAC  CACTGTCTGT  CCCTCCCGTC  GGACTTCCAT
5801  TTCAGTGCCC  CGCGCCCTAC  TCTCAGGCAG  CGCTATGGTT  CTCTTTCTGG
5851  TCCCTGCAAG  GCCAGACACT  CGAAATGTAC  GGGCTCCTTT  TAAAGCGCTC
5901  CCACTGTTTT  CTCTGATCCG  CTGCGTTGCA  AGAAAGAGGG  AGCGCGAGGG
5951  ACCAAATAGA  TGAAAGGTCC  TCAGGTTGGG  GCTGTCCCTT  GAAGGGCTAA
6001  CCACTCCCTT  ACCAGTCCCG  ATATATCCAC  TAGCCTGGGA  AGGCCAGTTC
6051  CTTGCCTCAT  AAAAAAAAAA  AAAAAAACAA  AAAACAAACA  GTCGTTTGGG
6101  AACAAGACTC  TTTAGTGAGC  ATTTTCAACG  CAGCGACCAC  AATGAAATAA
6151  ATCACAAAGT  CACTGGGGCA  GCCCCTTGAC  TCCTTTTCCC  AGTCACTGGA
6201  CCTTGCTGCC  CGGTCCAAGC  CCTGCCGGCA  CAGCTCTGTT  CTCCCCTCCT
6251  CCTGTTCTTA  ACCAGCTGGA  AGTTGTGGAA  ATTGGGCTGG  AGGGCGGAGG
6301  AAGGGCGGGG  GTGGGGGGGT  GGAGAAGGTG  GGGGGGGGGG  AGGCTGAAGG
6351  TCCGAAGTGA  AGAGCGATGG  CATTTAATT   CTCCCTCCNC  CTCCCCCCTT
6401  TACCTCCTCA  ATGTTAACTG  TTTATCCTTG  AAGAAGCCAC  GCTGAGATCA
6451  TGGCTCAGAT  AGCCGTTGGG  ACAGGATGGA  GGCTATCTTA  TTTGGGGTTA
6501  TTTGAGTGTA  AACAAGTTAG  ACCAAGTAAT  TACAGGGCGA  TTCTTACTTT
6551  CGGGCCGTGC  ATGGCTGCAG  CTGGTGTGTG  TGTGTGTAGG  GTGTGAGGGA
6601  GAAAACACAA  ACTTGATCTT  TCGGACCTGT  TTTACATCTT  GACCGTCGGT
6651  TGCTACCCCT  ATATGCATAT  GCAGAGACAT  CTCTATTTCT  CGCTATTGAT
6701  CGGTGTTTAT  TTATTCTTTA  ACCTTCCACC  CCAACCCCCT  CCCCAGAGAC
6751  ACCATGATTC  CTGGTAACCG  AATGCTGATG  GTCGTTTTAT  TATGCCAAGT
6801  CCTGCTAGGA  GGCGCGAGCC  ATGCTAGTTT  GATACCTGAG  ACCGGGAAGA
6851  AAAAAGTCGC  CGAGATTCAG  GGCCACGCGG  GAGGACGCCG  CTCAGGGCAG
6901  AGCCATGAGC  TCCTGCGGGA  CTTCGAGGCG  ACACTTCTAC  AGATGTTTGG
6951  GCTGCGCCGC  CGTCCGCAGC  CTAGCAAGAG  CGCCGTCATT  CCGGATTACA
7001  TGAGGGATCT  TTACCGGCTC  CAGTCTGGGG  AGGAGGAGGA  GGAAGAGCAG
7051  AGCCAGGGAA  CCGGGCTTGA  GTACCCGGAG  CGTCCCGCCA  GCCGAGCCAA
7101  CACTGTGAGG  AGTTTCCATC  ACGAAGGTCA  GTTTCTGCTC  TTAGTCCTGG
7151  CGGTGTAGGG  TGGGGTAGAG  CRCCGGGCA   GAGGGTGGGG  GGTGGGCAGC
7201  TGGCAGGGCA  AGCTGAAGGG  GTTGTGGAAG  CCCCCGGGGA  AGAAGAGTTC
7251  ATGTTACATC  AAAGCTCCGA  GTCCTGGAGA  CTGTGGAACA  GGGCCTCTTA
7301  CCTTCAACTT  TCCAGAGCTG  CCTCTGAGGG  TACTTTCTGG  AGACCAAGTA
7351  GTGGTGGTGA  TGGGGAGGG   GGTTACTTTG  GGAGAAGCGG  ACTGACACCA
7401  CTCAGACTTC  TGCTACCTCC  CAGTGGGTGT  TCTTTAGCTA  TACCAAAGTC
7451  AGGGATTCTG  CCCGTTTTGT  TCCAAAGCAC  CTACTGAATT  TAATATTACA
7501  TCTGTGTGTT  TGTCAGGTTT  ATCAATAGGG  GCCTTGTAAT  ACGATCTGAA
7551  TGTTTCCTAG  CGGATGTTTC  TTTTCCAAAG  TAAATCTGAG  TTATTAATCC
7601  TCCAGCATCA  TTACTGTGTT  GGAATTTATT  TTCCCTTCTG  TAACATGATC
7651  AACAAGGCGT  GCTCTGTGTT  TCTAGGATCG  CTGGGAAAT   GTTTGGTAAC
7701  ATACTCAAAA  GTGGAGAGGG  AGAGAGGGTG  GCCCCTCTTT  TTCTTTACAA
7751  CCACTTGTAA  AGAAAACTGT  ACACAAAGCC  AAGAGGGGGC  TTTAAAGGG
7801  GAGTCCAAGG  GTGGTGGAGT  AAAAGAGTTG  ACACATGGAA  ATTATTAGGC
7851  ATATAAAGGA  GGTTGGGAGA  TACTTTCTGT  CTTTGGTGTT  TGACAAATGT
7901  GAGCTAAGTT  TTGCTGGTTT  GCTAGCTGCT  CCACAACTCT  GCTCCTTCAA
7951  ATTAAAAGGC  ACAGTAATTT  CCTCCCCTTA  GGTTTCTACT  ATATAAGCAG
8001  AATTCAACCA  ATTCTGCTAT  TTTTGTTTT   TGTTTCTTGT  TTTGTTTTG
8051  TTTGGTTTTT  TTTTTTTTT   TTTTTTTTTT  GTCTCAGAAA  AGCTCATGGG
8101  CCTTTTCTTT  TCCCCTTTCA  ACTGTGCCTA  GAACATCTGG  AGAACATCCC
8151  AGGGACCAGT  GAGAGCTCTG  CTTTTCGTTT  CCTCTTCAAC  CTCAGCAGCA
8201  TCCCAGAAAA  TGAGGTGATC  TCCTCGGCAG  AGTCCGGCT   CTTTCGGGAG
8251  CAGGTGGACC  AGGGCCCTGA  CTGGGAACAG  GCTTCCACC   GTATAAACAT
8301  TTATGAGGTT  ATGAAGCCCC  CAGCAGAAAT  GGTTCCTGGA  CACCTCATCA
8351  CACGACTACT  GGACACCAGA  CTAGTCCATC  ACAATGTGAC  ACGGTGGGAA
```

FIG. 10C

```
8401  ACTTTCGATG  TGAGCCCTGC  AGTCCTTCGC  TGGACCCGGG  AAAAGCAACC
8451  CAATTATGGG  CTGGCCATTG  AGGTGACTCA  CCTCCACCAG  ACACGGACCC
8501  ACCAGGGCCA  GCATGTCAGA  ATCAGCCGAT  CGTTACCTCA  AGGGAGTGGA
8551  GATTGGGCCC  AACTCCGCCC  CCTCCTGGTC  ACTTTTGGCC  ATGATGGCCG
8601  GGGCCATACC  TTGACCCGCA  GGAGGGCCAA  ACGTAGTCCC  AAGCATCACC
8651  CACAGCGGTC  CAGGAAGAAG  AATAAGAACT  GCCGTCGCCA  TTCACTATAC
8701  GTGGACTTCA  GTGACGTGGG  CTGGAATGAT  TGGATTGTGG  CCCCACCCGG
8751  CTACCAGGCC  TTCTACTGCC  ATGGGGACTG  TCCCTTTCCA  CTGGCTGATC
8801  ACCTCAACTC  AACCAACCAT  GCCATTGTGC  AGACCCTAGT  CAACTCTGTT
8851  AATTCTAGTA  TCCCTAAGGC  CTGTTGTGTC  CCCACTGAAC  TGAGTGCCAT
8901  TTCCATGTTG  TACCTGGATG  AGTATGACAA  GGTGGTGTTG  AAAAATTATC
8951  AGGAGATGGT  GGTAGAGGGG  TGTGGATGCC  GCTGAGATCA  GACAGTCCGG
9001  AGGGCGGACA  CACACACACA  CACACACACA  CACACACACA  CACACACACA
9051  CACGTTCCCA  TTCAACCACC  TACACATACC  ACACAAACTG  CTTCCCTATA
9101  GCTGGACTTT  TATCTTAAAA  AAAAAAAAAA  GAAAGAAAGA  AAGAAAGAAA
9151  GAAAAAAAAT  GAAAGACAGA  AAAGAAAAAA  AAAACCCTAA  ACAACTCACC
9201  TTGACCTTAT  TTATGACTTT  ACGTGCAAAT  GTTTTGACCA  TATTGATCAT
9251  ATTTTGACAA  ATATATTTAT  AACTACATAT  TAAAAGAAAA  TAAAATGAG
```

METHODS AND COMPOSITIONS FOR IDENTIFYING OSTEOGENIC AGENTS

TECHNICAL FIELD

The present invention relates to assay techniques for identifying agents which modulate bone growth.

BACKGROUND OF THE INVENTION

Although there is a great deal of information available on the factors which influence the breakdown and resorption of bone, information on growth factors which stimulate the formation of new bone is more limited. Investigators have searched for sources of such activities and have found that bone tissue itself is a storehouse for factors which have the capacity for stimulating bone cells. Thus, extracts of bovine tissue obtained from slaughterhouses contain not only structural proteins which are responsible for maintaining the structural integrity of bone, but also biologically active bone growth factors which can stimulate bone cells to proliferate. Among these latter factors are transforming growth factor β, the heparin-binding growth factors (acidic and basic fibroblast growth factor), the insulin-like growth factors (insulin-like growth factor I and insulin-like growth factor II) and a recently described family of proteins called bone morphogenetic proteins (BMPs). All of these growth factors have effects on other types of cells as well as on bone cells.

The BMPs are novel factors in the extended transforming growth factor β family. They were first identified in extracts of demineralized bone (Urist 1965, Wozney et al., 1988). Recombinant BMP-2 and BMP-4 can induce new bone formation when they are injected locally into the subcutaneous tissues of rats (Wozney 1992, Wozney & Rosen 1993). These factors are expressed by normal osteoblasts as they differentiate, and have been shown to stimulate osteoblast differentiation and bone nodule formation in vitro as well as bone formation in vivo (Harris et al., 1994). This latter property suggests potential usefulness as therapeutic agents in diseases which result in bone loss.

The cells which are responsible for forming bone are osteoblasts. As osteoblasts differentiate from precursors to mature bone-forming cells, they express and secrete a number of the structural proteins of the bone matrix including Type-1 collagen, osteocalcin, osteopontin and alkaline phosphatase (Stein et al, 1990, Harris et al, 1994). They also synthesize a number of growth regulatory peptides which are stored in the bone matrix and are presumably responsible for normal bone formation. These growth regulatory peptides include the BMPs (Harris et al, 1994). In studies of primary cultures of fetal rat calvarial osteoblasts, BMPs 1, 2, 3, 4, and 6 are expressed by cultured cells prior to the formation of mineralized bone nodules (Harris et al, 1994). Expression of the BMPs coincides with expression of alkaline phosphatase, osteocalcin and osteopontin.

Although the BMPs have powerful effects to stimulate bone formation in vitro and in vivo, there are disadvantages to their use as therapeutic agents to enhance bone healing. Receptors for the bone morphogenetic proteins have been identified in many tissues, and the BMPs themselves are expressed in a large variety of tissues in specific temporal and spatial patterns. This suggests that they may have effects on many tissues other than bone, potentially limiting their usefulness as therapeutic agents when administered systemically. Moreover, since they are peptides, they would have to be administered by injection. These disadvantages are severe limitations to the development of BMPs as therapeutic agents.

It is an object of the present invention to overcome the limitations inherent in known osteogenic agents by providing a method to identify potential drugs which would stimulate production of BMPs locally in bone.

PRIOR ART

Sequence data on small fragments of the 5'-flanking region of the BMP-4 gene have been published (Chen et al, 1993; Kurihara et al, 1993), but the promoter has not been previously functionally identified or isolated.

DISCLOSURE OF THE INVENTION

A cell-based assay technique for identifying and evaluating compounds which stimulate the growth of bone is provided, comprising culturing a host cell line comprising an expression vector comprising a DNA sequence encoding a promoter region of at least one bone morphogenetic protein, operatively linked to a reporter gene encoding an assayable product under conditions which permit expression of said assayable product, contacting the cultured cell line with at least one compound suspected of possessing osteogenic activity, and identifying osteogenic agents by their ability to modulate the expression of the reporter gene and thereby increase the production of the assayable product.

This assay technique specifically identifies osteogenic agents which stimulate bone cells to produce bone growth factors in the bone morphogenetic protein family. These osteogenic agents display the capacity to increase the activity of the promoters of genes of members of the BMP family and other bone growth factors normally produced by e.g. bone cells.

Also provided in accordance with the present invention are isolated DNA sequences encoding a promoter region of at least one bone morphogenetic protein, and a system for identifying osteogenic agents comprising an expression vector comprising such promoter sequences operatively linked to a reporter gene encoding an assayable product, and means for detecting the assayable product produced in response to exposure to an osteogenic compound.

BRIEF DESCRIPTION OF THE DRAWINGS

FIG. 1B depicts the DNA sequence of selected portions of mouse genomic BMP-4 (SEQ. ID NO. 1) and the predicted amino acid sequences of the identified coding exons (SEQ. ID NO. 2). The numbers on the right show the position of the nucleotide sequence and the bold numbers indicate the location of the amino acid sequence of the coding region. Most of the coding sequence is in exon 4. The end of the transcription unit was estimated based on a 1.8 kb transcript. Primer 1 in exon 1A was used in RT-PCR analysis with Primer 3 in exon 3. Primer 2 in exon 1B was used in RT-PCR analysis with Primer 3. Primer B1 and B2 were used in primer extension reactions;

FIG. 1C portrays the sequence of the BMP-4 exon 1A 5'-flanking region and potential response elements in the mouse BMP-4 1A promoter (SEQ. ID NO. 3). The sequences of 2688 bp of the mouse BMP-4 gene are shown. Nucleotides are numbered on the left with +1 corresponding to the major transcription start site of the 1A promoter. The response elements of DR-1A Proximal and DR-1A Distal oligonucleotides are indicated. The other potential response DNA elements in the boxes are p53, RB (retinoblastoma), SP-1, AP-1, and AP-2. Primer A, indicated by the line above the DNA sequence at +114 to +96, was used for primer extension analysis of exon 1A-containing transcripts;

FIG. 5 portrays the nucleotide sequence of the mouse BMP-2 gene 5'-flanking region from −2736 to +139 (SEQ. ID NO. 4). The transcription start site is denoted by +1;

FIG. 9A–F depicts the DNA sequence of the mouse BMP-2 promoter and gene (SEQ. ID NO. 6); and FIG. 10A–D depicts the DNA sequence of the mouse BMP-4 promoter and gene (SEQ. ID NO. 7).

DETAILED DESCRIPTION OF THE PREFERRED EMBODIMENTS

Figure 1A:
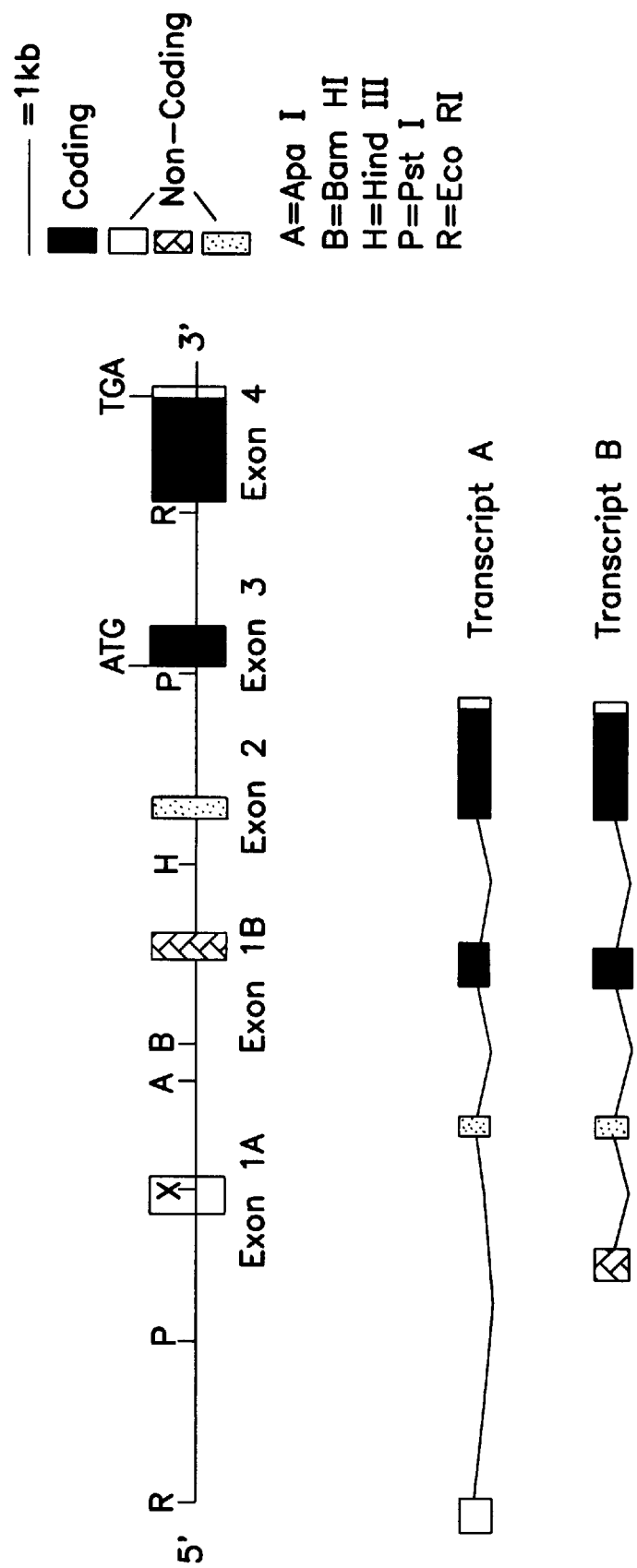
FIG. 1A graphically depicts a restriction enzyme map of mouse genomic BMP-4 and a diagram of two transcripts. The mouse BMP-4 gene transcription unit is ~7 kb and contains 2 coding exons (closed boxes) and 3 non-coding exons, labeled exons 1A, 1B and 2. This 19 kb clone has an ~6 kb 5'-flanking region and an ~7 kb 3'-flanking region. The diagram shows approximately 2.4 kb of the 5'-flanking region, and a small region of the 3'-flanking region. The lower panel shows two alternative transcripts of BMP-4. Both have the same exons 2, 3 and 4 but a different exon 1. Transcript A has exon 1A and transcript B has exon 1B whose size was estimated according to RT-PCR and primer extension analysis in FRC cells.

A cell-based assay technique for identifying and evaluating compounds which stimulate the growth of bone is provided, comprising culturing a host cell line comprising an expression vector comprising a DNA sequence encoding a promoter region of at least one bone morphogenetic protein operatively linked to a reporter gene encoding an assayable product under conditions which permit expression of said assayable product, contacting the cultured cell line with at least one compound suspected of possessing osteogenic activity, and identifying osteogenic agents by their ability to modulate the expression of the reporter gene and thereby increase the production of the assayable product.

The present invention is distinguished from other techniques for identifying bone-active compounds, as it specifically identifies chemical compounds, agents, factors or other substances which stimulate bone cells to produce the bone growth factors in the bone morphogenetic protein (BMP) family (hereinafter "osteogenic agents"). These osteogenic agents are identified by their capacity to increase the activity of the promoters of genes of members of the BMP family and other bone growth factors which are normally produced by bone cells, and other cells including cartilage cells, tumor cells and prostatic cells. When patients are treated with such chemical compounds, the relevant BMP will be produced by bone cells and then be available locally in bone to enhance bone growth or bone healing. Such compounds identified by this assay technique will be used for the treatment of osteoporosis, segmental bone defects, fracture repair, prosthesis fixation or any disease associated with bone loss.

Compounds that inhibit bone morphogenetic protein expression in bone or cartilage may also be useful in clinical situations of excess bone formation which occurs in such diseases as osteoblastic metastases or osteosclerosis of any cause. Such compounds can also be identified in accordance with the present invention.

Also provided in accordance with the present invention are isolated DNA sequences encoding a promoter region of at least one bone morphogenetic protein, and a system for identifying osteogenic agents comprising an expression vector comprising such promoter sequences operatively linked to a reporter gene encoding an assayable product, and means for detecting the assayable product produced in response to exposure to an osteogenic compound.

The promoters of the genes for BMP-4 and BMP-2 are complex promoters which can be linked to reporter genes, such as e.g. the firefly luciferase gene. When these hybrid genes (for example, bone cell BMP-4 promoter or bone cell BMP-2 promoter and firefly luciferase, chloramphenicol acetyl transferase (CAT) cDNAs, or cDNA's for other reporter genes such as β-galactosidase, green fluorescent protein, human growth hormone, alkaline phosphatase, β-glucuronidase, and the like) are transfected into bone cells, osteogenic agents which activate the BMP-4 or BMP-2 promoters can be identified by their capacity in vitro to increase luciferase activity in cell lysates after cell culture with the agent.

Sequence data on small fragments of the 5'-flanking region of the BMP-4 gene have been published (Chen et al, 1993; Kurihara et al, 1993), but the promoter has not been previously identified or isolated, and methods for regulating transcription have not been shown. The present invention isolates the promoters for the BMP genes and utilizes these promoters in cultured bone cells so that agents could be identified which specifically increase BMP-2 or BMP-4 production locally in bone. Since it is known that the BMPs are produced by bone cells, a method for enhancing their production specifically in bone should avoid systemic toxicity. This benefit is obtained by utilizing the unique tissue specific promoters for the BMPs which are provided herein, and then using these gene promoters to identify agents which enhance their activity in bone cells.

By utilizing the disclosure provided herein, other promoters can be obtained from additional bone morphogenetic proteins such as BMP-3, BMP-5, BMP-6, and BMP-7, to provide comparable benefits to the promoters herein specifically described.

In addition, the present invention contemplates the use of promoters from additional growth factors in osteoblastic cells. Included are additional bone morphogenetic proteins, as well as fibroblast growth factors (e.g. FGF-1, FGF-2, and FGF-7), transforming growth factors β-1, β-2, and β-3, insulin-like growth factor-1, insulin-like growth factor-2, platelet-derived growth factor, and the like. Such promoters will readily be utilized in the present invention to provide comparable benefits.

The cells which can be utilized in the present invention include primary cultures of fetal rat calvarial osteoblasts, established bone cell lines available commercially (MC3T3-E1 cells, MG-63 cells, U2OS cells, UMR106 cells, ROS 17/2.8 cells, SaOS2 cells, and the like as provided in the catalog from the American Type Culture Collection (ATCC)), and bone cell lines established from transgenic mice, as well as other cell lines capable of serving as hosts for the present vectors and systems. In addition, a number of tumor cell lines also express BMPs, including the prostate cancer cell lines PC3, LNCAP, and DUI145, as well as the human cancer cell line HeLa. Thus, any of a number of cell lines will find use in the present invention and the choice of an appropriate cell line will be a matter of choice for a particular embodiment.

The following examples serve to illustrate certain preferred embodiments and aspects of the present invention and are not to be construed as limiting the scope thereof.

EXPERIMENTAL

In the experimental disclosure which follows, the following abbreviations apply: eq (equivalents); M (Molar); mM (millimolar); μM (micromolar); N (Normal); mol (moles); mmol (millimoles); μmol (micromoles); nmol (nanomoles); kg (kilograms); gm (grams); mg (milligrams); μg (micrograms); ng (nanograms); L (liters); ml (milliliters); μl (microliters); vol (volumes); and °C. (degrees Centigrade).

EXAMPLE 1

Description and Characterization of Murine BMP-4 Gene Promoter (a) Library Screening, Cloning and Sequencing of Gene A mouse genomic lambda fix II spleen library (Stratagene, La Jolla, Calif.) was screened with a mouse embryo BMP-4 cDNA kindly provided by Dr. B. L. M. Hogan (Vanderbilt University School of Medicine, Nashville, Tenn.). The probe was labeled with [α-$^{32}$P] dCTP using a random-primer labeling kit from Boehringer-Mannheim (Indianapolis, Ind.). Plaque lift filters were hybridized overnight in 6× SSC, 5× Denhardt's, 0.5% SDS containing 200μg/ml sonicated salmon sperm DNA, 10 μg/ml Poly A and 10 μg/ml t-RNA at 68° C. The filters were washed at 55° C. for 20 min, twice in 2× SSC, 0.1% SDS buffer, once in 0.5× SSC, 0.1% SDS. The isolated phage DNA clones were analyzed according to standard procedures (Sambrook et al., 1989).

Fragments from positive clones were subcloned into pBluescript vectors (Stratagene, La Jolla, Calif.) and sequenced in both directions using the Sequenase dideoxynucleotide chain termination sequencing kit (U.S. Biochemical Corp., Cleveland, Ohio).

Three clones were isolated from 2×10$^6$ plaques of mouse spleen 129 genomic library using full length coding region mouse embryo BMP-4 cDNA probe (B. Hogan, Vanderbilt University, Nashville, Tenn). One 19 kb clone contained 5 exons and ~6 kb 5'-flanking region and a ~7 kb 3'-flanking region, as shown in FIG. 1A. The 7 kb transcription unit and the 5'-flanking region of the mouse BMP-4 gene were sequenced (FIG. 10).

Figure 1B-1:
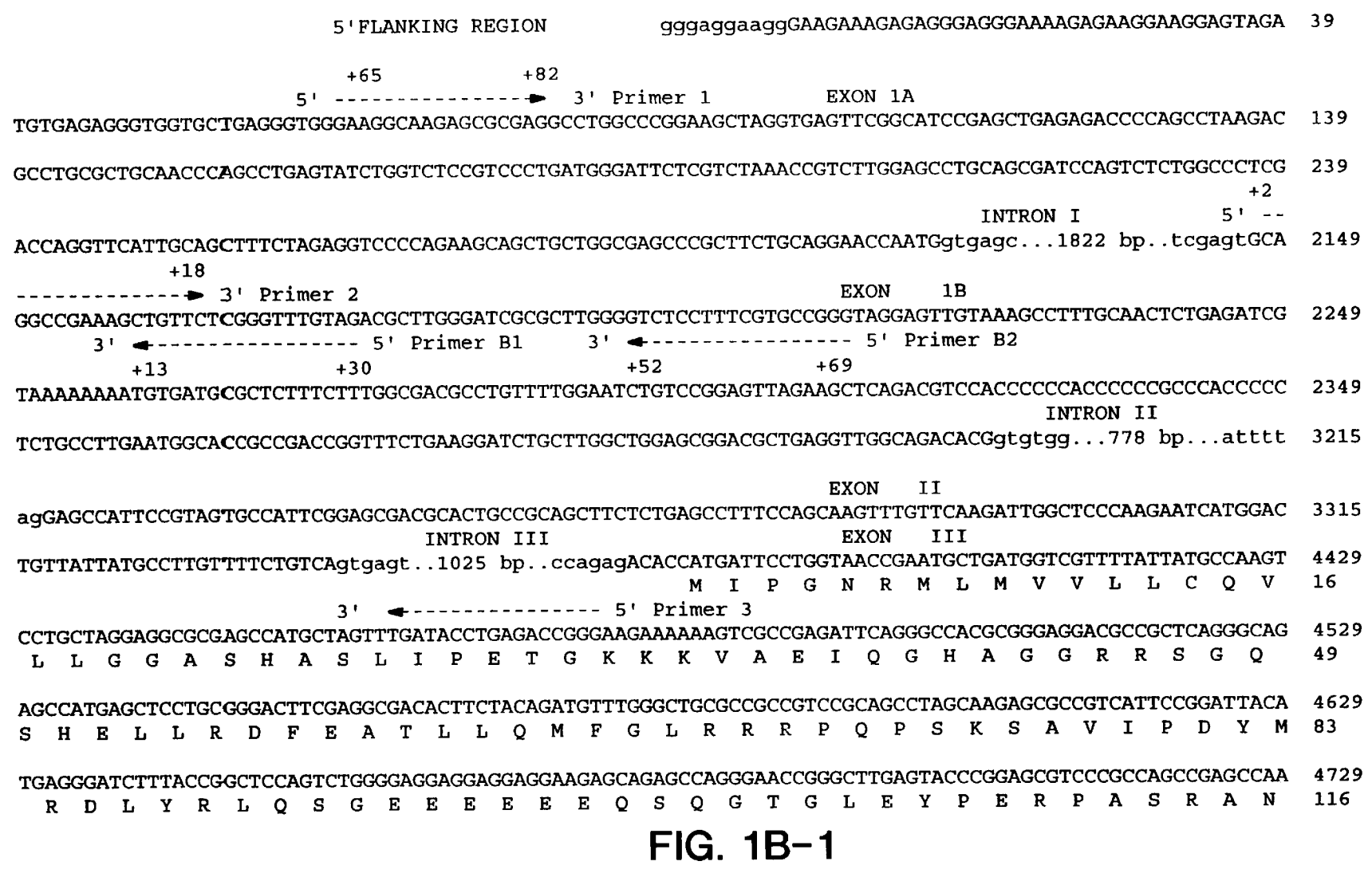

The nucleotide sequence of selected portions of mouse BMP-4 and the deduced amino acid sequence of the coding exons (408 residues; SEQ. ID NO. 2) is shown in FIG. 1B. Primers used in the RT-PCR experiments described below are indicated in this Figure.

FIG. 1C shows the DNA sequence of 2372 bp of the 5'-flanking region and the candidate DNA response elements upstream of exon 1A. Primers used in primer extensions are also shown in FIGS. 1B and 1C.

(b) Primer Extension Mapping of the Transcriptional Start-Site of the Mouse BMP-4 Gene The transcriptional start-sites were mapped by primer extension using the synthetic oligonucleotide primer A 5'-CGGATGCCGAACTCACCTA-3' (SEQ. ID NO. 8), corresponding to the complement of nucleotides +114 to +96 in the exon 1A sequence and the oligonucleotide primer B1 5'-CTACAAACCCGAGAACAG-3' (SEQ. ID NO. 9), corresponding to the complement of nucleotides +30 to +13 of the exon 1B sequence. Total RNA from fetal rat calvarial (FRC) cells and 9.5 day mouse embryo (gift of B. Hogan, Vanderbilt University) was used with both primers. The primer extension assay was carried out using the primer extension kit from Promega (Madison, Wis.). The annealing reactions were, however, carried out at 60° C. in a water bath for 1 hr. The products were then electrophoresed on 8% denaturing-urea polyacrylamide gels and autoradiographed.

One additional oligonucleotide primer B2 5'-CCCGGCACGAAAGGAGAC-3' (SEQ. ID NO. 10), corresponding to the complement of nucleotide sequence +69 to +52 of exon 1B, was also utilized in primer extension reactions with FRC and mouse embryo RNAs.

1. Evidence for utilization of two alternate exon 1 sequences for the BMP-4 gene Several BMP-4 cDNAs were sequenced from prostate cancer cell line PC-3 and from primary FRC cells. Four independent FRC cell BMP-4 cDNAs all contained exon 1A. However, the human prostate carcinoma cell line (PC-3) cDNA contained an apparently unique exon 1B sequence spliced to exon 2 (Chen et al, 1993). A double-stranded oligonucleotide probe (70 bp) to exon 1B was synthesized based on the human PC-3 exon 1B sequence. This exon 1B probe was then used to identify the exon 1B region in the mouse genomic BMP-4 clone. The candidate exon 1B is 1696 bp downstream from the 3' end of exon 1A.

2. Primer extension analysis

Figure 2:
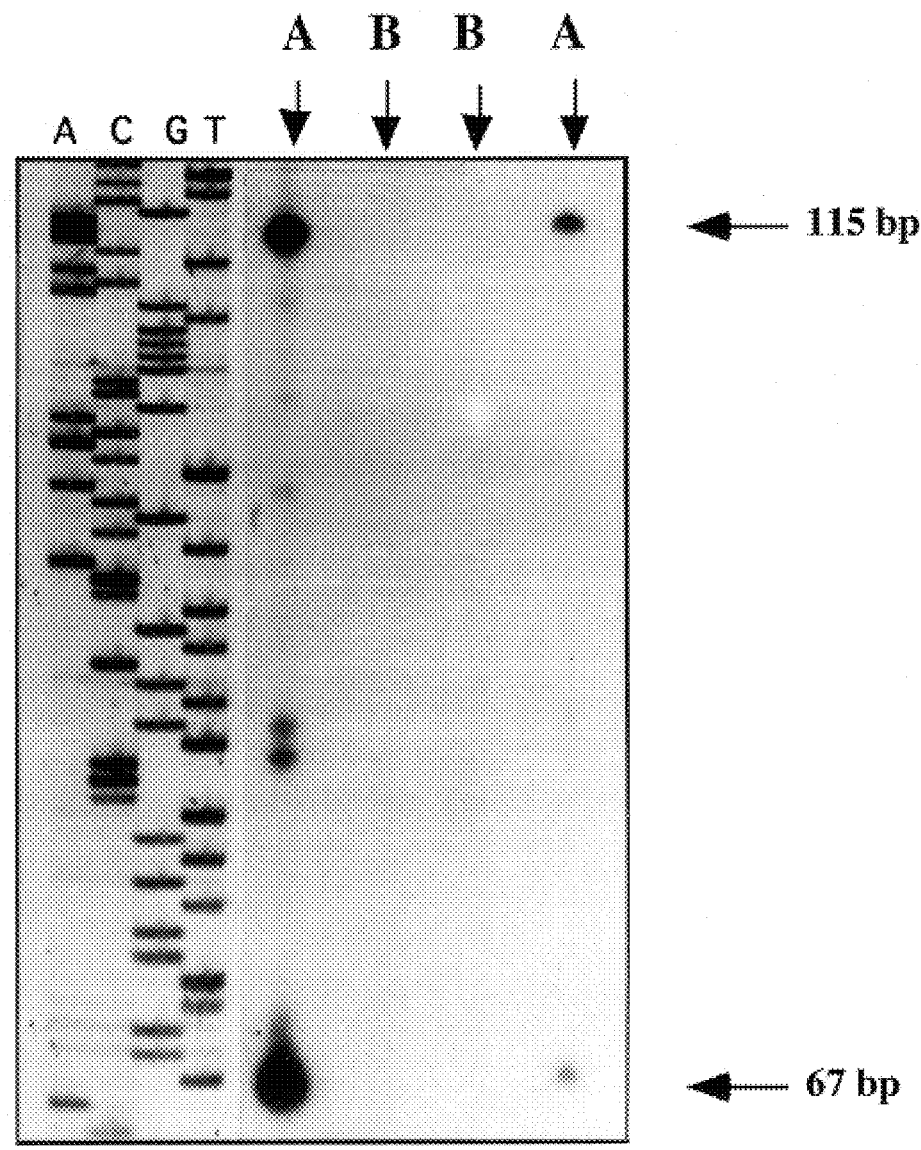
FIG. 2 depicts the results of a primer extension assay. Total RNAs prepared from FRC cells (on the left frame) and mouse embryo 9.5 days (on the right) were used with primer A or the complement of primer 2. Two major extended fragments, 67 and 115 bp, indicated in lane A were obtained from primer A. Two 1B primers, primer B1 and primer B2, also gave negative results with both FRC and mouse embryo total RNA as template. Transcript B is not detectable with this assay. By RT-PCR, transcript B can be detected and quantified.
Figure 2:
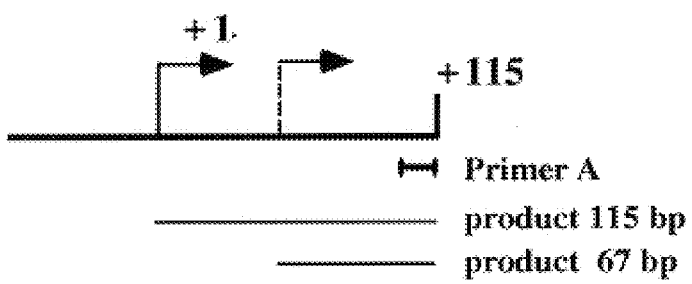

Primer extension analysis was performed to map the mouse BMP-4 gene transcription start sites. Primer A, an oligonucleotide from exon 1A, was used and two oligonucleotides from exon 1B. Total RNA was utilized both from mouse embryo and FRC cells. As shown in FIG. 2, a major extended fragment from primer A was obtained in both mouse embryo and FRC cell total RNAs, which migrates at 115 bp. The extended 5'-end of the 115 bp fragment represents the major transcription start site for 1A-containing transcripts. The size of this 5' non-coding exon 1A is 306 bp. A major extended fragment from the complement of primer B1 (exon 1B) was not detected using both mouse embryo and FRC cell total RNAs. One other primer from exon 1B also gave negative results, suggesting that in 9.5 day mouse embryo and FRC cells, the exon 1B-containing transcripts were not detectable, which suggests that transcripts containing exon 1B are less abundant in these cells and tissues than transcripts containing exon 1A. All primer extensions were carried out after annealing of primers at high stringency. Lower stringency annealing with 1B primers gave extended products not associated with BMP-4 mRNA.

(c) BMP-4 Gene 5' Flanking Region for Exon 1A and 1B Transcripts

Four FRC BMP-4 cDNA were sequenced and found to contain exon 1A sequences spliced to exon 2. The human U2OS BMP-4 cDNA sequence also contains exon 1A (Wozney et al, 1988). This suggests the BMP-4 gene sequences upstream of exon 1A are used primarily in bone cells.

To test whether the BMP-4 1B promoter is utilized at all in FRC cells, oligonucleotide primers were designed to ascertain whether spliced 1B-2-3 exon products and 1A-2-3 exon (control) products could be obtained by a more sensitive RT-PCR technique using FRC poly(A$^+$)-RNA. The 3' primer was in exon 3 (FIG. 1B—primer 3) and the 5' primers were either in exon 1A (primer 1) or exon 1B (primer 2).

Figure 3A:
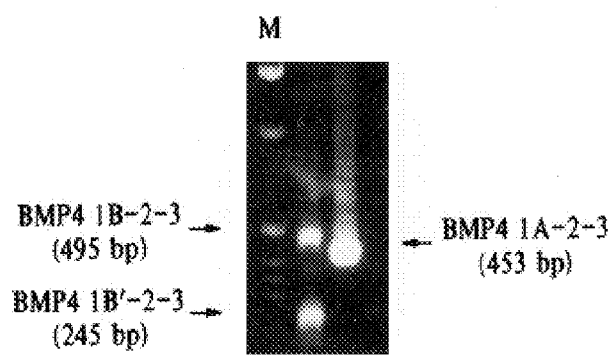
FIG. 3A is a photographic representation of gel electrophoresis of 1A-3 and 1B-3 RT-PCR products of the BMP-4 gene. RT-PCR was performed with two pairs of primers using FRC cell poly A$^+$ mRNA as the template. The products were verified by the DNA sequence.
Figure 3B:
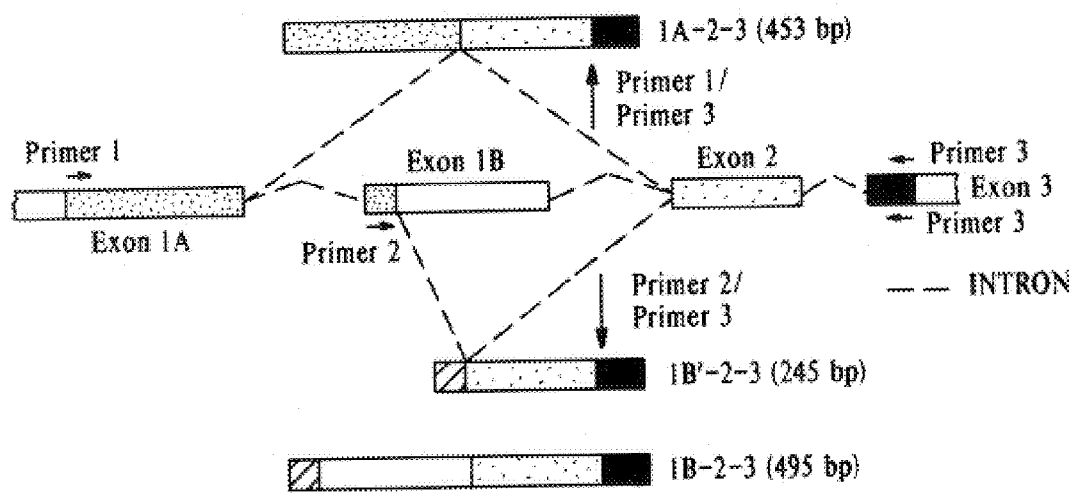
FIG. 3B is a schematic diagram of spliced BMP-4 RT-PCR products with 1A and 1B exons in FRC cells. RT-PCR was performed with two pairs of primers using FRC cell poly A$^+$ mRNA as the template. The diagram shows where the primers are located in the BMP-4 genomic DNA. RT-PCR product 1A-2-3 which contains exon 1A, exon 2 and the 5' region of exon 3, was produced with primer 1 and primer 3. Primer 2 and primer 3 generated two RT-PCR products with the exon 1B-2-3 pattern. The heterogeneity in size of exon 1B is indicated. The 1A promoter is predominantly utilized in bone cells.

The RT-PCR products were cloned and sequenced. A photograph and diagram of the products obtained are presented in FIG. 3A and B. Both 1A-2-3 and 1B-2-3 products were obtained. The results indicate FRC osteoblasts produce transcripts with either a 1A exon or a 1B exon, but not both. This suggests that the intron region between 1A and 1B exons could contain regulatory response elements under certain conditions. Of the 1B-2-3 RT-PCR products obtained from FRC osteoblasts, two products were obtained with different 3' splice sites for the exon 1B. By comparison with the genomic DNA, both 3' ends of the two exon 1Bs have reasonable 5' splice consensus sequences, consistent with an alternate splicing pattern obtained for the 1B-2-3 RT-PCR products. Most importantly, no 1A-1B-2-3 RT-PCR splice products of the BMP-4 gene were obtained. Thus, 1B does not appear to be an alternatively spliced 5'-non-coding exon. By quantitative RT-PCR, it was shown that 1A transcripts are 10 to 15× more abundant in primary bone cells.

The technique of performing RT-PCR will be described. First-strand cDNA was synthesized from 10 μg FRC cell poly(A+)-RNA with an 18 mer dT primer using Superscript™ reverse transcriptase (Gibco BRL) in a total volume of 20 μl. The cDNA was then used as a template for PCR with two sets of synthesized primers. As shown in FIG. 1B, primer 1 (5'-GAAGGCAAGAGCGCGAGG-3') (SEQ. ID NO.11), corresponding to a 3' region of exon 1A and primer 3 (5'-CCCGGTCTCAGGTATCA-3') (SEQ. ID NO. 12), corresponding to a 5' region of exon 3 were used to generate exon 1A-2-3 spliced PCR product. Primer 2 (5'-CAGGCCGAAAGCTGTTC-3') (SEQ. ID NO. 13), corresponding to a 3' region (+2 to +18) of exon 1B, and primer 3 were used to generate exon 1B-2-3 spliced PCR products. GeneAmp PCR kit was used according to the manufacturer's procedure (Perkin-Elmer/Cetus, Norwalk, Conn.). Each cycle consisted of a denaturation step (94° C. for 1 min), an annealing step (59° C. for 2 min) and an elongation step (72° C. for 1 min). The PCR products were analysed by agarose gel electrophoresis for size determination. The products were subcloned into pCR II vector using TA cloning kit (InVitrogen, San Diego, Calif.). The inserts were sequenced in both directions with a sequencing kit from U.S. Biochemical (Cleveland, Ohio).

Northern analysis demonstrated that the single 1.8 kb BMP-4 transcript detected in FRC cells during bone cell differentiation hybridizes to both a pure 1A exon probe and a 2–4 exons probe. The ratio of the 1A to 2-4 signal is constant through the changing levels of BMP-4 expression during differentiation. Using a 1B exon probe no detectable hybridization to the BMP-4 exon 2-4 1.8 kb signal was observed. This again indicates that 1A containing transcripts predominate in bone cells, although 1B transcripts can be detected by the more sensitive PCR method. By quantitative PCR it was shown that 1A transcripts are 10–15× more abundant than 1B in FRC cells.

(d) BMP-4 Promoter 1A Plasmid Construction and Transfection, and Detection of Promoter Activity in Osteoblasts Three BMP-4 1A promoter/plasmids were constructed by excising fragments from the 5' flanking region of the mouse BMP-4 gene and cloning into pBL3CAT expression vectors (Luckow and Schutz, 1987). The pCAT-2.6 plasmid was the pBLCAT3 vector with a 2.6 kb EcoR1 and Xba I fragment (−2372/+258) of the BMP-4 gene. The pCAT-1.3 plasmid was similarly generated from a 1.3 kb Pst fragment (−1144/+212). The pCAT-0.5 plasmid was made from a 0.5 kb SphI and Pst fragment (−260/+212). Both the pCAT-1.3 and the pCAT-0.5 plasmids have 212 bp of exon 1A non-coding region. An additional promoter/plasmid was created from a PCR amplified product, corresponding to the 240 bp sequence between nucleotides −25 and +212, and referred to as the pCAT-0.24. The amplified fragment was first cloned into pCR II vector using TA cloning kit (InVitrogen, San Diego, Calif.) and then the fragment was released with Hind III and Xho I, and religated into pBL3CAT. Correct orientation of all inserts with respect to the CAT vector was verified by DNA sequencing.

The cells used for transient transfection studies were isolated from 19 day-old fetal rat calvariae by sequential digestion with trypsin and collagenase, as described by Bellows et al, (1986) and Harris et al, (1994). In brief, the calvarial bone were surgically removed and cleaned by washing in α minimal essential media (αMEM) containing 10% V/V fetal calf serum (FCS) and antibiotics. The bones were minced with scissors and were transferred to 35 mm tissue culture dish containing 5 ml of sterile bacterial collagenase (0.1%) and trypsin (0.05%). This was then incubated at 37° C. for 20 min. The cells released at this time were collected and immediately mixed with an equal volume of FCS to inactivate trypsin. This procedure is repeated 6 times to release cells at 20 min intervals. Cells released from 3rd, 4th, 5th and 6th digestion (enriched for osteoblasts) were combined and the cells are collected by centrifugation at 400×g for 5 min. The cells were then plated in αMEM containing 10% FCS and antibiotics and were grown to confluency (2–3 days). At this stage the cells were plated for transfection in 60 mm tissue culture dishes at a cell density of 5×10$^5$ cells per dish. These primary osteoblast cultures are capable of self-organizing into bone-like structure in prolonged cultures (Bellows et al, 1986; Harris et al, 1994). HeLa, ROS 17/2.8, and CV-1 cells were purchased from the ATCC.

The isolated FRC cells, enriched for the osteoblast phenotype, were used as recipient cells for transient transfection assays. BMP-4 mRNA is modulated in these cells in a transient fashion during prolonged cultured (Harris et al, 1994b). The technique of electroporation was used for DNA transfection (Potter, 1988; van den Hoff et al, 1992). After electroporation, the cells were divided into aliquots, replated in 100 mm diameter culture dishes and cultured for 48 hrs in modified Eagle's minimal essential media (MEM, GIBCO, Grand Island, N.Y.) with 10% fetal calf serum (FCS). The extracts were assayed for CAT activity according to the method described by Gorman (1988) and CAT activity was normalized by β-galactosidase assay according to the method of Rouet et al(1992).

Figure 4A:
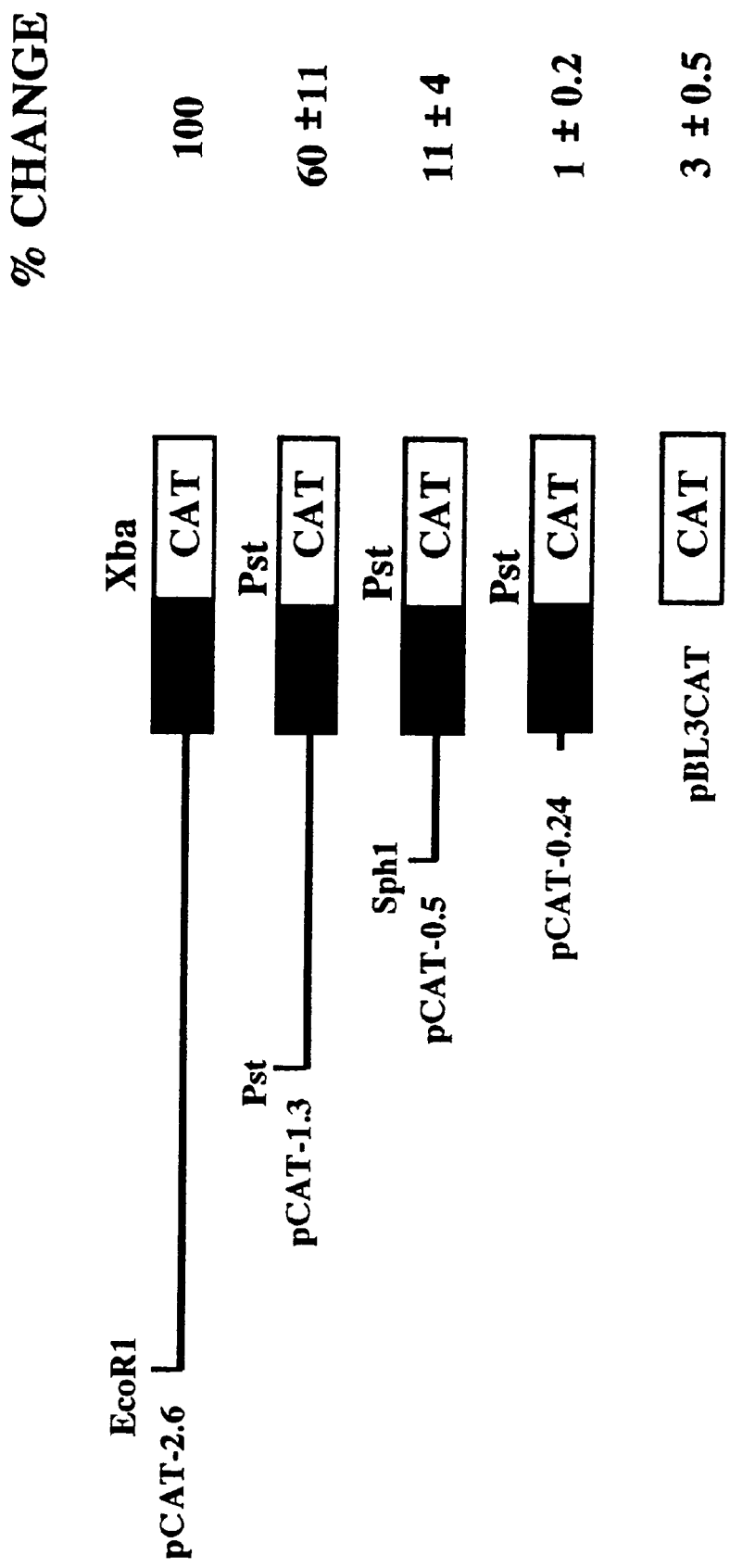
FIG. 4A provides a map of the BMP-4 1A 5'-flanking-CAT plasmid and promoter activity in FRC cells. The 2.6 kb EcoR1 and Xba fragment, 1.3 kb Pst fragment, 0.5 kb SphI and Pst fragment, and 0.25 kb PCR fragment were inserted into pBLCAT3. The closed box indicates the non-coding exon 1A. The CAT box represents the CAT reporter gene. The values represent percentages of CAT activity expressed by pCAT-2.6 set at 100%. The values represent the average of four independent assays.
Figure 4B:
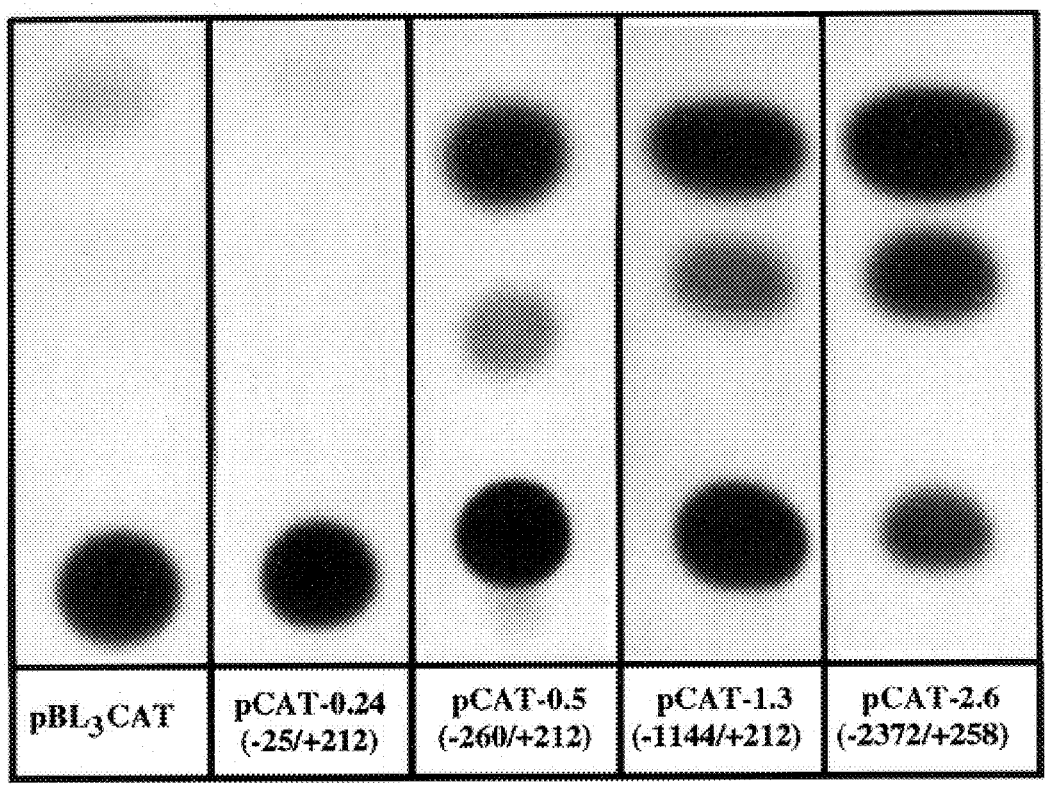
FIG. 4B provides an autoradiogram of CAT assays using FRC cells transfected with BMP-4 1A 5'-flanking-CAT plasmids identified in FIG. 4A.

After 48 hrs of transfection with various BMP-4-CAT reporter gene plasmid constructs, the cells were harvested and the CAT activity was determined. As indicated in FIGS. 4A and 4B, pCAT-0.24 plasmid (−25/+212) has little CAT activity. This plasmid contains −25 to +212 of the 5' noncoding exon 1A and was 3-fold lower that the parent pBL3CAT plasmid. The pCAT-0.5 (−260/+212), pCAT-1.3 (−1144/+212), and pCAT-2.6 (−2372/+258) showed progressive increasing CAT activity when transfected into FRC cells. These data are shown in FIG. 4B. With pCAT-0.5 (−260/+212) there is a 10-fold increase in CAT activity relative to pCAT-0.24 (−25/+212). pCAT-1.3 (−1144/+212) shows a further 6-fold increase and pCAT-2.6 (−2372/+258) shows further 2-fold change over pCAT-1.3 (−1144/+212). Thus the net increase in CAT activity between the pCAT-0.24 (−257/+212) and the pCAT-2.6 (−2372/+258) in FRC cells is approximately 100-fold.

EXAMPLE 2

Description and Characterization of Murine BMP-2 Gene Promoter (a) Cloning of Mouse BMP-2 Genomic DNA Genomic clones of the mouse BMP-2 gene were isolated in order to determine the transcriptional regulation of the BMP-2 gene in primary osteoblasts. 5×10$^6$ plaques were screened from a mouse genomic library, B6/CBA, (purchased from Stratagene, San Diego, Calif.) using BMP-2 cDNA as probe. The BMP-2 cDNA clone was isolated from a cDNA library of PC3 prostate cancer cells (Harris et al, 1994). The human BMP-2 probe was a 1.1 kb SmaI fragment containing most of the coding region.

Figure 5B:
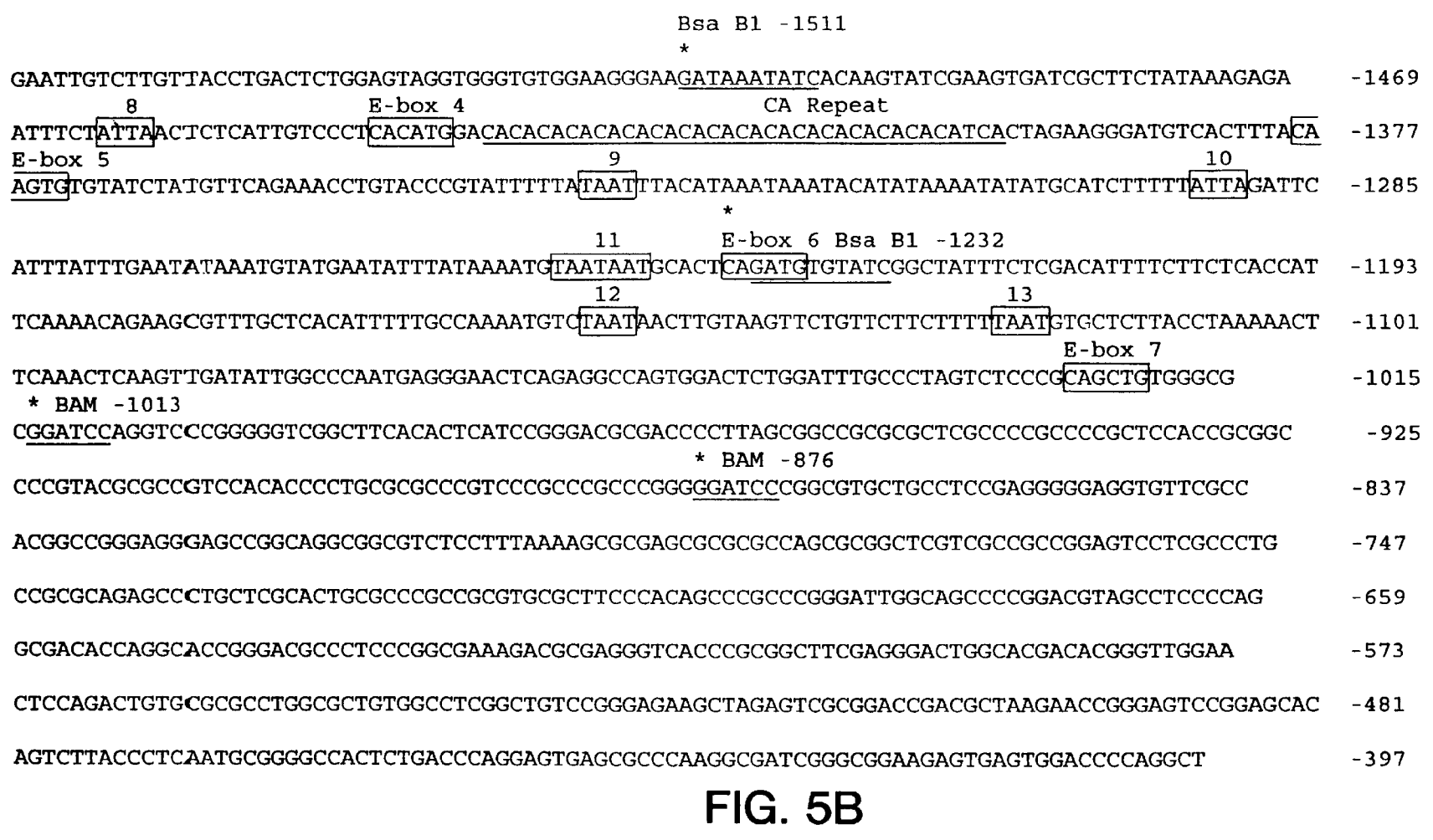

The BMP-2 genomic clones were sequenced by dideoxy chain termination method (Sanger et al, 1977), using deoxyadenosine 5'-[α[$^{35}$S]thio] triphosphate and Sequenase (United States Biochemical, Cleveland, Ohio). All fragments were sequenced at least twice and overlaps were established using the appropriate oligonucleotide primer. Primers were prepared on an Applied Biosystems Model 392 DNA Synthesizer. Approximately 16 kb of one of these BMP-2 clones was completely sequenced (FIG. 9). Analysis of this sequence showed that the mouse BMP-2 gene contains one noncoding and two coding exons (Feng et al, 1994). Analysis of the 5' flanking sequence showed that the BMP-2 gene does not contain typical TATA or CAAT boxes. However, a number of putative response elements and transcription factor recognition sequences were identified upstream of exon 1 (FIG. 5). The 5'-flanking region is GC rich with several SP-1, AP-1, P53, E-box, homeobox, and AP-2 candidate DNA binding elements.

(b) Analysis of Transcription Start Site for BMP-2 Gene

Figure 6A:
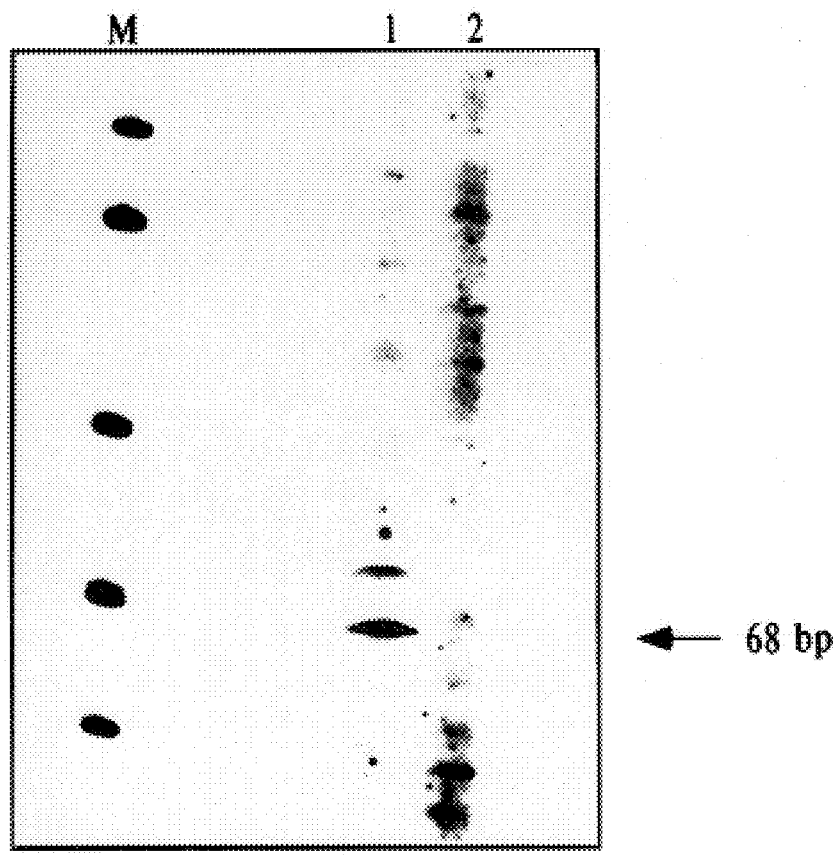
FIG. 6A depicts an autoradiogram showing products of a primer extension assay for determination of the transcription start site of the BMP2 gene, separated on a 8% denaturing urea-polyacrylamide gel, in which Lane 1: Total RNA from fetal rat calvarial osteoblast cells, and Lane 2: Control lane with 10 μg of yeast tRNA. All RNA samples were primed with a $^{32}$P-labeled oligonucleotide from exon 1 of the mouse BMP2 gene, as indicated in FIG. 6B. Lane M: $^{32}$P-labeled MspI digested λ phage DNA, containing DNA fragments spanning from 623 bp to 15 bp (size marker)
Figure 6B:
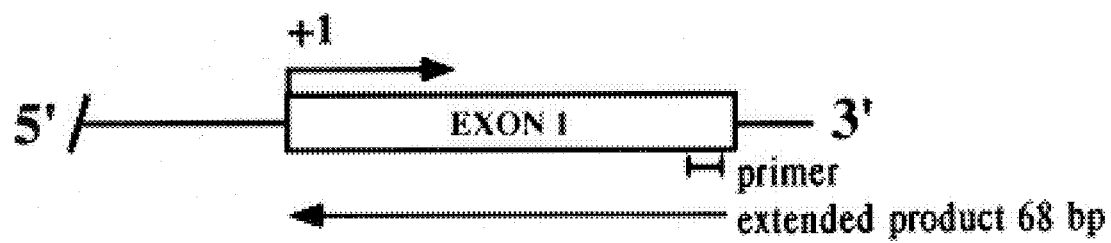
FIG. 6B provides a schematic representation of the primer extension assay. The primer used is a 18 mer synthetic oligonucleotide, 5'-CCCGGCAAGTTCAAGAAG-3' (SEQ. ID NO. 5)

The transcription start sites for the BMP-2 gene were identified using the primer extension technique. Primer extension was carried out as described (Hall et al., 1993). The primer used was a $^{32}$P-labeled 18 mer oligonucleotide 5'-CCCGGCAATTCAAGAAG-3' (SEQ. ID NO. 5). Total RNA obtained from primary fetal rat calvarial osteoblasts, was used for the primer extension. The results are shown in FIG. 6. The major extension product was 68 bp and was used to estimate the major transcription start site (+1, FIG. 5). These results were confirmed by RNase protection assays.

Figure 7:
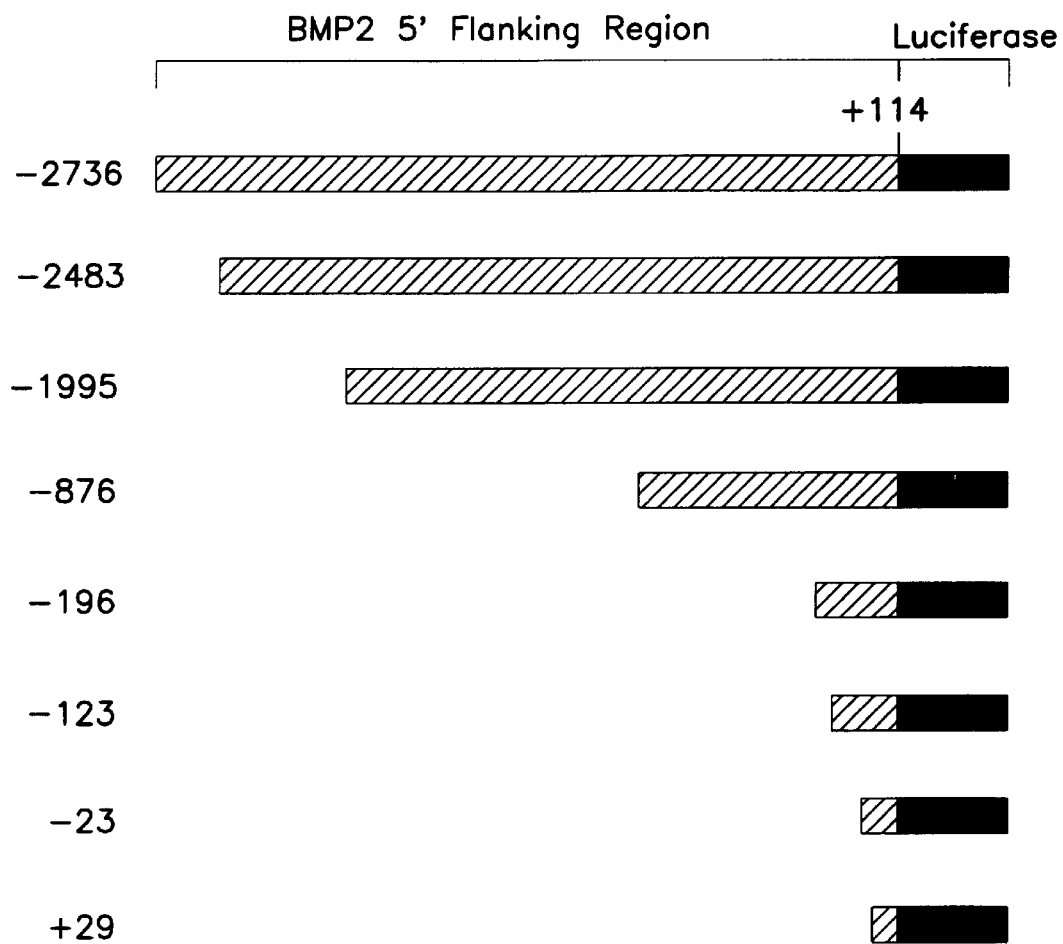
FIG. 7 provides a diagram of selected BMP-2 promoter—luciferase reporter constructs. BMP-2 5'-flanking sequences are designated by hatched boxes (□) and luciferase cDNA is designated by the filled box (■). Base +114 denotes the 3' end of the BMP-2 gene in all the constructs.
Figure 8A:
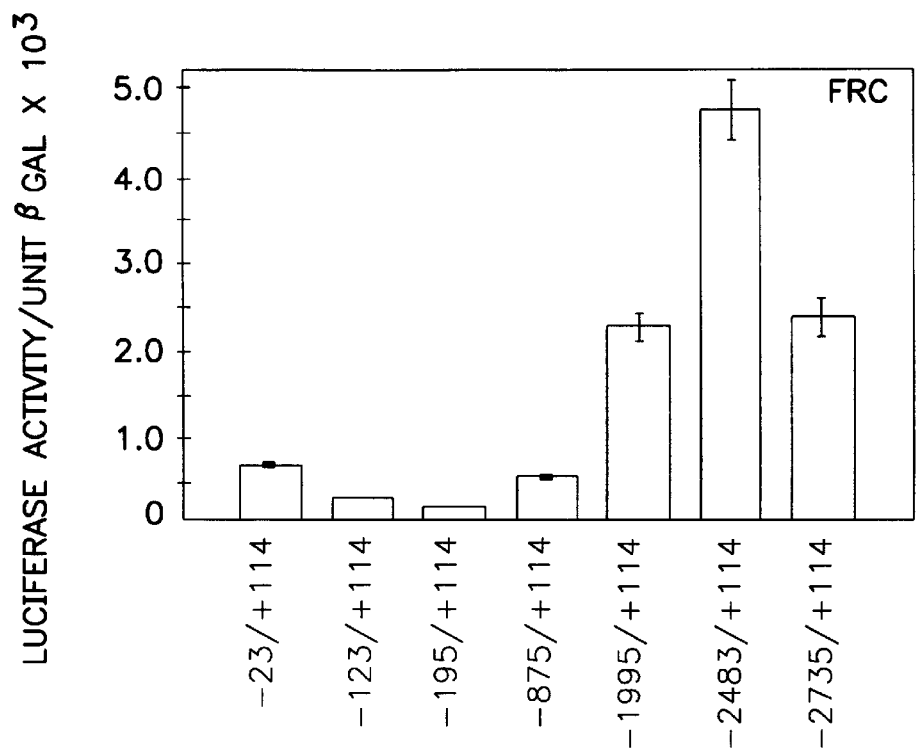
FIG. 8 displays the luciferase enzyme activity for the BMP-2 gene-LUC constructs (shown in FIG. 7) transfected in primary fetal rat calvarial osteoblasts (A), HeLa cells (B) and ROS 17/2.8 osteoblasts (C). The luciferase activity has been normalized to β-galactosidase activity in the cell lysates.
Figure 8B:
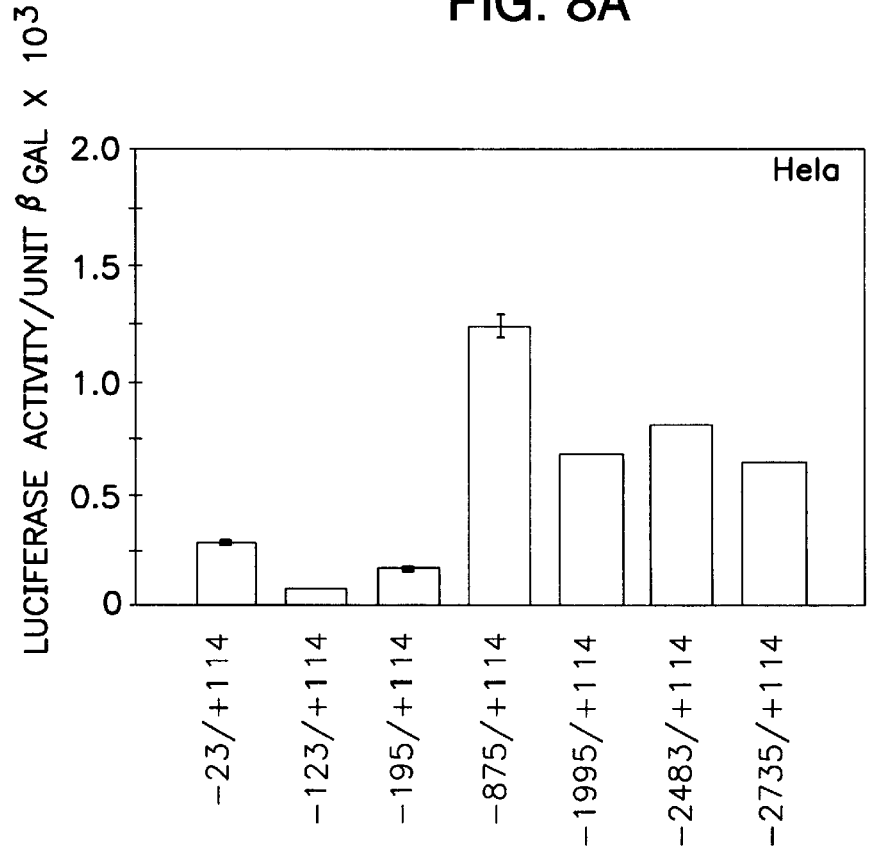
Figure 8C:
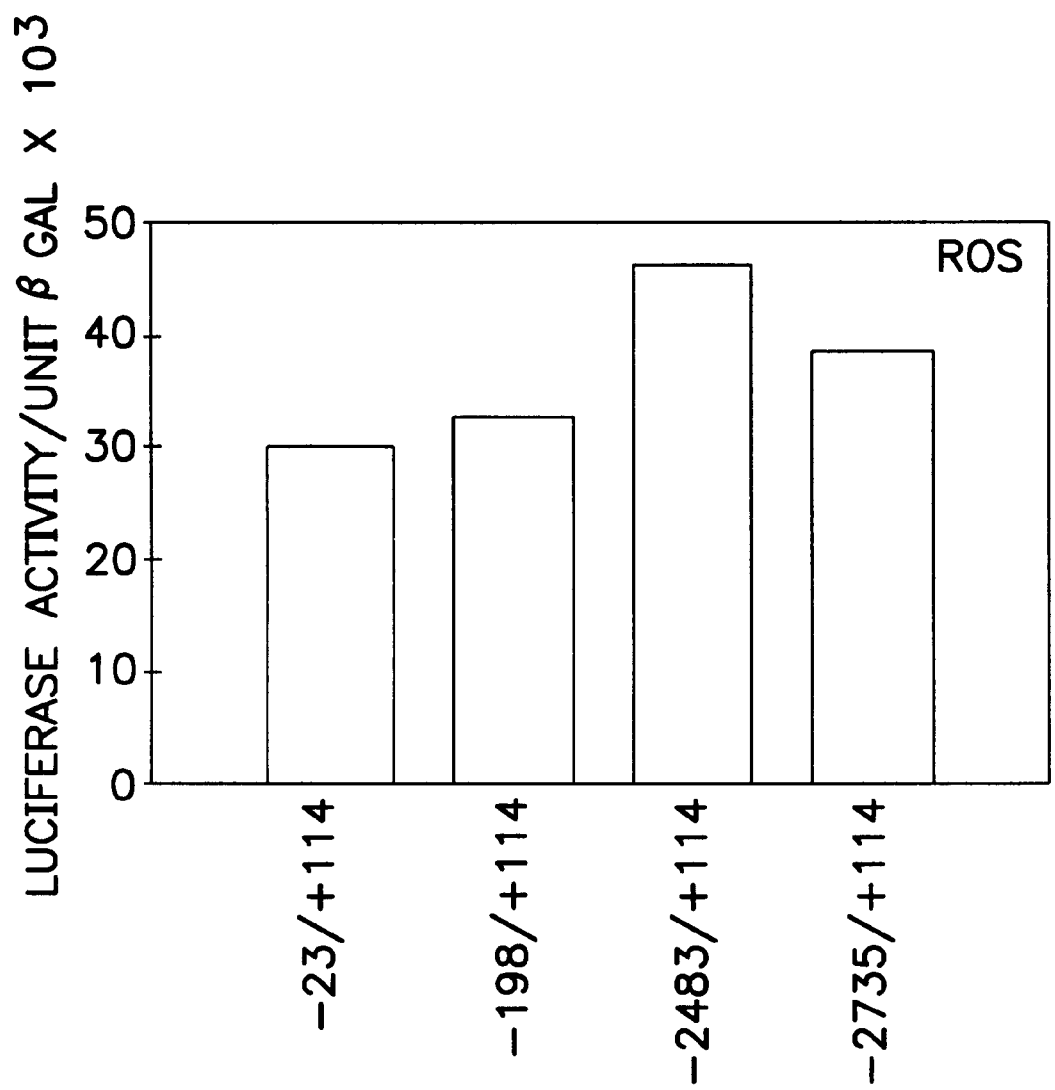

(c) Identification of BMP-2 Promoter and Enhancer Activity Using Luciferase (LUC) Reporter Gene Constructs The BMP-2-LUC constructs (FIG. 7) were designed to contain variable 5' boundaries from BMP-2 5'-flanking sequences spanning the transcription start site (+1). Each construct contained the 3' boundary at +114 in exon 1 (FIG. 6). These constructs were individually transfected into primary cultures of fetal rat calvarial osteoblasts, ROS 17/2.8 osteosarcoma cells, HeLa cells, and CV-1 cells by the calcium-phosphate precipitation technique and the promoter activity for each of these constructs was assayed 24 hrs following transfection by measuring the luciferase enzyme activity for each individual cell lysate. The LUC (luciferase enzyme assay) technique is described below under (f). Plasmid pSVβGal was co-transfected with each plasmid construct to normalize for the transfection efficiency in each sample. The experiments were repeated at least five times in independent fetal rat calvarial cultures, with each assay done in triplicate. The mean values from a representative experiment are shown in FIG. 8.

(d) Isolation of Primary Fetal Rat Calvarial Osteoblasts for Functional Studies of BMP-2 Gene Promoter The cells used for transient transfection studies were isolated from 19 day-old fetal rat calvariae by sequential digestion with trypsin and collagenase, as described by Bellows et al., (1986) and Harris et al., (1994). In brief, the calvarial bone were surgically removed and cleaned by washing in α minimal essential media (αMEM) containing 10% V/V fetal calf serum (FCS) and antibiotics. The bones were minced with scissors and were transferred to 35 mm tissue culture dish containing 5 ml of sterile bacterial collagenase (0.1%) and trypsin (0.05%). This was then incubated at 37° C. for 20 min. The cells released at this time were collected and immediately mixed with an equal volume of FCS to inactivate trypsin. This procedure was repeated 6 times to release cells at 20 min intervals. Cells released from 3rd, 4th, 5th and 6th digestion (enriched for osteoblasts) were combined and the cells were collected by centrifugation at 400 g for 5 min. The cells were then plated in αMEM containing 10% FCS and antibiotics and were grown to confluency (2–3 days). At this stage the cells were plated for transfection in 60 mm tissue culture dishes at a cell density of 5×10$^5$ cells per dish. These primary osteoblast cultures are capable of mineralized bone in prolonged cultures (Bellows et al, 1986; Harris et al, 1994). HeLa, ROS 17/2.8, and CV-1 cells were purchased from the ATCC.

(e) Transient Transfection Assay

For transient transfection assay, the primary osteoblast cells were plated at the above mentioned cell density 18–24 hrs prior to transfection. The transfection was carried out using a modified calcium-phosphate precipitation method (Graham & van der Eb 1973; Frost & Williams 1978). The cells were incubated for 4 hrs at 37° C. with 500 μl of a calcium phosphate precipitate of plasmid DNA containing 10 μg of reporter plasmid construct and 1 μg of pSVβGal (for normalization of transfection efficiency) in 0.15 M $CaCl_2$ and Hepes buffered saline (21 mM Hepes, 13.5 mM NaCl, 5 mM KCl, 0.7 mM $Na_2HPO_4$, 5.5 mM dextrose, pH 7.05–7.1). After the 4 hr incubation period of cells with precipitate, the cells were subjected to a 2 min treatment of 15% glycerol in αMEM, followed by addition of fresh αMEM containing insulin, transferrin and selenium (ITS) (Upstate Biotechnology, Lake Placid, N.Y.). The cells were harvested 24 hrs post transfection.

(f) Luciferase and β-galactosidase Assay

Cell lysates were prepared and luciferase enzyme assay was carried out using assay protocols and the assay kit from Promega (Madison, Wis.). Routinely 20 μl of cell lysate was mixed with 100 μl of luciferase assay reagent (270 μM coenzyme A, 470 μM luciferin and 530 μM ATP) and the luciferase activity was measured for 10 sec in a TURNER TD-20e luminometer. The values were normalized with respect to the β-galactosidase enzyme activity, obtained for each experimental sample.

The β-galactosidase enzyme activity was measured in the cell lysate using a 96 well microtiter plate according to Rouet et al (1992). 10–20 μl cell lysate was added to 90–80 μl β-galactosidase reaction buffer containing 88 mM phosphate buffer, pH 7.3, 11 mM KCl, 1 mM $MgCl_2$, 55 mM β mercaptoethanol, 4.4 mM chlorophenol red β-D-galactopyranoside (Boehringer-Mannheim Corp., Indianapolis, Ind.). The reaction mixture was incubated at 37° C. for 30–60 min, depending on transfection efficiency, and the samples were read with an ELISA plate reader at 600 nm.

(g) Plasmid Construction

The luciferase basic plasmid (pGL basic) was the vector used for all constructs (purchased from Promega, Madison, Wis.). Different lengths of DNA fragments from the BMP-2 5'-flanking region were cloned at the multiple cloning sites of this plasmid, which is upstream of the firefly luciferase cDNA. The BMP-2 DNA fragments were isolated either by using available restriction enzyme sites (constructs −196/+114, −876/+114, −1995/+114, −2483/+114, and −2736/+114) or by polymerase chain reaction using specific oligonucleotide primers (constructs −23/+114, −123/+114 and +29/+114).

The minimal promoter activity for the BMP-2 gene was identified in the shortest construct containing 23 bp upstream of the transcription start site (−23/+114). No luciferase activity was noted in the construct that did not include the transcription start site (+29/+114). Two other constructs containing increasing lengths of 5' sequences up to −196 bp showed reproducible decreases in promoter activity in fetal rat calvarial osteoblasts and HeLa cells (FIG. 8). The −876/+114 construct showed a 5-fold increase in activity in HeLa cells. The −1995/+114, −2483/+114 and −2736/+114 constructs showed decreased promoter activity when compared to the −876/+114 construct only in HeLa cells (FIG. 8).

In the primary fetal rat calvarial osteoblasts, the 2.6 kb construct (−2483/+114) demonstrated a 2–3-fold increase in luciferase activity over that of the −1995/+114 construct (FIG. 8). These results suggest that one or more positive response regions are present between −196 and −1995 and that the DNA sequence between −1995 and −2483 bp has other positive regulatory elements that could modulate BMP-2 transcription. The largest 2.9 kb construct (−2736/+114) repeatedly demonstrated a 20–50% decrease in promoter activity compared to the −2483/+114 construct, in these primary fetal rat calvarial osteoblasts (FIG. 8).

In ROS 17/2.8 osteosarcoma cells, the BMP-2 promoter activity was consistently higher than either the primary fetal rat calvarial osteoblasts or HeLa cells (FIG. 8). All of the deletion constructs showed similar promoter activity in ROS 17/2.8 osteosarcoma cells. The transformed state in ROS 17/2.8 cells may be responsible for the marked expression of the BMP-2 gene. ROS 17/2.8 cells represent a well differentiated osteosarcoma and they produce high levels of BMP-2 mRNA. They form tumors in nude mice with bone-like material in the tumor (Majeska et al, 1978; Majeska et al, 1980).

(h) Specificity of the BMP-2 Promoter

To analyze the activity of the BMP-2 promoter in cell types not expressing BMP-2 mRNA, BMP-2 promoter constructs were transfected into CV-1 cells (monkey kidney cells). The BMP-2 promoter activity was found to be very low for all constructs. This suggests that this region of the BMP-2 promoter is functional only in cells such as primary fetal rat calvarial osteoblasts, HeLa and ROS 17/2.8 that express endogenous BMP-2 mRNA (Anderson & Coulter 1968). CV-1 cells do not express BMP-2 mRNA. The BMP-2 promoter is likely active in other cell types that express BMP-2, such as prostate cells and chondrocytes, although regulation of transcription may be different in these cells.

EXAMPLE 3

Use of Plasmid Constructs Containing BMP Promoters With Reporter Genes to Identify Osteogenic Agents Plasmid constructs containing BMP promoters with reporter genes have been transfected into osteoblastic cells. The cells which have been utilized include primary cultures of fetal rat calvarial osteoblasts, cell lines obtained as gifts or commercially (MC3T3-E12 cells, MG-63 cells, U2OS cells, UMR106 cells, ROS 17/2.8 cells, SaOS2 cells, and the like as provided in the catalog from the ATCC) and bone and cartilage cell lines established from transgenic mice. The bone cells are transfected transiently or stably with the plasmid constructs, exposed to the chemical compound, agent or factor to be tested for 48 hours, and then luciferase or CAT activity is measured in the cell lysates.

Regulation of expression of the growth factor is assessed by culturing bone cells in αMEM medium with 10% fetal calf serum and 1% penicillin/streptomycin and 1% glutamine. The cells are placed in microtiter plates at a cell density of $5\times10^3$ cells/100 μl/well. The cells are allowed to adhere and then incubated at 37° C. at 5% $CO_2$ for 24 hours and then the media is removed and replaced with 50 μl αMEM and 4% fetal calf serum. 50 μl aliquots containing the compound or factor to be tested in 0.1% BSA solution is added to each well. The final volume is 100 μl and the final serum concentration is 2% fetal calf serum. Recombinant rat BMP-2 expressed in Chinese hamster ovarian cells is used as a positive control.

The treated cells are incubated at 37° C. at 5% $CO_2$ for 48 hours. The media is then removed and the cells are rinsed 3 times with phosphate buffered saline (PBS). Excess PBS is removed from the wells and 100 μl of cell culture lysing reagent (Promega #E153A) is added to each well. After 10 minutes, 10 μl of the cell lysate is added to a 96-well white luminometric plate (Dynatech Labs #07100) containing 100 μl luciferase assay buffer with substrate (Promega #E152A).

The luciferase activity is read using a Dynatech ML2250 automated 96-well luminometer. The data is expressed as either picograms of luciferase activity per well or picograms of luciferase activity per µg protein.

EXAMPLE 4

Demonstration That Bone Cells Transfected With BMP Promoters Can Be Used To Screen for Osteogenic Agents To demonstrate that the present invention is useful in evaluating potential osteogenic agents, a random array of chemical compounds from a chemical library obtained commercially was screened. It was found that approximately 1 in 100 such compounds screened produces a positive response in the present assay system compared with the positive control, recombinant BMP-2, which is known to enhance BMP-2 transcription. Compounds identified from the random library were subjected to detailed dose-response curves, to demonstrate that they enhance BMP messenger RNA expression, and that they enhance other biological effects in vitro, such as expression of structural proteins including osteocalcin, osteopontin and alkaline phosphatase, and enhance bone nodule formation in prolonged primary cultures of calvarial rodent osteoblasts.

Compounds identified in this way can be tested for their capacity to stimulate bone formation in vivo in mice. To demonstrate this, the compound can be injected locally into subcutaneous tissue over the calvarium of normal mice and then the bone changes are followed histologically. It has been found that certain compounds identified by the present invention stimulate the formation of new bone in this in vivo assay system.

The effects of compounds are tested in ICR Swiss mice, aged 4–6 weeks and weighing 13–26 g. The compound at 20 mg/kg or vehicle alone (100 µl of 5% DMSO and phosphate-buffered 0.9% saline) are injected three times daily for 7 days. The injections are given into the subcutaneous tissues overlying the right side of the calvaria of five mice in each treatment group in each experiment.

Mice are killed by ether inhalation on day 14, i.e. 7 days after the last injection of compound. After fixation in 10% phosphate-buffered formalin, the calvariae are examined. The occipital bone is removed by cutting immediately behind and parallel to the lambdoid suture, and the frontal bone is removed by cutting anterior to the coronal suture using a scalpel blade. The bones are then bisected through the coronal plane and the 3- to 4 mm strips of bone are decalcified in 14% EDTA, dehydrated in graded alcohols, and embedded in paraffin. Four 3 µm thick nonconsecutive step sections are cut from each specimen and stained using hematoxylin and eosin.

Two representative sections from the posterior calvarial strips are used. Histological measurements are carried out using a digitizing tablet and the Osteomeasure image analysis system (Osteometrics Inc., Atlanta, Ga.) on the injected and noninjected sides of the calvariae in a standard length of bone between the sagittal suture and the muscle insertion at the lateral border of each bone. Measurements consist of 1) Total bone area (i.e., bone and marrow between inner and outer periosteal surfaces); 2) Area of new woven bone formed on the outer calvarial surface; 3) The extent of osteoblast lined surface on the outer calvarial surface; 4) The area of the outer periosteum; and 5) The length of calvarial surface. From these measurements, the mean width of new bone and periosteum and the percentage of surface lined by osteoblasts on the outer calvarial surface, can be determined.

By reference to the above disclosure and examples, it is seen that the present invention provides a new cell-based assay for identifying and evaluating compounds which stimulate the growth of bone. Also provided in accordance with the present invention are promoter regions of bone morphogenetic protein genes, and a system for identifying osteogenic agents utilizing such promoters operatively linked to reporter genes in expression vectors.

The present invention provides the means to specifically identify osteogenic agents which stimulate bone cells to produce bone growth factors in the bone morphogenetic protein family. These osteogenic agents are shown to be useful to increase the activity of the promoters of genes of members of the BMP family and other bone growth factors normally produced by bone cells.

All publications and patent applications cited in this specification are herein incorporated by reference as if each individual publication or patent application are specifically and individually indicated to be incorporated by reference.

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the appended claims.

Anderson, H. C. and P. R. Coulter (1968) Fed. Proc. 27, 475.

Bellows, C. G., J. E. Aubin, J. N. M. Heersche and M. E. Antosz (1986) Mineralized bone nodules formed in vitro from enzymatically released rat calvarial cell populations. Calcif. Tissue Int. 38, 143–154.

Chen, D., J. Q. Feng, M. Feng, M. A. Harris, G. R. Mundy and S. E. Harris (1993) Biochim Biophys Acta 1174, 289–292.

Feng, J. Q., M. A. Harris, N. Ghosh-Choudhury, M. Feng, G. R. Mundy and S. E. Harris (1994) Biochem. Biophys. Acta 1218, 221–224.

Frost, E. and J. Williams (1978) Virology 91, 39–50.

Gorman, C. (1988) in DNA Cloning, A Practical Approach (Gover, D. M., ed) Vol. II, pp. 157–158, IRL Press, Oxford, England.

Graham, F. L., and A. J. van der Eb (1973) Virology 52, 456–467.

Hall, J. A., M. A. Harris, R. Intres, and S. E. Harris (1993) J Cell Biochem 51, 116–127.

Harris, S. E., L. F. Bonewald, M. A. Harris, M. Sabatini, S. Dallas, J. Feng, N. Ghosh-Choudhury, J. Wozney and G. R. Mundy (1994) Effects of TGFβ on bone nodule formation and expression of bone morphogenetic protein-2, osteocalcin, osteopontin, alkaline phosphatase and Type I collagen mRNA in prolonged cultures of fetal rat calvarial osteoblasts. J Bone Miner Res 9, 855–863.

Harris, S. E., M. Sabatini, M. A. Harris, J. Q. Feng, J. Wozney and G. R. Mundy (1994) Expression of bone morphogenetic protein messenger RNA in prolonged cultures of fetal rat calvarial cells. J Bone Min Res 9, 389–394.

Harris, S. E., M. Harris, M. Mahy, J. Wozney, J. Feng and G. R. Mundy (1994) Expression of bone morphogenetic proteins by normal rat and human prostate and prostate cancer cells. The Prostate 24, 204–211.

Kurihara, T., K. Kitamura, K. Takaoka, H. Nakazato (1993) Murine bone morphogenetic protein-4 gene: existence of multiple promoters and exons for the 5'-untranslated region. Biochem Biophys Res Commun 192, 1049–1056.

Luckow, B. and G. Schutz (1987) Nucleic Acids Res. 15, 5490.

Majeska, R. J., S. B. Rodan and G. A. Rodan (1978) Maintenance of parathyroid hormone response in clonal rat osteosarcoma lines. Exp Cell Res 111, 465–468.

Majeska, R. J., S. B. Rodan and G. A. Rodan (1980) Parathyroid hormone responsive clonal cell lines from rat osteosarcoma. Endocrinology 107, 1494–1503.

Potter, H. (1988) Anal Biochem 174, 361–373.

Rouet, P., G. Raguenez and J-P Salier (1992) Biotechniques 13, 700–701.

Sambrook, J., E. F. Fritsch and T. Maniatis (1989) in Molecular Cloning: A Laboratory Manual, Cold Spring Harbor Laboratory Press, Cold Spring Harbor, N.Y.

Sanger, F., S. G. Nicklen and A. R. Coulson (1977) Proc. Natl. Acad. Sci. USA 74, 5463–5467.

Stein, G. S., J. B. Lian and T. A. Owen (1990) Relationship of cell growth to the regulation of tissue-specific gene expression during osteoblast differentiation. FASEB J 4, 3111–3123.

Urist, M. R. (1965) Bone: Formation by autoinduction. Science 150, 893.

van den Hoff, M. J. B., A. F. M. Moorman, and W. H. Lamers (1992) Nucleic Acids Res. 20, 2902.

Wozney, J. M., V. Rosen, A. J. Celeste, L. M. Mitsock, M. J. Whitters, R. W. Kriz, R. M. Hewick and E. A. Wange (1988) Novel regulators of bone formation: Molecular clones and activities. Science 242, 1528–1534.

Wozney, J. M. (1992) The bone morphogenetic protein family and osteogenesis. Mol Reprod Dev 32, 160–167.

Wozney, J. M. and V. Rosen (1993) Bone morphogenetic proteins. In: Physiology and Pharmacology of Bone (edited by Mundy G. R., Martin T. J.). Springer-Verlag, Chapter 20, 725–743.

We claim:

1. An isolated DNA molecule which comprises the nucleotide sequence at positions −2372 to +316 depicted in FIG. 1C (SEQ. ID NO. 3), or a portion thereof which is effective as a promoter.

2. A recombinant expression vector comprising the portion of the DNA molecule of claim 1 which is effective as a promoter.

3. The recombinant expression vector of claim 2 further comprising a nucleotide sequence encoding an assayable product operatively linked to said portion effective as a promoter.

4. The recombinant expression vector of claim 3 wherein said assayable product is firefly luciferase, chloramphenicol acetyl transferase (CAT), β-galactosidase, green fluorescent protein (GFP), human growth hormone, alkaline phosphatase or β-glucuronidase.

5. A system for identifying osteogenic agents comprising:
   host cells or a cell line modified to contain the expression vector of claim 3; and
   means for detecting said assayable product produced in response to exposure to an osteogenic agent.

6. The system of claim 5 wherein said assayable product is firefly luciferase, chloramphenicol acetyl transferase (CAT), β-galactosidase, green fluorescent protein (GFP), human growth hormone, alkaline phosphatase or β-glucuronidase.

7. Recombinant host cells or a recombinant host cell line modified to contain the expression vector of claim 3.

8. A method for identifying an osteogenic agent comprising
   contacting the cells or cell line of claim 7 with at least one compound suspected of possessing osteogenic activity; and
   measuring the production of said assayable product in the presence and absence of said compound;
   whereby a compound which results in an increase in production of said assayable product in its presence as opposed to its absence is identified as an osteogenic agent.

9. The method of claim 8 wherein said assayable product is firefly luciferase, chloramphenicol acetyl transferase (CAT), β-galactosidase, green fluorescent protein (GFP), human growth hormone, alkaline phosphatase or β-glucuronidase.

10. An isolated DNA molecule which comprises the nucleotide sequence at positions −2736 to +139 depicted in FIG. 5 (SEQ. ID NO. 4), or a portion thereof which is effective as a promoter.

11. A recombinant expression vector comprising the portion of the DNA molecule of claim 10 which is effective as a promoter.

12. The recombinant expression vector of claim 11 further comprising a nucleotide sequence encoding an assayable product operatively linked to said portion effective as a promoter.

13. The recombinant expression vector of claim 12 wherein said assayable product is firefly luciferase, chloramphenicol acetyl transferase (CAT), β-galactosidase, green fluorescent protein (GFP), human growth hormone, alkaline phosphatase or β-glucuronidase.

14. A system for identifying osteogenic agents comprising:
   host cells or a cell line modified to contain the expression vector of claim 12, and
   means for detecting said assayable product produced in response to exposure to an osteogenic agent.

15. The system of claim 14 wherein said assayable product is firefly luciferase, chloramphenicol acetyl transferase (CAT), β-galactosidase, green fluorescent protein (GFP), human growth hormone, alkaline phosphatase or β-glucuronidase.

16. Recombinant host cells or a recombinant host cell line modified to contain the expression vector of claim 12.

17. A method for identifying an osteogenic agent comprising
   contacting the cells or cell line of claim 16 with at least one compound suspected of possessing osteogenic activity; and
   measuring the production of said assayable product in the presence and absence of said compound;
   whereby a compound which results in an increase in production of said assayable product in its presence as opposed to its absence is identified as an osteogenic agent.

18. The method of claim 17 wherein said assayable product is firefly luciferase, chloramphenicol acetyl transferase (CAT), β-galactosidase, green fluorescent protein (GFP), human growth hormone, alkaline phosphatase or β-glucuronidase.

* * * * *

SEQUENCE LISTING

```
(1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 2310 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 768..1991

(xi) SEQUENCE DESCRIPTION: SEQ ID NO:1:

GGGAGGAAGG GAAGAAAGAG AGGGAGGGAA AAGAGAAGGA AGGAGTAGAT GTGAGAGGGT        60

GGTGCTGAGG GTGGGAAGGC AAGAGCGCGA GGCCTGGCCC GGAAGCTAGG TGAGTTCGGC       120

ATCCGAGCTG AGAGACCCCA GCCTAAGACG CCTGCGCTGC AACCCAGCCT GAGTATCTGG       180

TCTCCGTCCC TGATGGGATT CTCGTCTAAA CCGTCTTGGA GCCTGCAGCG ATCCAGTCTC       240

TGGCCCTCGA CCAGGTTCAT TGCAGCTTTC TAGAGGTCCC CAGAAGCAGC TGCTGGCGAG       300

CCCGCTTCTG CAGGAACCAA TGGTGAGCTC GAGTGCAGGC CGAAAGCTGT TCTCGGGTTT       360

GTAGACGCTT GGGATCGCGC TTGGGGTCTC CTTTCGTGCC GGGTAGGAGT TGTAAAGCCT       420

TTGCAACTCT GAGATCGTAA AAAAAATGTG ATGCGCTCTT TCTTTGGCGA CGCCTGTTTT       480

GGAATCTGTC CGGAGTTAGA AGCTCAGACG TCCACCCCCC ACCCCCGCC  CACCCCCTCT       540

GCCTTGAATG GCACCGCCGA CCGGTTTCTG AAGGATCTGC TTGGCTGGAG CGGACGCTGA       600

GGTTGGCAGA CACGGTGTGG ATTTTAGGAG CCATTCCGTA GTGCCATTCG GAGCGACGCA       660

CTGCCGCAGC TTCTCTGAGC CTTTCCAGCA AGTTTGTTCA AGATTGGCTC CCAAGAATCA       720

TGGACTGTTA TTATGCCTTG TTTTCTGTCA GTGAGTCCAG AGACACC ATG ATT CCT        776
                                                    Met Ile Pro
                                                      1

GGT AAC CGA ATG CTG ATG GTC GTT TTA TTA TGC CAA GTC CTG CTA GGA        824
Gly Asn Arg Met Leu Met Val Val Leu Leu Cys Gln Val Leu Leu Gly
  5                  10                  15

GGC GCG AGC CAT GCT AGT TTG ATA CCT GAG ACC GGG AAG AAA AAA GTC        872
Gly Ala Ser His Ala Ser Leu Ile Pro Glu Thr Gly Lys Lys Lys Val
 20                  25                  30                  35
```

```
GCC GAG ATT CAG GGC CAC GCG GGA GGA CGC CGC TCA GGG CAG AGC CAT      920
Ala Glu Ile Gln Gly His Ala Gly Gly Arg Arg Ser Gly Gln Ser His
             40                  45                  50

GAG CTC CTG CGG GAC TTC GAG GCG ACA CTT CTA CAG ATG TTT GGG CTG      968
Glu Leu Leu Arg Asp Phe Glu Ala Thr Leu Leu Gln Met Phe Gly Leu
                 55                  60                  65

CGC CGC CGT CCG CAG CCT AGC AAG AGC GCC GTC ATT CCG GAT TAC ATG     1016
Arg Arg Arg Pro Gln Pro Ser Lys Ser Ala Val Ile Pro Asp Tyr Met
             70                  75                  80

AGG GAT CTT TAC CGG CTC CAG TCT GGG GAG GAG GAG GAA GAG CAG         1064
Arg Asp Leu Tyr Arg Leu Gln Ser Gly Glu Glu Glu Glu Glu Gln
         85                  90                  95

AGC CAG GGA ACC GGG CTT GAG TAC CCG GAG CGT CCC GCC AGC CGA GCC     1112
Ser Gln Gly Thr Gly Leu Glu Tyr Pro Glu Arg Pro Ala Ser Arg Ala
100                 105                 110                 115

AAC ACT GTG AGG AGT TTC CAT CAC GAA GAA CAT CTG GAG AAC ATC CCA     1160
Asn Thr Val Arg Ser Phe His His Glu Glu His Leu Glu Asn Ile Pro
                120                 125                 130

GGG ACC AGT GAG AGC TCT GCT TTT CGT TTC CTC TTC AAC CTC AGC AGC     1208
Gly Thr Ser Glu Ser Ser Ala Phe Arg Phe Leu Phe Asn Leu Ser Ser
                135                 140                 145

ATC CCA GAA AAT GAG GTG ATC TCC TCG GCA GAG CTC CGG CTC TTT CGG     1256
Ile Pro Glu Asn Glu Val Ile Ser Ser Ala Glu Leu Arg Leu Phe Arg
            150                 155                 160

GAG CAG GTG GAC CAG GGC CCT GAC TGG GAA CAG GGC TTC CAC CGT ATA     1304
Glu Gln Val Asp Gln Gly Pro Asp Trp Glu Gln Gly Phe His Arg Ile
165                 170                 175

AAC ATT TAT GAG GTT ATG AAG CCC CCA GCA GAA ATG GTT CCT GGA CAC     1352
Asn Ile Tyr Glu Val Met Lys Pro Pro Ala Glu Met Val Pro Gly His
180                 185                 190                 195

CTC ATC ACA CGA CTA CTG GAC ACC AGA CTA GTC CAT CAC AAT GTG ACA     1400
Leu Ile Thr Arg Leu Leu Asp Thr Arg Leu Val His His Asn Val Thr
                200                 205                 210

CGG TGG GAA ACT TTC GAT GTG AGC CCT GCA GTC CTT CGC TGG ACC CGG     1448
Arg Trp Glu Thr Phe Asp Val Ser Pro Ala Val Leu Arg Trp Thr Arg
            215                 220                 225

GAA AAG CAA CCC AAT TAT GGG CTG GCC ATT GAG GTG ACT CAC CTC CAC     1496
Glu Lys Gln Pro Asn Tyr Gly Leu Ala Ile Glu Val Thr His Leu His
        230                 235                 240

CAG ACA CGG ACC CAC CAG GGC CAG CAT GTC AGA ATC AGC CGA TCG TTA     1544
Gln Thr Arg Thr His Gln Gly Gln His Val Arg Ile Ser Arg Ser Leu
245                 250                 255

CCT CAA GGG AGT GGA GAT TGG GCC CAA CTC CGC CCC CTC CTG GTC ACT     1592
Pro Gln Gly Ser Gly Asp Trp Ala Gln Leu Arg Pro Leu Leu Val Thr
260                 265                 270                 275

TTT GGC CAT GAT GGC CGG GGC CAT ACC TTG ACC CGC AGG AGG GCC AAA     1640
Phe Gly His Asp Gly Arg Gly His Thr Leu Thr Arg Arg Arg Ala Lys
                280                 285                 290

CGT AGT CCC AAG CAT CAC CCA CAG CGG TCC AGG AAG AAG AAT AAG AAC     1688
Arg Ser Pro Lys His His Pro Gln Arg Ser Arg Lys Lys Asn Lys Asn
            295                 300                 305

TGC CGT CGC CAT TCA CTA TAC GTG GAC TTC AGT GAC GTG GGC TGG AAT     1736
Cys Arg Arg His Ser Leu Tyr Val Asp Phe Ser Asp Val Gly Trp Asn
        310                 315                 320

GAT TGG ATT GTG GCC CCA CCC GGC TAC CAG GCC TTC TAC TGC CAT GGG     1784
Asp Trp Ile Val Ala Pro Pro Gly Tyr Gln Ala Phe Tyr Cys His Gly
325                 330                 335

GAC TGT CCC TTT CCA CTG GCT GAT CAC CTC AAC TCA ACC AAC CAT GCC     1832
Asp Cys Pro Phe Pro Leu Ala Asp His Leu Asn Ser Thr Asn His Ala
```

```
        340             345             350             355
ATT GTG CAG ACC CTA GTC AAC TCT GTT AAT TCT AGT ATC CCT AAG GCC       1880
Ile Val Gln Thr Leu Val Asn Ser Val Asn Ser Ser Ile Pro Lys Ala
                360             365             370

TGT TGT GTC CCC ACT GAA CTG AGT GCC ATT TCC ATG TTG TAC CTG GAT       1928
Cys Cys Val Pro Thr Glu Leu Ser Ala Ile Ser Met Leu Tyr Leu Asp
            375             380             385

GAG TAT GAC AAG GTG GTG TTG AAA AAT TAT CAG GAG ATG GTG GTA GAG       1976
Glu Tyr Asp Lys Val Val Leu Lys Asn Tyr Gln Glu Met Val Val Glu
        390             395             400

GGG TGT GGA TGC CGC TGAGATCAGA CAGTCCGGAG GGCGGACACA CACACACACA       2031
Gly Cys Gly Cys Arg
    405

CACACACACA CACACACACA CACACACACA CGTTCCCATT CAACCACCTA CACATACCAC     2091

ACAAACTGCT TCCCTATAGC TGGACTTTTA TCTTAAAAAA AAAAAAAAGA AAGAAAGAAA     2151

GAAAGAAAGA AAAAAAATGA AAGACAGAAA AGAAAAAAAA AACCCTAAAC AACTCACCTT     2211

GACCTTATTT ATGACTTTAC GTGCAAATGT TTTGACCATA TTGATCATAT TTTGACAAAT     2271

ATATTTATAA AACTACATAT TAAAAGAAAA TAAAATGAG                            2310
```

(2) INFORMATION FOR SEQ ID NO:2:

(i) SEQUENCE CHARACTERISTICS:
        (A) LENGTH: 408 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ile Pro Gly Asn Arg Met Leu Met Val Val Leu Leu Cys Gln Val
 1               5                  10                  15

Leu Leu Gly Gly Ala Ser His Ala Ser Leu Ile Pro Glu Thr Gly Lys
                20                  25                  30

Lys Lys Val Ala Glu Ile Gln Gly His Ala Gly Gly Arg Arg Ser Gly
            35                  40                  45

Gln Ser His Glu Leu Leu Arg Asp Phe Glu Ala Thr Leu Leu Gln Met
        50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Glu Gln Ser Gln Gly Thr Gly Leu Glu Tyr Pro Glu Arg Pro Ala
            100                 105                 110

Ser Arg Ala Asn Thr Val Arg Ser Phe His His Glu Glu His Leu Glu
        115                 120                 125

Asn Ile Pro Gly Thr Ser Glu Ser Ser Ala Phe Arg Phe Leu Phe Asn
    130                 135                 140

Leu Ser Ser Ile Pro Glu Asn Glu Val Ile Ser Ser Ala Glu Leu Arg
145                 150                 155                 160

Leu Phe Arg Glu Gln Val Asp Gln Gly Pro Asp Trp Glu Gln Gly Phe
                165                 170                 175

His Arg Ile Asn Ile Tyr Glu Val Met Lys Pro Pro Ala Glu Met Val
            180                 185                 190

Pro Gly His Leu Ile Thr Arg Leu Leu Asp Thr Arg Leu Val His His
        195                 200                 205
```

```
Asn Val Thr Arg Trp Glu Thr Phe Asp Val Ser Pro Ala Val Leu Arg
         210                 215                 220

Trp Thr Arg Glu Lys Gln Pro Asn Tyr Gly Leu Ala Ile Glu Val Thr
225                 230                 235                 240

His Leu His Gln Thr Arg Thr His Gln Gly Gln His Val Arg Ile Ser
             245                 250                 255

Arg Ser Leu Pro Gln Gly Ser Gly Asp Trp Ala Gln Leu Arg Pro Leu
         260                 265                 270

Leu Val Thr Phe Gly His Asp Gly Arg Gly His Thr Leu Thr Arg Arg
         275                 280                 285

Arg Ala Lys Arg Ser Pro Lys His His Pro Gln Arg Ser Arg Lys Lys
290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                 325                 330                 335

Cys His Gly Asp Cys Pro Phe Pro Leu Ala Asp His Leu Asn Ser Thr
             340                 345                 350

Asn His Ala Ile Val Gln Thr Leu Val Asn Ser Val Asn Ser Ser Ile
         355                 360                 365

Pro Lys Ala Cys Cys Val Pro Thr Glu Leu Ser Ala Ile Ser Met Leu
     370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405

(2) INFORMATION FOR SEQ ID NO:3:

(i) SEQUENCE CHARACTERISTICS:
        (A) LENGTH: 2688 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GAATTCGCTA GGTAGACCAG GCTGGCCCAG AACACCTAGA GATCATCTGG CTGCCTCTGT      60

CTCTTGAGTT CTGGGGCTAA AGCATGCACC ACTCTACCTG GCTAGTTTGT ATCCATCTAA     120

ATTGGGGAAG AAAGAAGTAC AGCTGTCCCC AGAGATAACA GCTGGGTTTT CCCATCAAAC     180

ACCTAGAAAT CCATTTTAGA TTCTAAATAG GGTTTGTCAG GTAGCTTAAT TAGAACTTTC     240

AGACTGGGTT TCACAGACTG GTTGGGCCAA AGGTCACTTT ATTGTCTGGG TTTCAGCAAA     300

ATGAGACAAT AGCTGTTATT CAAACAACAT TTGGGTAAGG AAGAAAAATG AACAAACACC     360

ACTCTCCCTC CCCCCGCTCC GTGCCTCCAA ATCCATTAAA GGCAAAGCTG CACCCCTAAG     420

GACAACGAAT CGCTGCTGTT TGTGAGTTTA AATATTAAGG AACACATTGT GTTAATGATT     480

GGAGCAGCAG TGATTGATGT AGTGGCATTG GTGAGCACTG AATCCGTCCT TCAACCTGCT     540

ATGGGAGCAC AGAGCCTGAT GCCCCAGGAG TAATGTAATA GAGTAATGTA ATGTAATGGA     600

GTTTTAATTT TGTGTTGTTG TTTTAAATAA TTAATTGTAA TTTTGGCTGT GTTAGAAGCT     660

GTGGGTACGT TTCTCAGTCA TCTTTTCGGT CTGGTGTTAT TGCCATACCT TGATTAATCG     720

GAGATTAAAA GAGAAGGTGT ACTTAGAAAC GATTTCAAAT GAAAGAAGGT ATGTTTCCAA     780

TGTGACTTCA CTAAAGTGAC AGTGACGCAG GGAATCAATC GTCTTCTAAT AGAAAGGGCT     840
```

| | |
|---|---|
| CATGGAGACC TGAGCTGAAT CTTTCTGTTC TGGATGAGAG AGGTGGTACC CATTGGAATG | 900 |
| AAAGGACTTA GTCAGGGGCA ATACAGTGTG CTCCAAGGCT GGGGATGGTC AGGATGTTGT | 960 |
| GCTCAGCCTC TAACACTCCT TCCAACCTGA CATTCCTTCT CACCCTTTGT CTCTGGCCAG | 1020 |
| TAGAATACAG GAACTCGTTC CTGTTTTTTT TTTTTTAAAT TCTGAAGGTG TGTAAGTACA | 1080 |
| AAGGTCAGAT GAGCGGCCCT AGGTCAAGAC TGCTTTGTGG TGACAAGGGA GTATAACACC | 1140 |
| CACCCCAGAA ACCAAGAACC GGAAATTGCT ATCTTCCAGC CCTTTGAGAG CTACCTGAAG | 1200 |
| CTCTGGGCTG CTGGCCTCAC CCCTTCCCTG CAGCTTTCCC TTTAGCAGAG GCTGTGATTT | 1260 |
| CCTTCAGCGC TTGGGCAAAT ACTCTTAGCC TGGCTCACCT TCCCCATCCT CGTTTGTAAA | 1320 |
| AACAAAGATG AAGCTGATAG TTCCTTCCCA GCTCCATCAG AGGCAGGGTG TGAAATTAGC | 1380 |
| TCCTGTTTGG GAAGGTTTAA AAGCCGGCCA CATTCCACCT CCCAGCTAGC ATGATTACCA | 1440 |
| ACTCTTGTTT CTTACTGTTG TTATGAAAGA CTCAATTCCT CATCTCCCTT TCCCTTCTTT | 1500 |
| TAAAAAGGGG CCAAAGGGCA CTTTGTTTTT TTCTCTACAT GGCCTAAAAG GCACTGTGTT | 1560 |
| ACCTTCCTGG AAGGTCCCAA ACAAACAAAC AAACAAACAA AATAACCATC TGGCAGTTAA | 1620 |
| GAAGGCTTCA GAGATATAAA TAGGATTTTC TAATTGTCTT ACAAGGCCTA GGCTGTTTGC | 1680 |
| CTGCCAAGTG CCTGCAAACT ACCTCTGTGC ACTTGAAATG TTAGACCTGG GGGATCGATG | 1740 |
| GAGGGCACCC AGTTTAAGGG GGGTTGGTGC AATTCTCAAA TGTCCACAAG AAACATCTCA | 1800 |
| CAAAAACTTT TTTGGGGGGA AAGTCACCTC CTAATAGTTG AAGAGGTATC TCCTTCGGGC | 1860 |
| ACACAGCCCT GCTCACAGCC TGTTTCAACG TTTGGGAATC CTTTAACAGT TTACGGAAGG | 1920 |
| CCACCCTTTA AACCAATCCA ACAGCTCCCT TCTCCATAAC CTGATTTTAG AGGTGTTTCA | 1980 |
| TTATCTCTAA TTACTCGGGG TAAATGGTGA TTACTCAGTG TTTTAATCAT CAGTTTGGGC | 2040 |
| AGCAGTTATT CTAAACTCAG GGAAGCCCAG ACTCCCATGG GTATTTTGG AAGGTACAGA | 2100 |
| GACTAGTTGG TGCATGCTTT CTAGTACCTC TTGCATGTGG TCCCCAGGTG AGCCCCGGCT | 2160 |
| GCTTCCCGAG CTGGAGGCAT CGGTCCCAGC CAAGGTGGCA ACTGAGGGCT GGGGAGCTGT | 2220 |
| GCAATCTTCC GGACCCGGCC TTGCCAGGCG AGGCGAGGCC CCGTGGCTGG ATGGGAGGAT | 2280 |
| GTGGGCGGGG CTCCCCATCC CAGAAGGGGA GGCGATTAAG GGAGGAGGGA AGAAGGGAGG | 2340 |
| GGCCGCTGGG GGGAAAGACT GGGGAGGAAG GGAAGAAAGA GAGGGAGGGA AAAGAGAAGG | 2400 |
| AAGGAGTAGA TGTGAGAGGG TGGTGCTGAG GGTGGGAAGG CAAGAGCGCG AGGCCTGGCC | 2460 |
| CGGAAGCTAG GTGAGTTCGG CATCCGAGCT GAGAGACCCC AGCCTAAGAC GCCTGCGCTG | 2520 |
| CAACCCAGCC TGAGTATCTG GTCTCCGTCC CTGATGGGAT TCTCGTCTAA ACCGTCTTGG | 2580 |
| AGCCTGCAGC GATCCAGTCT CTGGCCCTCG ACCAGGTTCA TTGCAGCTTT CTAGAGGTCC | 2640 |
| CCAGAAGCAG CTGCTGGCGA GCCCGCTTCT GCAGGAACCA ATGGTGAG | 2688 |

(2) INFORMATION FOR SEQ ID NO:4:

(i) SEQUENCE CHARACTERISTICS:
        (A) LENGTH: 2875 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

| | |
|---|---|
| GAATTCATTT AAGCTGGATT CACTTCTAGG TCCCATGCGT TTACACTCAT TTCCACCACA | 60 |
| AGAGGGCAGC CATCTCTAAA AAAACAACAG TCGAGTGCTC TTCAGAGAAA TTGGGCCAAA | 120 |

```
CTTGAGGAAA GTTCCTGGGA AAGGCTTTTT AGCAGCACCT CTCTGGGCTA CAAAAAAGAA      180

GCCAGCAGGC ACCACCAAGG TGGAGTAACT GTCCAGAGGC ATCCATTTTA CCTCAGAGAC      240

TTGATTACTA AGGATATCCT AAACGGCCAA ACTCTCTCTT CTGGTGTTCC AGAGGCCCAA      300

AGCTGCAAGG CATTGTTGAT GTCATCACCA AAGGTTTCAT TTTCATCTTT TCTTGGGGTT      360

GGTCCAACAG CTGTCAGCTT TCTCTTCCTC ATTAAAGGCA ACTTTCTCAT TTAAATCTCA      420

TATAGGTTCG GAGTTTCTTG CTTTGCTCCT TCCGCCTCCG CGATGACAGA AGCAATGGTT      480

AACTTCTCAA TTAAACTTGA TAGGGAAGGA AATGGCTTCA GAGGCGATCA GCCCTTTTGA      540

CTTACACACT TACACGTCTG AGTGGAGTGT TTTATTGCCG CCTTGTTTGG TGTCTCATGA      600

TTCAGAGTGA CAACTTCTGC AACACGTTTT AAAAAGGAAT ACAGTAGCTG ATCGCAAATT      660

GCTGGATCTA TCCCTTCCTC TCCTTTAATT TCCCTTGTAG ACAGCCTTCC TTCAAAAATA      720

CCTTATTTGA CCTCTACAGC TCTAGAAACA GCCAGGGCCT AATTTCCCTC TGTGGGTTGC      780

TAATCCGATT TAGGTGAACG AACCTAGAGT TATTTTAGCT AAAAGACTGA AAAGCTAGCA      840

CACGTGGGTA AAAAAATCAT TAAAGCCCCT GCTTCTGGTC TTTCTCGGTC TTTGCTTTGC      900

AAACTGGAAA GATCTGGTTC ACAACGTAAC GTTATCACTC TGGTCTTCTA CAGGAATGCT      960

CAGCCCATAG TTTTGGGGGT CCTGTGGGTA GCCAGTGGTG GTACTATAAG GCTCCTGAAT     1020

GTAGGGAGAA ATGGAAAGAT TCAAAAAAGA ATCCTGGCTC AGCAGCTTGG GGACATTTCC     1080

AGCTGAGGAA GAAAACTGGC TTGGCCACAG CCAGAGCCTT CTGCTGGAGA CCCAGTGGAG     1140

AGAGAGGACC AGGCAGAAAA TTCAAAGGTC TCAAACCGGA ATTGTCTTGT TACCTGACTC     1200

TGGAGTAGGT GGGTGTGGAA GGGAAGATAA ATATCACAAG TATCGAAGTG ATCGCTTCTA     1260

TAAAGAGAAT TTCTATTAAC TCTCATTGTC CCTCACATGG ACACACACAC ACACACACAC     1320

ACACACACAC ACACATCACT AGAAGGGATG TCACTTTACA AGTGTGTATC TATGTTCAGA     1380

AACCTGTACC CGTATTTTTA TAATTTACAT AAATAAATAC ATATAAAATA TATGCATCTT     1440

TTTATTAGAT TCATTTATTT GAATATAAAT GTATGAATAT TTATAAAATG TAATAATGCA     1500

CTCAGATGTG TATCGGCTAT TTCTCGACAT TTTCTTCTCA CCATTCAAAA CAGAAGCGTT     1560

TGCTCACATT TTTGCCAAAA TGTCTAATAA CTTGTAAGTT CTGTTCTTCT TTTTAATGTG     1620

CTCTTACCTA AAAACTTCAA ACTCAAGTTG ATATTGGCCC AATGAGGGAA CTCAGAGGCC     1680

AGTGGACTCT GGATTTGCCC TAGTCTCCCG CAGCTGTGGG CGCGGATCCA GGTCCCGGGG     1740

GTCGGCTTCA CACTCATCCG GGACGCGACC CCTTAGCGGC CGCGCGCTCG CCCCGCCCCG     1800

CTCCACCGCG GCCCCGTACG CGCCGTCCAC ACCCCTGCGC GCCCGTCCCG CCCGCCCGGG     1860

GGATCCCGGC CGTGCTGCCT CCGAGGGGGA GGTGTTCGCC ACGGCCGGGA GGGAGCCGGC     1920

AGGCGGCGTC TCCTTTAAAA GCCGCGAGCG CGCGCCAGCG CGGCTCGTCG CCGCCGGAGT     1980

CCTCGCCCTG CCGCGCAGAG CCCTGCTCGC ACTGCGCCCG CCGCGTGCGC TTCCCACAGC     2040

CCGCCCGGGA TTGGCAGCCC CGGACGTAGC CTCCCCAGGC GACACCAGGC ACCGGGACGC     2100

CCTCCCGGCG AAAGACGCGA GGGTCACCCG CGGCTTCGAG GGACTGGCAC GACACGGGTT     2160

GGAACTCCAG ACTGTGCGCG CCTGGCGCTG TGGCCTCGGC TGTCCGGGAG AAGCTAGAGT     2220

CGCGGACCGA CGCTAAGAAC CGGGAGTCCG GAGCACAGTC TTACCCTCAA TGCGGGGCCA     2280

CTCTGACCCA GGAGTGAGCG CCCAAGGCGA TCGGGCGGAA GAGTGAGTGG ACCCCAGGCT     2340

GCCACAAAAG ACACTTGGCC CGAGGGCTCG GAGCGCGAGG TCACCCGGTT TGGCAACCCG     2400

AGACGCGCGG CTGGACTGTC TCGAGAATGA GCCCCAGGAC GCCGGGGCGC CGCAGCCGTG     2460
```

-continued

```
CGGGCTCTGC TGGCGAGCGC TGATGGGGGT GCGCCAGAGT CAGGCTGAGG GAGTGCAGAG    2520

TGCGGCCCGC CCGCCACCCA AGATCTTCGC TGCGCCCTTG CCCGGACACG GCATCGCCCA    2580

CGATGGCTGC CCCGAGCCAT GGGTCGCGGC CCACGTAACG CAGAACGTCC GTCCTCCGCC    2640

CGGCGAGTCC CGGAGCCAGC CCCGCGCCCC GCCAGCGCTG GTCCCTGAGG CCGACGACAG    2700

CAGCAGCCTT GCCTCAGCCT TCCCTTCCGT CCCGGCCCCG CACTCCTCCC CCTGCTCGAG    2760

GCTGTGTGTC AGCACTTGGC TGGAGACTTC TTGAACTTGC CGGGAGAGTG ACTTGGGCTC    2820

CCCACTTCGC GCCGGTGTCC TCGCCCGGCG GATCCAGTCT TGCCGCCTCC AGCCC         2875
```

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
CCCGGCAAGT TCAAGAAG                                                    18
```

(2) INFORMATION FOR SEQ ID NO:6:

(i) SEQUENCE CHARACTERISTICS:
        (A) LENGTH: 15144 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
GAATTCATTT AAGCTGGATT CACTTCTAGG TCCCATGCGT TTACACTCAT TTCCACCACA      60

AGAGGGCAGC CATCTCTAAA AAAACAACAG TCGAGTGCTC TTCAGAGAAA TTGGGCCAAA     120

CTTGAGGAAA GTTCCTGGGA AAGGCTTTTT AGCAGCACCT CTCTGGGCTA CAAAAAAGAA     180

GCCAGCAGGC ACCACCAAGG TGGAGTAACT GTCCAGAGGC ATCCATTTTA CCTCAGAGAC     240

TTGATTACTA AGGATATCCT AAACGGCCAA ACTCTCTCTT CTGGTGTTCC AGAGGCCCAA     300

AGCTGCAAGG CATTGTTGAT GTCATCACCA AAGGTTTCAT TTTCATCTTT TCTTGGGGTT     360

GGTCCAACAG CTGTCAGCTT TCTCTTCCTC ATTAAAGGCA ACTTTCTCAT TTAAATCTCA     420

TATAGGTTCG GAGTTTCTTG CTTTGCTCCT TCCGCCTCCG CGATGACAGA AGCAATGGTT     480

AACTTCTCAA TTAAACTTGA TAGGGAAGGA AATGGCTTCA GAGGCGATCA GCCCTTTTGA     540

CTTACACACT TACACGTCTG AGTGGAGTGT TTTATTGCCG CCTTGTTTGG TGTCTCATGA     600

TTCAGAGTGA CAACTTCTGC AACACGTTTT AAAAAGGAAT ACAGTAGCTG ATCGCAAATT     660

GCTGGATCTA TCCCTTCCTC TCCTTTAATT TCCCTTGTAG ACAGCCTTCC TTCAAAAATA     720

CCTTATTTGA CCTCTACAGC TCTAGAAACA GCCAGGGCCT AATTTCCCTC TGTGGGTTGC     780

TAATCCGATT TAGGTGAACG AACCTAGAGT TATTTTAGCT AAAAGACTGA AAAGCTAGCA     840

CACGTGGGTA AAAAAATCAT TAAAGCCCCT GCTTCTGGTC TTTCTCGGTC TTTGCTTTGC     900

AAACTGGAAA GATCTGGTTC ACAACGTAAC GTTATCACTC TGGTCTTCTA CAGGAATGCT     960

CAGCCCATAG TTTTGGGGGT CCTGTGGGTA GCCAGTGGTG GTACTATAAG GCTCCTGAAT    1020

GTAGGGAGAA ATGGAAAGAT TCAAAAAAGA ATCCTGGCTC AGCAGCTTGG GGACATTTCC    1080

AGCTGAGGAA GAAAACTGGC TTGGCCACAG CCAGAGCCTT CTGCTGGAGA CCCAGTGGAG    1140
```

```
AGAGAGGACC AGGCAGAAAA TTCAAAGGTC TCAAACCGGA ATTGTCTTGT TACCTGACTC      1200

TGGAGTAGGT GGGTGTGGAA GGGAAGATAA ATATCACAAG TATCGAAGTG ATCGCTTCTA      1260

TAAAGAGAAT TTCTATTAAC TCTCATTGTC CCTCACATGG ACACACACAC ACACACACAC      1320

ACACACACAC ACACATCACT AGAAGGGATG TCACTTTACA AGTGTGTATC TATGTTCAGA      1380

AACCTGTACC CGTATTTTTA TAATTTACAT AAATAAATAC ATATAAAATA TATGCATCTT      1440

TTTATTAGAT TCATTTATTT GAATATAAAT GTATGAATAT TTATAAAATG TAATAATGCA      1500

CTCAGATGTG TATCGGCTAT TTCTCGACAT TTTCTTCTCA CCATTCAAAA CAGAAGCGTT      1560

TGCTCACATT TTTGCCAAAA TGTCTAATAA CTTGTAAGTT CTGTTCTTCT TTTTAATGTG      1620

CTCTTACCTA AAAACTTCAA ACTCAAGTTG ATATTGGCCC AATGAGGGAA CTCAGAGGCC      1680

AGTGGACTCT GGATTTGCCC TAGTCTCCCG CAGCTGTGGG CGCGGATCCA GGTCCCGGGG      1740

GTCGGCTTCA CACTCATCCG GGACGCGACC CCTTAGCGGC CGCGCGCTCG CCCCGCCCCG      1800

CTCCACCGCG GCCCCGTACG CGCCGTCCAC ACCCCTGCGC GCCCGTCCCG CCCGCCCGGG      1860

GGATCCCGGC CGTGCTGCCT CCGAGGGGGA GGTGTTCGCC ACGGCGGGA GGGAGCCGGC       1920

AGGCGGCGTC TCCTTTAAAA GCCGCGAGCG CGCGCCAGCG CGGCGTCGTC GCCGCCGGAG      1980

TCCTCGCCCT GCCGCGCAGA GCCCTGCTCG CACTGCGCCC GCCGCGTGCG CTTCCCACAG      2040

CCCGCCCGGG ATTGGCAGCC CCGGACGTAG CCTCCCCAGG CGACACCAGG CACCGGAGCC      2100

CCTCCCGGCA AAAGACGCGA GGGTCACCCG CGGCTTCGAG GGACTGGCAC GACACGGGTT      2160

GGAACTCCAG ACTGTGCGCG CCTGGCGCTG TGGCCTCGGC TGTCCGGGAG AAGCTAGAGT      2220

CGCGGACCGA CGCTAAGAAC CGGGAGTCCG GAGCACAGTC TTACCCTCAA TGCGGGGCCA      2280

CTCTGACCCA GGAGTGAGCG CCCAAGGCGA TCGGGCGGAA GAGTGAGTGG ACCCCAGGCT      2340

GCCACAAAAG ACACTTGGCC CGAGGGCTCG GAGCGCGAGG TCACCCGGTT TGGCAACCCG      2400

AGACGCGCGG CTGGACTGTC TCGAGAATGA GCCCCAGGAC GCCGGGCGC CGCAGCCGTG       2460

CGGGCTCTGC TGGCGAGCGC TGATGGGGGT GCGCCAGAGT CAGGCTGAGG GAGTGCAGAG      2520

TGCGGCCCGC CCGCCACCCA AGATCTTCGC TGCGCCCTTG CCCGGACACG GCATCGCCCA      2580

CGATGGCTGC CCCGAGCCAT GGGTCGCGGC CCACGTAACG CAGAACGTCC GTCCTCCGCC      2640

CGGCGAGTCC CGGAGCCAGC CCCGCGCCCC GCCAGCGCTG GTCCCTGAGG CCGACGACAG      2700

CAGCAGCCTT GCCTCAGCCT TCCCTTCCGT CCCGGCCCCG CACTCCTCCC CCTGCTCGAG      2760

GCTGTGTGTC AGCACTTGGC TGGAGACTTC TTGAACTTGC CGGGAGAGTG ACTTGGGCTC      2820

CCCACTTCGC GCCGGTGTCC TCGCCCGGCG GATCCAGTCT TGCCGCCTCC AGCCCGATCA      2880

CCTCTCTTCC TCAGCCCGCT GGCCCACCCC AAGACACAGT TCCCTACAGG GAGAACACCC      2940

GGAGAAGGAG GAGGAGGCGA AGAAAAGCAA CAGAAGCCCA GTTGCTGCTC CAGGTCCCTC      3000

GGACAGAGCT TTTTCCATGT GGAGACTCTC TCAATGGACG TGCCCCCTAG TGCTTCTTAG      3060

ACGGACTGCG GTCTCCTAAA GGTAGAGGAC ACGGGCCGGG GACCCGGGGT TGGCTGGCGG      3120

GTGACACCGC TTCCCGCCCA ACGCAGGGCG CCTGGGAGGA CTGGTGGAGT GGAGTGGACG      3180

TAAACATACC CTCACCCGGT GCACGTGCAG CGGATCCCTA GAGGGGTTAG GCATTCCAAA      3240

CCCCAGATCC CTCTGCCTTG CCCACTGGCC TCCTTCCTCC AGCCGGTTCC TCCTCCCCAA      3300

GTTTTCGATA CATTATAAGG GCTGTTTTGG GCTTTCAAAA AAAAAAATGC AGAAATCCAT      3360

TTAAGAGTAT GGCCAGTAGA TTTTACTAGT TCATTGCTGA CCAGTAAGTA CTCCAAGCCT      3420

TAGAGATCCT TGGCTATCCT TAAGAAGTAG GTCCATTTAG GAAGATACTA AAAGTTGGGG      3480
```

```
TTCTCCATGT GTGTTTACTG ACTATGCGAA TGTGTCATAG CTTACACGTG CATTCATAAA    3540

CACTATCTAT TTAGTTAATT GCAGGAAGGT GCATGGATTT CTTGACTGCA CAGGAGTCTT    3600

GGGGAAGGGG GAACAGGGTT GCCTGTGGGT CAACCTTAAA TAGTTAGGGC GAGGCCACAA    3660

CTTGCAAGTG GCGTCATTAG CAGTAATCTT GAGTTTAGCG CTTACTGAAT CTACAAGTTT    3720

GATATGCTCA ACTACCAGGA AATTGTATAC AGCGCCTCTA AGGAAGTCAC TTGTGCATTT    3780

GTGTCTGTTA ATATGCACAT GAGGCTGCAC TGTATAAGTT TGTCAGGGAT GCAGTGTCCG    3840

ACCAACCTAT GGCTTCCCAG CTTCCTGACA CCCGCATTCC CAGCTAGTGT CACAAGAAAA    3900

GGGTACAGAC GGTCAAGCTC TTTTTAATTG GGAGTTAAGA CCAAGCCCCA AGTAAGAAGT    3960

CCGGCTGGGA CTTGGGGGTC CTCCATCGGC CAGCGAGCTC TATGGGAGCC GAGGCGCGGG    4020

GGCGGCGGAG GACTGGGCGG GGAACGTGGG TGACTCACGT CGGCCCTGTC CGCAGGTCGA    4080

CCATGGTGGC CGGGACCCGC TGTCTTCTAG TGTTGCTGCT TCCCCAGGTC CTCCTGGGCG    4140

GCGCGGCCGG CCTCATTCCA GAGCTGGGCC GCAAGAAGTT CGCCGCGGCA TCCAGCCGAC    4200

CCTTGTCCCG GCCTTCGGAA GACGTCCTCA GCGAATTTGA GTTGAGGCTG CTCAGCATGT    4260

TTGGCCTGAA GCAGAGACCC ACCCCCAGCA AGGACGTCGT GGTGCCCCCC TATATGCTAG    4320

ATCTGTACCG CAGGCACTCA GGCCAGCCAG GAGCGCCCGC CCCAGACCAC CGGCTGGAGA    4380

GGGCAGCCAG CCGCGCCAAC ACCGTGCGCA CGTTCCATCA CGAAGGTGAG CGGGCGGCGG    4440

GTGGCGGGGC GGGGACGGCG GGCGGGCGGA GACTAGGCGG GCAGCCCGGG CCTCCACTAG    4500

CACAGTAGAA GGCCTTTCGG CTTCTGTACG GTCCCCTCTG TGGCCCCAGC CAGGGATTCC    4560

CCGCTTGTGA GTCCTCACCC TTTCCTGGCA AGTAGCCAAA AGACAGGCTC CTCCCCCTAG    4620

AACTGGAGGG AAATCGAGTG ATGGGGAAGA GGGTGAGAGA CTGACTAGCC CCTAGTCAGC    4680

ACAGCATGCG AGATTTCCAC AGAAGGTAGA GAGTTGGAGC TCCTTAAATC TGCTTGGAAG    4740

CTCAGATCTG TGACTTGTGT TCACGCTGTA GTTTTAAGCT AGGCAGAGCA AGGGCAGAAT    4800

GTTCGGAGAT AGTATTAGCA AATCAAATCC AGGGCCTCAA AGCATTCAAA TTTACTGTTC    4860

ATCTGGGCCT AGTTTGAAAG ATTTCTGAAT CCCTATCTAA TCCCCGTGGG AGATCAATTC    4920

CACAATTCGT CATATTGTTT CCACAATGAC CTTCGATTCT TTGCTTAAAT CTTAAATCTC    4980

CAAGTGGAGA CAGCGCAACG CTTCAGATAA AAGCCTTTCT CCCACTGCCT GCTACCTTCC    5040

TAGGCAAGGC AATGGGGTTT TTAAACAAAT ATATGAATAT GATTTCCCAA GATAGAATAA    5100

TGTTGTTTAT TTCAGCTGAA ATTTCCTGGA TTAGAAAGGC TGTAGAGGCC TATTGAAGTC    5160

TCTTGCACCG ATGTTCTGAA AGCAGTTAGT AAAAAATCAT GACCTAGCTC AATTCTGTGT    5220

GTGCCACTTT CAATGTGCTT TTGACTTAAT GTATTCTCCA TAGAACATCA GTTCCTTCAA    5280

GTTCTAGAAG AATTCAGATT TAAAGTTTTG CTTTGCCTTG CTGAGGGGAT AAATTTTAAG    5340

TAGAAATCTA GGCTCTGAAA TGATAGCCCA ACCCCATCTC CAGTAAGGGA TGACTGACTC    5400

AAACCTTGAG AAGTCTGGGT GATAATAGGA AAAGTCCACA AGCAGGTCAC AGAGCGCGAG    5460

ATGGATCTGT CTTGAGGCAG CCAATGGTTA TGAAGGGCAC TGGAAATCCA TCTCTTTCAA    5520

ACTGGTGTCT AGGGCTTTCT GGGAGCAAAG CTTAGACCAC ATTCTGCTCC TCAAGGTTTG    5580

CCTACTGAAA GCAGGGAGAT TCTGGGTGTT CACCCCCATC CTTCACCCCC AGGTGATTCT    5640

GGGCTTAGCT AATCTCTCCT GGTTAATATT CATTGGAAAG TTTTTATAGA TCAAAACAAA    5700

CAAACCTACT ATCCAGCACA GGTGTTTTTC CCACTGCCTC TGGAGATATA GCAAGAAAAC    5760

CATATATTCA TGTATTTCCT TATTAGTCTT TTCTAACGTG AAAATTATTC CTGACCTATA    5820

AAAAATGAAG GAGGTATTTT ATCTTAACTA AGCTAAAAGA ATCGCTTAAG TCAATTGAAA    5880
```

```
CTCAAAAATC CAATTGAATG AAAGGTTCGT CAATAAAAAT CTACATTTTT CTTACTCTTC    5940

CTTTGGAAAT AGCTTGATAA AAACACAGAC AAAACAAAGT CTGTGTGCTT ATTTGAAAAC    6000

TTAGTGAGCT TCAGTTCATA AGCAAAAAAT GTAGTTTAAA AGTGATTTTT CTGTTGTAAA    6060

ACGTGATAGA AGTTATTGAC TTGTTTAAAA TAAACTTGCA CTAACTTTAT ACCTTGGTGC    6120

AATTAGATGT AATGTTTACT GTAAATTTCA GGAAAACCAT TTTTTTTTTT TGGTCATGAT    6180

CAGGTACACA TGGCATTTGG GAAGACTTTT CACATTGTTG AGTAACCTAG AGTTTGTTTG    6240

TTTGTTTGTT TGTTTTTAAG CATTCTTGTG CCACTAGAAA AACCTTAATA AGCCATGTGT    6300

TACTTGGTAG ACTTCTTCCT AAGTTCTAGA AAGTGGCTTA ATGCCACGAT GAGACAAAAC    6360

ATACCATAGT AGTCTTTCAA CCAGTGGCAG AGTCTTCCAG ACAAAATCTC CTGTTGAACA    6420

TTAAGACCAT GGATTTTTAT CCAGGAGAGC CCAGGCTTTG CTGAATCACC ACCCTCCAAC    6480

CCCACTCCAA GGTCACCGAA GGCCTCCCCA ACTGGCTGCC ATTGAGAAAC TGTTTGAAAT    6540

TGATTGACTC CATTGGCCCT ACAGAGACTT CTCCTTTAGT GGCAGATCAT ATACTGAAGG    6600

ATCCAAGCTT GCTCTTCTGA CTATGAAGAG CACAGTCTTT CTTTTTCTTT ATGGAATAAA    6660

CAAACTATGT GGCCCTGTGA CTAAAGTTTT CAAAGAGGGA GAGATCCTGT TAGCAGAAGT    6720

GCAACTGCCC AGAAACTAGC CACAGGCTAG GATATTCCAA AGTACAACTC TAAAGTATGG    6780

TCCATCCTAA ATTCTAGCAT GGGGTTGAAT ACCGGCATCC AGGAATACTT CTCTCTACCT    6840

CTGGCTATTG CAGTGAGATT ACGAAGACCC TGGGGGAAA AACAGTTGCT TAGTTTACAG    6900

ATGTTCCTTG CCACAGATGT TCTCAGTATC TCTTGTTTGT CAGAGGATCC TTTCAATCCC    6960

TCTTGACATT TCCAATCTGC TTTTGTCCTC TCTACATGTG CCTTGTGGCA TTTCGCTTGG    7020

TCTTTAGAGA ATCCCTTTCT GGAGCTGCAG GTTCCCTTGT AGGATCTGTG TTCAGGAGAA    7080

CAGGGACCTT GGCAGGTTAG TGACAACTAC CAAACCCTGC TTTCCTTCCC TGCCACTTCC    7140

TTTGTTGCCT TAAAAATTAA ACCTTAACTC TCTGTGTCTA AACCTTTTCT TCTTCCTCTT    7200

TGTCATTTAC TTTATTTATT TGTCATGTAC TTTATCCTGT AGAAAATCAC AGTGTGGCCC    7260

AAAGCCCCTT GAATCTTGTT GCAGCGGTGA GATGCAGCTG CTGATCTGGA ATAGCCTTAG    7320

GCTGTGTGTT TGATCACAAT GCTTTCTGTC CAAAAGTGTG CAAATCCTCC AAGCTTAATG    7380

ATAACTTTTG AAATGAAACT CACCCTACTT TAGGGCAAAC AAGTAGCCAC AGAGAGCAGG    7440

ATCTAAACAA GGTCTGGTGT CCCATTTGGC TGTGTCCCTT CAATTTTCTG TTCATTTAGC    7500

TCTGTCTGCA TCTAAAGGGT GCTGGGCAAT AAGTTTTGAT CTTCAGGGCA AAACTCAATC    7560

TTCAGTTACC ATGGTATCAG GTACCAATTC CTAGTGATTT GTGCTATGGC TTAGGATTTG    7620

ATTTCTCTCC TACATTAGGT AATATCTTTC AATGGCTAGA ACTTGGGCAT TGCAGTACAC    7680

TCAAGTTAAC AGTTCTGTGA CCTAAGGAAG TCACATAACC TCTCTGAATT CTCTACTGTT    7740

TCATTCACAA AATGGAGAAA ATCATGGCTC TTTCTTAATG TGCGAATTCA TAGAAAGGTG    7800

ATGACACCAG ATTTGGCAGA AGGAAGGAAA GGAAGGAAGG AAGAAAGAAA GAAAGAAAGA    7860

AAGAAAGAAA GAAAGAAAGA AAGAAAGAAA GGAAGGAAGG GAGAGAGAGA GAAGGGAAGG    7920

GAAAGGGAAA GGGAAAGGAA AGAAAAGAAA GGAAGGAAGA AAAGGAAGGA AGGAAGGAAA    7980

GAAGGAAGGA AGGAAAAGAA AGAGAAGAAA GCATTCAGCA TATGAACTAA TGTTTCCTGG    8040

TGACTTTTTA TATCATATCC TTGTTCTAGG AAGTGGCCCT AGCCATATCT TTTGGGTTAT    8100

TTTGAGGTAG AGGATAATCA ACATAGTGTA GAACATTAAA TCTGGGTTTT GTTTCTAGAA    8160

GAGGCTAGAA TGGCATGGCT GTCCCACTTG CTCCTCTTTC AGGCAGTATG GCAGCCACCA    8220
```

-continued

```
TTCTCTCTGT AAGATCTAGG AGGCTGACAC TCAGGTTGGA GACAGGTCAG AATCCTGAAA    8280

TCACTTAGCA AGTTCAGCTG ATTCAACAAG GGATATTTAC AGAGAATTAA CAGCTATTCC    8340

AGCTTCCAAA AAGTGTACAT TACCTACTCT GTATTTTCAG AACCCCAGGT TTGCTGTGAT    8400

AATTTGGTAG AAGCCTTTTC CTGTAATTTT CTTTATTTAA AAGATATTTT CATTTTCCAC    8460

CCTCAAGAAG AGGTTGAAAC TTGTCCCTTG AAGTAGAAGA GGTGTTGTGT GTCCTGACCC    8520

TGAGGAAGTT GGCCTTGTTG AGGTCTTCTG TAAATTCTTG AATTCTCTGT ATAATTTCAA    8580

TGAATAGTCA TGTTTGATAC CTTGGTATAA AGGATGGGAT AAGATCTTTC AAGGCTTAGG    8640

CTGATGGAAA CGCTGCTGAA AGACTAGAGA TTGCTCTTTC CTTTGGCATC TGTCTTGGGT    8700

AGTAATATTG TTCTCTGTGA AGGCCCACTT ATTCTGTCTT GAAAATTCTT CTTACCTCCA    8760

GAGTGATAGG CCACAGGGAG TACTGTTTCT ATGTTTGCAG TTGAAAGATG ACAATTTCAT    8820

ATGGTCCAAA CTTGGCTTTA TTTCTTGGTG AGATATTATT CTGTTACTTC AATGACCTGT    8880

CTCCATTATT TATCTTGAGG CTCACCTCTT CCCTTTTGTT GACTGTTGTG CAATTTGTGG    8940

AAGGCCCTGG GTAGTCAGCC TTTATACTCT GTCTGTACAG GAAATAAAGT GCATGTCACC    9000

ATGCCAAAGT CAGGAGATGC CGGTGTGATT AGGGTCCACG GGATTTTGCT ACTGTTTTTA    9060

TTTCTATCGA TGAATTGCCT TAGGCAGAAA CATTAAGGGA CACCAGAATG GTGATGAAAG    9120

GCTTTTTATA ACAGAAGCTA AATGCAGTCC TTCATACTTC ATGGAATGCC CCTGTCCTAA    9180

AGTACCATTA ACCGATAGTG GAGTCAGAAC ATAAATGGCT CCCCAAAGGT ATCACCAAGA    9240

ACTTTTGGCA AACAGATGCA AGAGGATTAT GAAGAATCGC AGCTTGGTCT GGTAATCTTC    9300

CTGTTGCAAA GAGAAGAGCT TTAGAAGACC CCCCTTGAGT CCCTGGCTGG CTTAACATAG    9360

CATGAACCCT CATGTGTTGG CCAACATTAA GGCTTTTTCT ATAAAAGTCT CCTCCTTCAT    9420

CAGTATACGC TCGAGTATGA AAAGCATCCT TTTAAACCTT GACTCTGTGT GGTCCAGAAA    9480

CAGCAGCATC CCTTGCTTAA GAGCTTAATG GAGATGCAGG AGTGCAGGCC TCTTCCCAGA    9540

CCGGCTGATG TGCAGGTCAA AGTCTAAGCA CTGCTGGATC AACACAGAAG TTATTCCGAA    9600

TGAGGATGAG ATGGATACGA GAGAACAGGA AGTAGGAAGG GATTTCTTTA TCGTGAATTG    9660

CTACAGCAGC CTAATGTCAC CCCATACCCT TCTGAAGAAC TATGTCCCTG TGGATGCCTT    9720

TGTCTCTAGA GTTCTGAGCA AAATGGTAGG GTGTGCTTTG CAAAATGTCA TCATTGATGT    9780

TGAATTTCAA AGTCTTTAAT TAAGGGGCTG AAATCTGTAT ATTGAGATTT GTAAATCATC    9840

TAAATTGTAG AGTAATGTTT GCACAGGCTG CTTAAGGGAT TGACATTAAA GCTCGTTTTC    9900

TTAGTTAAGA AATACAGTCA TTTCCTCAAC TCCTCAGTCA TTAGCTCTCT ACTAAGTACA    9960

GTGCTGACTT TTTTAAAATT AAAGTCTGTG AATTCCAAAG AAGTGTTTCA CTATTTCCTC   10020

CATTATTATA GCTACCTAGA AGCTATGTTC ATATATTGGA TTAAAAACGT AGCAATTACA   10080

AAGTTAATGT GGCCATATAG AAAAGGGAAA AGAAACTCCG CTTTCACTTT AATATATATA   10140

TGTGTGTGTG TATATCATAT ATATACATGT TGTGTGTGTA TATATATATA TATATATATA   10200

TATATATATA TATATATATA TATATATATA TGTTGTGTTA AGCAGTAAAC TCAGGCCATG   10260

GACAGAGGGG CAGACATTGT ATCTCTAGGC CTGACATTTT TAATTTCTGG TTGCAGGTTT   10320

TTATGTAGTT TAACTTAAAC CATGCACTGA AGTTTTAAAT GCTCGTAAGG AATTAAGTTA   10380

CCATTGGCTC TCTTACCAAA TGCGTTTCTT TTTTCTCTCC ACCCTGATCA AACTAGAAGC   10440

CGTGGAGGAA CTTCCAGAGA TGAGTGGGAA AACGGCCCGG CGCTTCTTCT TCAATTTAAG   10500

TTCTGTCCCC AGTGACGAGT TTCTCACATC TGCAGAACTC CAGATCTTCC GGGAACAGAT   10560

ACAGGAAGCT TTGGGAAACA GTAGTTTCCA GCACCGAATT AATATTTATG AAATTATAAA   10620
```

-continued

```
GCCTGCAGCA GCCAACTTGA AATTTCCTGT GACCAGACTA TTGGACACCA GGTTAGTGAA    10680

TCAGAACACA AGTCAGTGGG AGAGCTTCGA CGTCACCCCA GCTGTGATGC GGTGGACCAC    10740

ACAGGGACAC ACCAACCATG GGTTTGTGGT GGAAGTGGCC CATTTAGAGG AGAACCCAGG    10800

TGTCTCCAAG AGACATGTGA GGATTAGCAG GTCTTTGCAC CAAGATGAAC ACAGCTGGTC    10860

ACAGATAAGG CCATTGCTAG TGACTTTTGG ACATGATGGA AAAGGACATC CGCTCCACAA    10920

ACGAGAAAAG CGTCAAGCCA ACACAAACA GCGGAAGCGC CTCAAGTCCA GCTGCAAGAG    10980

ACACCCTTTG TATGTGGACT TCAGTGATGT GGGGTGGAAT GACTGGATCG TGGCACCTCC    11040

GGGCTATCAT GCCTTTTACT GCCATGGGGA GTGTCCTTTT CCCCTTGCTG ACCACCTGAA    11100

CTCCACTAAC CATGCCATAG TGCAGACTCT GGTGAACTCT GTGAATTCCA AAATCCCTAA    11160

GGCATGCTGT GTCCCCACAG AGCTCAGCGC AATCTCCATG TTGTACCTAG ATGAAAATGA    11220

AAAGGTTGTG CTAAAAAATT ATCAGGACAT GGTTGTGGAG GGCTGCGGGT GTCGTTAGCA    11280

CAGCAAGAAT AAATAAATAA ATATATATAT TTTAGAAACA GAAAAAACCC TACTCCCCCT    11340

GCCTCCCCCC CAAAAAAACC AGCTGACACT TTAATATTTC CAATGAAGAC TTTATTTATG    11400

GAATGGAATG AAAAAAACAC AGCTATTTTG AAAATATATT TATATCGTAC GAAAAGAAGT    11460

TGGGAAAACA AATATTTTAA TCAGAGAATT ATTCCTTAAA GATTTAAAAT GTATTTAGTT    11520

GTACATTTTA TATGGGTTCA ACTCCAGCAC ATGAAGTATA AGGTCAGAGT TATTTTGTAT    11580

TTATTTACTA TAATAACCAC TTTTTAGGGA AAAAGATAG TTAATTGTAT TTATATGTAA    11640

TCAGAAGAAA TATCGGGTTT GTATATAAAT TTTCCAAAAA AGGAAATTTG TAGTTTGTTT    11700

TTCAGTTGTG TGTATTTAAG ATGCAAAGTC TACATGGAAG GTGCTGAGCA AAGTGCTTGC    11760

ACCACTTGCT GTCTGTTTCT TGCAGCACTA CTGTTAAAGT TCACAAGTTC AAGTCCAAAA    11820

AAAAAAAAAA AGGATAATCT ACTTTGCTGA CTTTCAAGAT TATATTCTTC AATTCTCAGG    11880

AATGTTGCAG AGTGGTTGTC CAATCCGTGA GAACTTTCAT TCTTATTAGG GGGATATTTG    11940

GATAAGAACC AGACATTACT GATCTGATAG AAAACGTCTC GCCACCCTCC CTGCAGCAAG    12000

AACAAAGCAG GACCAGTGGG AATAATTACC AAAACTGTGA CTATGTCAGG AAAGTGAGTG    12060

AATGGCTCTT GTTCTTTCTT AAGCCTATAA TCCTTCCAGG GGGCTGATCT GGCCAAAGTA    12120

CTAAATAAAA TATAATATTT CTTCTTTATT AACATTGTAG TCATATATGT GTACAATTGA    12180

TTATCTTGTG GGCCCTCATA AAGAAGCAGA AATTGGCTTG TATTTTGTGT TTACCCTATC    12240

AGCAATCTCT CTATTCTCCA AAGCACCCAA TTTTCTACAT TTGCCTGACA CGCAGCAAAA    12300

TTGAGCATAT GTTTCCTGCC TGCACCCTGT CTCTGACCTG TCAGCTTGCT TTTCTTTCCA    12360

GGATATGTGT TTGAACATAT TTCTCCAAAT GTTAAACCCA TTTCAGATAA TAAATATCAA    12420

AATTCTGGCA TTTTCATCCC TATAAAAACC CTAAACCCCG TGAGAGCAAA TGGTTTGTTT    12480

GTGTTTGCAG TGTCTACCTG TGTTTGCATT TTCATTTCTT GGGTGAATGA TGACAAGGTT    12540

GGGGTGGGGA CATGACTTAA ATGGTTGGAG AATTCTAAGC AAACCCCAGT TGGACCAAAG    12600

GACTTACCAA TGAGTTAGTA GTTTTCATAA GGGGCGGGG GGAGTGAGAG AAAGCCAATG    12660

CCTAAATCAA AGCAAAGTTT GCAGAACCCA AGGTAAAGTT CCAGAGATGA TATATCATAC    12720

AACAGAGGCC ATAGTGTAAA AAAATTAAAG AATGTCTGAT CAGCGTCTCA GCACATCTAC    12780

CAATTGGCCA GATGCTCAAA CAGAGTGAAG TCAGATGAGG TTCTGGAAAG TGAGTCCTCT    12840

ATGATGGCAG AGCTTTGGTG CTCAGGTTGG AAGCAAAACC TAGGGAGGGA GGGCTTTGTG    12900

GCTGTTTGCA GATTGGGGAA TCCAGTGCTA GTTCCTGGCA GGGTTTCAGG TCAGTTTCCG    12960
```

-continued

```
GAGTGTGTGT CCTGTAGCCC TCCGTCATGG TTGAAGCCCA GGTCTCACCT CCTCTCCTGA    13020

CCCGTGCCTT AGAACTGACT TGGAAAGCGG TGTGCTTACA GCAAGACAGA CTGTTATAAT    13080

TAAATTCTTC CCAAGGACCT CCGTGCAATG ACCCCAAGCA CACTTACCTT CGGAAACCTT    13140

AAGGTTCTGA AGATCTTGTT TTAAATGACT ACCCTGGTTA GCTTTTGATG TGTTCCTTAT    13200

CCCTTTAGTT GTTGCACAGG TAGAAACGAT TAGACCCAAC TATGGGTAGC CTTGTCCTCC    13260

TGGTCCTTCA GTCATTCTCT AATGTCTCTT GCTTGCCATG GGCACTGTAA CAAACTGCAA    13320

TCTTAACATC TTATAAAATG AATGAACCAC ATATTTACAT CTCCAAGTCC TCCAGATGGG    13380

AGTGCGATCA TTCCATAAGG ATCCCACCTT CTGGCAGGTC TATCCAGTAC ATATTTTATG    13440

CTTCATTGGT CTTGATTTTC TTGGCTAAAA TTACTTGTAG CACAGCAGGC CCATGTGAC    13500

ATATAGGTAT ATACATACAT GTATGTGCAT ATAGTGTGTA CATGTTCTAA TTTATACATA    13560

GCTATGTGAA GATTATGTTA CATATGTAGA TGGTCGCACT TCTGATTTCC ATTTAGGTTC    13620

AGAGAGAGAC GTCACAGTAA ATGGAGCTAT GTCATTGGTA TATCCCCGAG TGGTTCAGGT    13680

GTTCTCTCTA TTTTTTTAAG ATGGAGAACA CTCATCTGTA CTATCGAAAA CTGAGCCAAA    13740

TCACTTAGCA AATTTCTAGT CACTGCCTTG CTGTTAAGAT ACTGATTCAC TGGGTGCTGA    13800

CATGCTGAGC CCTGCCTACT TTTGCATGAA GGACAAGGAA GAGAGCTTGC AGTTAAGAAT    13860

GGTATATGTG GGGCTAGGGG GCGGCGTATA GACTGGCATA TATGTGAAGG AAGGTCACAA    13920

ACAGCCTGCA CTAATTTCCC TTTTCTGGTT TTATGTCTTG GCAGGGGAAA GGACAGGTAG    13980

GGTGGGGTTG AGGGGGAGGG CACACACATC TACTTGGATA AATTGCATCT CCTCTTTCCT    14040

TCACCCCGCC ACCATATCTT AAAGCCTTAT GACATCCTCT AGGGCAGAAT TTTCTCACCA    14100

GCTCCCCGCC CTACCAACTT CAAAGTGAAC TTCTAACTAA CTTGAGGGGC CAAAGTTCTA    14160

AATAAAACTT GTTAGAGTTT AGCGGGCACC TCAGTCATCA GGAATGCCTC CAGGAAAGCA    14220

AAAAGCTTGA TGTGTGTACA GCCACGTGGT GGAGTCCTGC CACCCTATGA TTCCTGTCCC    14280

AGTGGTCGTG TGGGGCCTGA GATCCTGAAT TTCTAATGAG CTCCCAGTAC GCCCTGACTC    14340

ACTGTGCCAG AGGACTGCAG TTTGAGTAGC AAGGTTGTGT GACTGTCTTC GATCATGGCT    14400

ACAGAAGCTG GCTCAAGTAC AGCCCTTCGT GTGTAAAAGC CATGTGTAAA TGAGAAGAAA    14460

CAGAAGGCAA AGCTGCGTTG CATGGCATCT GAATCAGTGC CCTGCAGTTT TGTTTTTTGT    14520

TTTTTTTTTT TCAAAGACAT TCTTTTTCCC AACAAGATGA GTGGCAATCT TATGTTCTAG    14580

CCACTCTTAG ACATGAAAAC ACTGGGTTGC TTATCTTGTA AAATCTGCTC TGCTTGCTTG    14640

CTTGGGCACG CTGCAGTCAG TTTAGTCAAA TGCGTGTCAG TACATCTATA TGTATGAGGG    14700

AGCAGGTGCA AGTCCTTAGA AATGTACTTT AAAAAACTTG AACACTTAAG TCAGTGTGCT    14760

GAGCTGCTCC TGTGTGATGT TAGGCCAAGC ACCTGAGTTA AAGGGATCTC TTTGAAGGCA    14820

GAGGGTAGAT GTCGTATGGT TGAAGCATTT GTTTATACTA AAATGATGCT TGACTTTTTT    14880

TCTAAGTTAT AAGACAGTAC ACTGTATAAG TTCATTGAAC CTAGAGGGTG GCATAGGACT    14940

CCAAATCTGG TATGGGAGGT TTGTTCTAAT GGAAGTTCGA ATCTTTTTTG CAGTTGGCTT    15000

GGAATAAAGT GCTTATGTGA ATGGGCTTAA GCTAGGGAAA AAAATGGGTT TCCCTCTGCA    15060

AAGAGGGTCA GCACAGAAAT AACTTCCTGG CTTTGCTTGC ATGAATGCCA CTTGTTAGCA    15120

GATGCCCTGT GGGGATCCGA ATTC                                          15144
```

(2) INFORMATION FOR SEQ ID NO:7:

(i) SEQUENCE CHARACTERISTICS:
        (A) LENGTH: 9299 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
GAATTCGCTA GGTAGACCAG GCTGGCCCAG AACACCTAGA GATCATCTGG CTGCCTCTGT      60

CTCTTGAGTT CTGGGCTAA AGCATGCACC ACTCTACCTG GCTAGTTTGT ATCCATCTAA      120

ATTGGGGAAG AAAGAAGTAC AGCTGTCCCC AGAGATAACA GCTGGGTTTT CCCATCAAAC     180

ACCTAGAAAT CCATTTTAGA TTCTAAATAG GGTTTGTCAG GTAGCTTAAT TAGAACTTTC     240

AGACTGGGTT TCACAGACTG GTTGGGCCAA AGGTCACTTT ATTGTCTGGG TTTCAGCAAA     300

ATGAGACAAT AGCTGTTATT CAAACAACAT TTGGGTAAGG AAGAAAAATG AACAAACACC     360

ACTCTCCCTC CCCCCGCTCC GTGCCTCCAA ATCCATTAAA GGCAAAGCTG CACCCCTAAG     420

GACAACGAAT CGCTGCTGTT TGTGAGTTTA AATATTAAGG AACACATTGT GTTAATGATT     480

GGAGCAGCAG TGATTGATGT AGTGGCATTG GTGAGCACTG AATCCGTCCT TCAACCTGCT     540

ATGGGAGCAC AGAGCCTGAT GCCCCAGGAG TAATGTAATA GAGTAATGTA ATGTAATGGA     600

GTTTTAATTT TGTGTTGTTG TTTTAAATAA TTAATTGTAA TTTTGGCTGT GTTAGAAGCT     660

GTGGGTACGT TTCTCAGTCA TCTTTTCGGT CTGGTGTTAT TGCCATACCT TGATTAATCG     720

GAGATTAAAA GAGAAGGTGT ACTTAGAAAC GATTTCAAAT GAAAGAAGGT ATGTTTCCAA     780

TGTGACTTCA CTAAAGTGAC AGTGACGCAG GGAATCAATC GTCTTCTAAT AGAAAGGGCT     840

CATGGAGACC TGAGCTGAAT CTTTCTGTTC TGGATGAGAG AGGTGGTACC CATTGGAATG     900

AAAGGACTTA GTCAGGGGCA ATACAGTGTG CTCCAAGGCT GGGGATGGTC AGGATGTTGT     960

GCTCAGCCTC TAACACTCCT TCCAACCTGA CATTCCTTCT CACCCTTTGT CTCTGGCCAG    1020

TAGAATACAG GAACTCGTTC CTGTTTTTTT TTTTTTAAAT TCTGAAGGTG TGTAAGTACA    1080

AAGGTCAGAT GAGCGGCCCT AGGTCAAGAC TGCTTTGTGG TGACAAGGGA GTATAACACC    1140

CACCCCAGAA ACCAAGAACC GGAAATTGCT ATCTTCCAGC CCTTTGAGAG CTACCTGAAG    1200

CTCTGGGCTG CTGGCCTCAC CCCTTCCCTG CAGCTTTCCC TTTAGCAGAG CTGTGATTT     1260

CCTTCAGCGC TTGGGCAAAT ACTCTTAGCC TGGCTCACCT TCCCCATCCT CGTTTGTAAA    1320

AACAAAGATG AAGCTGATAG TTCCTTCCCA GCTCCATCAG AGGCAGGGTG TGAAATTAGC    1380

TCCTGTTTGG GAAGGTTTAA AAGCCGGCCA CATTCCACCT CCCAGCTAGC ATGATTACCA    1440

ACTCTTGTTT CTTACTGTTG TTATGAAAGA CTCAATTCCT CATCTCCCTT TCCCTTCTTT    1500

TAAAAAGGGG CCAAAGGGCA CTTTGTTTTT TTCTCTACAT GGCCTAAAAG GCACTGTGTT    1560

ACCTTCCTGG AAGGTCCCAA ACAAACAAAC AAACAAACAA AATAACCATC TGGCAGTTAA    1620

GAAGGCTTCA GAGATATAAA TAGGATTTTC TAATTGTCTT ACAAGGCCTA GGCTGTTTGC    1680

CTGCCAAGTG CCTGCAAACT ACCTCTGTGC ACTTGAAATG TTAGACCTGG GGATCGATG     1740

GAGGGCACCC AGTTTAAGGG GGGTTGGTGC AATTCTCAAA TGTCCACAAG AAACATCTCA    1800

CAAAAACTTT TTTGGGGGGA AAGTCACCTC CTAATAGTTG AAGAGGTATC TCCTTCGGGC    1860

ACACAGCCCT GCTCACAGCC TGTTTCAACG TTTGGGAATC CTTTAACAGT TTACGGAAGG    1920

CCACCCTTTA AACCAATCCA ACAGCTCCCT TCTCCATAAC CTGATTTTAG AGGTGTTTCA    1980

TTATCTCTAA TTACTCGGGG TAAATGGTGA TTACTCAGTG TTTTAATCAT CAGTTTGGGC    2040

AGCAGTTATT CTAAACTCAG GGAAGCCCAG ACTCCCATGG GTATTTTTGG AAGGTACAGA    2100

GACTAGTTGG TGCATGCTTT CTAGTACCTC TTGCATGTGG TCCCCAGGTG AGCCCCGGCT    2160
```

-continued

```
GCTTCCCGAG CTGGAGGCAT CGGTCCCAGC CAAGGTGGCA ACTGAGGGCT GGGGAGCTGT    2220

GCAATCTTCC GGACCCGGCC TTGCCAGGCG AGGCGAGGCC CCGTGGCTGG ATGGGAGGAT    2280

GTGGGCGGGG CTCCCCATCC CAGAAGGGGA GGCGATTAAG GGAGGAGGGA AGAAGGGAGG    2340

GGCCGCTGGG GGGAAAGACT GGGGAGGAAG GGAAGAAAGA GAGGGAGGGA AAAGAGAAGG    2400

AAGGAGTAGA TGTGAGAGGG TGGTGCTGAG GGTGGGAAGG CAAGAGCGCG AGGCCTGGCC    2460

CGGAAGCTAG GTGAGTTCGG CATCCGAGCT GAGAGACCCC AGCCTAAGAC GCCTGCGCTG    2520

CAACCCAGCC TGAGTATCTG GTCTCCGTCC CTGATGGGAT TCTCGTCTAA ACCGTCTTGG    2580

AGCCTGCAGC GATCCAGTCT CTGGCCCTCG ACCAGGTTCA TTGCAGCTTT CTAGAGGTCC    2640

CCAGAAGCAG CTGCTGGCGA GCCCGCTTCT GCAGGAACCA ATGGTGAGCA GGGCAACCTG    2700

GAGAGGGGCG CTATTCTGAG GATTCGAGGT GCACCCGTAG TAGAAGCTGG GGATGGGGCT    2760

CAGGCTGTAA CCGAGGCAAA AGTTGGCCTA TTCCTCCTTC CTTCTCCAAC AGTGTTGGAG    2820

GTGGGATGAT GGAGGCTAAA AGGCACCTCC ATATATGTTA CTGCGTCTAT CAACCTACTT    2880

TAGGGAGGTG CGGGCCAGGA GAGGCGGGAA GGAGAGAAGG CCTTGGAAGA GAGGTCATTG    2940

GGAAGAACTG TGGGGTTTGG TGGGTTTGCT TCCACTTAGA CTATAAGAGT GGGAGAGGAG    3000

GGAGTCAACT CTAAGTTTCA ACACCAGTGG GGGACTGAGG ACTGCTTCAT TAGGAGAGAG    3060

AACCTAGCCA GAGCTAGCTT TGCAAAAGAG GCTGTAGTCC TGCTTTGCTC TAAAGCGCGA    3120

CCCGGGATAG AGAGGCTTCC TTGAGCGGGG TGTCACCTAA TCTTGTCCCC AACGCACCCC    3180

CTCCCAGCCC CTGAGAGCTA GCGAACTGTA GGTACACAAC TCGCTCCCAT CTCCAGGAGC    3240

TATTTTCTTA GACATGGGCA CCCATGATTC TGCCTTCTGG TACTCTCCCC TCCCTGGGAA    3300

AGGGGTGTAA GGTTCCGACG GAACCGTGGC CAGGATGCCG AAAGGCTACC TGTGCGGGTC    3360

TTCTGCCATG CTGTGTCTGT GCGGACATGC CAGCAGGGCT AATGAGGAGC TTGCGATACT    3420

CCAAAGGGTT CGGGAATTGC GGGGTCCTTA CACGCAGTGG AGTTGGGCCC CTTTTACTCA    3480

GAAGGTTTCC GCCACGGCTT TGGTTGATAG TTTTTTTAGT ATCCTGGTTT ATGAACTGAA    3540

GGTTTTGTGA GATGTTGAAT CACTAGCAGG GTCATATTTG GCAAACCGAG GCTACTATTA    3600

AATTTTGGTT TTAGAAGAAG ATTCTGGGGA GAAAGTGAAG GGTAACTGCC TCCAGGAGCT    3660

GTATCAACCC CATTAAGAAA AAAAAAAATA CCAGGAGATG AAAATTTACT TTGATCTGTA    3720

TTTTTTAATT AAAAAAAATC AGGGAAGAAA GGAGTGATTA GAAAGGGATC CTGAGCGTCG    3780

GCGGTTCCAC GGTGCCCTCG CTCCGCGTGC GCCAGTCGCT AGCATATCGC CATCTCTTTC    3840

CCCCTTAAAA GCAAATAAAC AAATCAACAA TAAGCCCTTT GCCCTTTCCA GCGCTTTCCC    3900

AGTTATTCCC AGCGGCGACG CGTGTCGGGG AATAGAGAAA TCGTCTCAGA AAGCTGCGCT    3960

GATGGTGGTG AGAGCGGACT GTCGCTCAGG GGCGCCCGCG GTCTCTGCAC CCAGGGCAGC    4020

AGTGTGGGAT GGCGCTGGGC AGCCACCGCC GCCAGGAAGG ACGTGACTCT CCATCCTTTA    4080

CACTTCTTTC TCAAAGGTTT CCCGAAAGTG CCCCCCGCCT CGAAAACTGG GGCCGGTGCG    4140

GGGGGGGGGA GAGGTTAGGT TGAAAACCAG CTGGACACGT CGAGTTCCTA AGTGAGGCAA    4200

AGAGGCGGGG TGGAGCGGGC TCTGGAGCGG GGGAGTCCTG GGACTCGGTC CTCGGATGGA    4260

CCCCGTGCAA AGACCTGTTG GAACAAGAGT TGCGCTTCCG AGGTTAGAAC AGGCCAGGCA    4320

TCTTAGGATA GTCAGGTCAC CCCCCCCCCC AACCCCACCC GAGTTGTGTT GGTGAATTTC    4380

TTGGAGGAAT CTTAGCCGCG ATTCTGTAGC TGGTGCAAAA GGAGGAAAGG GGTGGGGGAA    4440

GGAAGTGGCT GTGCGGGGGT GGCGGTGGGG GTGGAGGTGG TTTAAAAAGT AAGCCAAGCC    4500
```

```
AGAGGGAGAG GTCGAGTGCA GGCCGAAAGC TGTTCTCGGG TTTGTAGACG CTTGGGATCG    4560

CGCTTGGGGT CTCCTTTCGT GCCGGGTAGG AGTTGTAAAG CCTTTGCAAC TCTGAGATCG    4620

TAAAAAAAAT GTGATGCGCT CTTTCTTTGG CGACGCCTGT TTTGGAATCT GTCCGGAGTT    4680

AGAAGCTCAG ACGTCCACCC CCCACCCCCC GCCCACCCCC TCTGCCTTGA ATGGCACCGC    4740

CGACCGGTTT CTGAAGGATC TGCTTGGCTG GAGCGGACGC TGAGGTTGGC AGACACGGTG    4800

TGGGGACTCT GGCGGGGCTA CTAGACAGTA CTTCAGAAGC CGCTCCTTCT AACTTTCCCA    4860

CACCGCTCAA ACCCCGACAC CCCCGCGGCG GACTGAGTTG GCGACGGGGT CAGAGTCTTC    4920

TGGCTGAAAG TTAGATCCGC TAGGGGTCGG CTGCCTGTCG CTAGAAGCAT TATTTGGCCT    4980

CTCGGAGACC CGTGTGGAGG AAGTGCTGGA GTGTGCGAGT GTGTTTGCGT GTGTGTGTGT    5040

GTGTGTGTGT GTGTGTGTGT GTGTGTGTGT GTGCGCGCGC CCTTGGAGGG TCCCTATGCG    5100

CTTTCCTTTT CATGGAACGC TGTCGTGAGG CTTTGGTAAA CTGTCTTTTC GGTTCCTCTC    5160

TCGGCTGCAC TTAAGCTTTG TCGGCGCTGT AAAGAGACGC GTCTTCAAGT GCACCCTGAT    5220

CCTCAGGCTT CAGATAACCC GTCCCCGAAC CTGGCCAGAT GCATTGCACT GCGCGCCGCA    5280

GGTAGAGACG TGCCCCACGT CCCCTGCGTG CAGCGACTAC GACCGAGAGC CGCGCCAGTG    5340

TGGTGTCCCG CCGAGAGTTC CTCAGAGCAG GCGGGGACAA CTCCCAGACG GCTGGGGCTC    5400

CAGCTGCGGG CGCGGAGGTT GGCCTCGCTC GCAGGGGCTG GACCCAGCCG GGGTGGGAGG    5460

ATGGAGGAGG GGCGGGCGGG CTCTTCGGTG AGTGGGGCGG GGCCTCTGGG TCCACGTGAC    5520

TCCTAGGGGC TGGAAGAAAA ACAGAGCCTG TCTGCTCCAG AGTCTCATTA TATCAAATAT    5580

CATTTTAGGA GCCATTCCGT AGTGCCATTC GGAGCGACGC ACTGCCGCAG CTTCTCTGAG    5640

CCTTTCCAGC AAGTTTGTTC AAGATTGGCT CCCAAGAATC ATGGACTGTT ATTATGCCTT    5700

GTTTTCTGTC AGTGAGTAGA CACCTCTTCT TTCCCTTCTT GGGATTTCAC TCTGTCCTCC    5760

CATCCCTGAC CACTGTCTGT CCCTCCCGTC GGACTTCCAT TTCAGTGCCC CGCGCCCTAC    5820

TCTCAGGCAG CGCTATGGTT CTCTTTCTGG TCCCTGCAAG GCCAGACACT CGAAATGTAC    5880

GGGCTCCTTT TAAAGCGCTC CCACTGTTTT CTCTGATCCG CTGCGTTGCA AGAAAGAGGG    5940

AGCGCGAGGG ACCAAATAGA TGAAAGGTCC TCAGGTTGGG GCTGTCCCTT GAAGGGCTAA    6000

CCACTCCCTT ACCAGTCCCG ATATATCCAC TAGCCTGGGA AGGCCAGTTC CTTGCCTCAT    6060

AAAAAAAAAA AAAAAAACAA AAAACAAACA GTCGTTTGGG AACAAGACTC TTTAGTGAGC    6120

ATTTTCAACG CAGCGACCAC AATGAAATAA ATCACAAAGT CACTGGGGCA GCCCCTTGAC    6180

TCCTTTTCCC AGTCACTGGA CCTTGCTGCC CGGTCCAAGC CCTGCCGGCA CAGCTCTGTT    6240

CTCCCCTCCT CCTGTTCTTA ACCAGCTGGA AGTTGTGGAA ATTGGGCTGG AGGGCGGAGG    6300

AAGGGCGGGG GTGGGGGGGT GGAGAAGGTG GGGGGGGGGG AGGCTGAAGG TCCGAAGTGA    6360

AGAGCGATGG CATTTTAATT CTCCCTCCGC CTCCCCCCTT TACCTCCTCA ATGTTAACTG    6420

TTTATCCTTG AAGAAGCCAC GCTGAGATCA TGGCTCAGAT AGCCGTTGGG ACAGGATGGA    6480

GGCTATCTTA TTTGGGGTTA TTTGAGTGTA AACAAGTTAG ACCAAGTAAT TACAGGGCGA    6540

TTCTTACTTT CGGGCCGTGC ATGGCTGCAG CTGGTGTGTG TGTGTGTAGG GTGTGAGGGA    6600

GAAAACACAA ACTTGATCTT TCGGACCTGT TTTACATCTT GACCGTCGGT TGCTACCCCT    6660

ATATGCATAT GCAGAGACAT CTCTATTTCT CGCTATTGAT CGGTGTTTAT TTATTCTTTA    6720

ACCTTCCACC CCAACCCCCT CCCCAGAGAC ACCATGATTC CTGGTAACCG AATGCTGATG    6780

GTCGTTTTAT TATGCCAAGT CCTGCTAGGA GGCGCGAGCC ATGCTAGTTT GATACCTGAG    6840

ACCGGGAAGA AAAAGTCGC CGAGATTCAG GGCCACGCGG GAGGACGCCG CTCAGGGCAG    6900
```

-continued

```
AGCCATGAGC TCCTGCGGGA CTTCGAGGCG ACACTTCTAC AGATGTTTGG GCTGCGCCGC      6960

CGTCCGCAGC CTAGCAAGAG CGCCGTCATT CCGGATTACA TGAGGGATCT TTACCGGCTC      7020

CAGTCTGGGG AGGAGGAGGA GGAAGAGCAG AGCCAGGGAA CCGGGCTTGA GTACCCGGAG      7080

CGTCCCGCCA GCCGAGCCAA CACTGTGAGG AGTTTCCATC ACGAAGGTCA GTTTCTGCTC      7140

TTAGTCCTGG CGGTGTAGGG TGGGGTAGAG CACCGGGGCA GAGGGTGGGG GGTGGGCAGC      7200

TGGCAGGGCA AGCTGAAGGG GTTGTGGAAG CCCCCGGGGA AGAAGAGTTC ATGTTACATC      7260

AAAGCTCCGA GTCCTGGAGA CTGTGGAACA GGGCCTCTTA CCTTCAACTT TCCAGAGCTG      7320

CCTCTGAGGG TACTTTCTGG AGACCAAGTA GTGGTGGTGA TGGGGGAGGG GGTTACTTTG      7380

GGAGAAGCGG ACTGACACCA CTCAGACTTC TGCTACCTCC CAGTGGGTGT TCTTTAGCTA      7440

TACCAAAGTC AGGGATTCTG CCCGTTTTGT TCCAAAGCAC CTACTGAATT AATATTACA      7500

TCTGTGTGTT TGTCAGGTTT ATCAATAGGG GCCTTGTAAT ACGATCTGAA TGTTTCCTAG      7560

CGGATGTTTC TTTTCCAAAG TAAATCTGAG TTATTAATCC TCCAGCATCA TTACTGTGTT      7620

GGAATTTATT TTCCCTTCTG TAACATGATC AACAAGGCGT GCTCTGTGTT TCTAGGATCG      7680

CTGGGGAAAT GTTTGGTAAC ATACTCAAAA GTGGAGAGGG AGAGAGGGTG GCCCCTCTTT      7740

TTCTTTACAA CCACTTGTAA AGAAAACTGT ACACAAAGCC AAGAGGGGGC TTTAAAAGGG      7800

GAGTCCAAGG GTGGTGGAGT AAAAGAGTTG ACACATGGAA ATTATTAGGC ATATAAAGGA      7860

GGTTGGGAGA TACTTTCTGT CTTTGGTGTT TGACAAATGT GAGCTAAGTT TTGCTGGTTT      7920

GCTAGCTGCT CCACAACTCT GCTCCTTCAA ATTAAAAGGC ACAGTAATTT CCTCCCCTTA      7980

GGTTTCTACT ATATAAGCAG AATTCAACCA ATTCTGCTAT TTTTTGTTTT TGTTTCTTGT      8040

TTTTGTTTTG TTTGGTTTTT TTTTTTTTTT TTTTTTTTT GTCTCAGAAA AGCTCATGGG      8100

CCTTTTCTTT TCCCCTTTCA ACTGTGCCTA GAACATCTGG AGAACATCCC AGGGACCAGT      8160

GAGAGCTCTG CTTTTCGTTT CCTCTTCAAC CTCAGCAGCA TCCCAGAAAA TGAGGTGATC      8220

TCCTCGGCAG AGCTCCGGCT CTTTCGGGAG CAGGTGGACC AGGGCCCTGA CTGGGAACAG      8280

GGCTTCCACC GTATAAACAT TTATGAGGTT ATGAAGCCCC CAGCAGAAAT GGTTCCTGGA      8340

CACCTCATCA CACGACTACT GGACACCAGA CTAGTCCATC ACAATGTGAC ACGGTGGGAA      8400

ACTTTCGATG TGAGCCCTGC AGTCCTTCGC TGGACCCGGG AAAAGCAACC CAATTATGGG      8460

CTGGCCATTG AGGTGACTCA CCTCCACCAG ACACGGACCC ACCAGGGCCA GCATGTCAGA      8520

ATCAGCCGAT CGTTACCTCA AGGGAGTGGA GATTGGGCCC AACTCCGCCC CCTCCTGGTC      8580

ACTTTTGGCC ATGATGGCCG GGGCCATACC TTGACCCGCA GGAGGGCCAA ACGTAGTCCC      8640

AAGCATCACC CACAGCGGTC CAGGAAGAAG AATAAGAACT GCCGTCGCCA TTCACTATAC      8700

GTGGACTTCA GTGACGTGGG CTGGAATGAT TGGATTGTGG CCCCACCCGG CTACCAGGCC      8760

TTCTACTGCC ATGGGACTG TCCCTTTCCA CTGGCTGATC ACCTCAACTC AACCAACCAT      8820

GCCATTGTGC AGACCCTAGT CAACTCTGTT AATTCTAGTA TCCCTAAGGC CTGTTGTGTC      8880

CCCACTGAAC TGAGTGCCAT TTCCATGTTG TACCTGGATG AGTATGACAA GGTGGTGTTG      8940

AAAAATTATC AGGAGATGGT GGTAGAGGGG TGTGGATGCC GCTGAGATCA GACAGTCCGG      9000

AGGGCGGACA CACACACACA CACACACACA CACACACACA CACACACACA CACGTTCCCA      9060

TTCAACCACC TACACATACC ACACAAACTG CTTCCCTATA GCTGGACTTT TATCTTAAAA      9120

AAAAAAAAAA GAAAGAAAGA AAGAAAGAAA GAAAAAAAT GAAAGACAGA AAAGAAAAAA      9180

AAAACCCTAA ACAACTCACC TTGACCTTAT TTATGACTTT ACGTGCAAAT GTTTTGACCA      9240
```

```
TATTGATCAT ATTTTGACAA ATATATTTAT AACTACATAT TAAAAGAAAA TAAAATGAG        9299

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

CGGATGCCGA ACTCACCTA                                                     19

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CTACAAACCC GAGAACAG                                                      18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CCCGGCACGA AAGGAGAC                                                      18

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GAAGGCAAGA GCGCGAGG                                                      18

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CCCGGTCTCA GGTATCA                                                       17

(2) INFORMATION FOR SEQ ID NO:13:
```

```
    (i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CAGGCCGAAA GCTGTTC                                                17
```